(12) United States Patent
Brinton et al.

(10) Patent No.: US 9,572,860 B2
(45) Date of Patent: *Feb. 21, 2017

(54) METHODS AND COMPOSITIONS FOR INHIBITION OF VIRAL REPLICATION

(75) Inventors: Margo A. Brinton, Decatur, GA (US); Mohamed M. Emara, Atlanta, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 624 days.

This patent is subject to a terminal disclaimer.

(21) Appl. No.: 11/879,493

(22) Filed: Jul. 16, 2007

(65) Prior Publication Data

US 2009/0186842 A1 Jul. 23, 2009

Related U.S. Application Data

(63) Continuation-in-part of application No. 10/654,273, filed on Sep. 2, 2003, now Pat. No. 8,303,946.

(60) Provisional application No. 60/407,105, filed on Aug. 30, 2002, provisional application No. 60/831,001, filed on Jul. 14, 2006.

(51) Int. Cl.

| | |
|---|---|
| *C12N 15/113* | (2010.01) |
| *C12N 7/00* | (2006.01) |
| *C12N 15/40* | (2006.01) |
| *A61K 38/16* | (2006.01) |
| *C12N 15/115* | (2010.01) |
| *C12Q 1/18* | (2006.01) |

(52) U.S. Cl.
CPC .............. *A61K 38/162* (2013.01); *C12N 7/00* (2013.01); *C12N 15/115* (2013.01); *C12N 15/1131* (2013.01); *C12Q 1/18* (2013.01); *C12N 2310/13* (2013.01); *C12N 2770/24111* (2013.01); *G01N 2333/18* (2013.01)

(58) Field of Classification Search
USPC ................................................. 536/24.1, 24.5
See application file for complete search history.

(56) References Cited

U.S. PATENT DOCUMENTS

| 5,798,245 A | 8/1998 | Anderson et al. | |
|---|---|---|---|
| 8,303,946 B2 * | 11/2012 | Brinton ................ | A61K 38/162 424/93.1 |
| 2005/0032729 A1* | 2/2005 | Shyamala ........................ | 514/44 |
| 2008/0311556 A1* | 12/2008 | Iversen ............................. | 435/5 |

OTHER PUBLICATIONS

Shi et al. J. Virol. 1996, vol. 70, No. 9, pp. 6278-6287.*
Li et al. J. Virol. 2002, vol. 76, No. 23, pp. 11989-12000.*
Wengler et al. J. Gen. Virol. 1986, vol. 67, pp. 1183-1188.*
Olsthoorn et al. RNA, 2001, vol. 7, pp. 1370-1377.*
Emara. PNAS 2007, vol. 104, No. 21, pp. 9041-9046.*
Rauscher et al. RNA, 1997, vol. 3, pp. 779-791.*
Valiakos et al, West Nile Virus: Basic Principles, Replication Mechanism, Immune Response and Important Genetic Determinants of Virulence, Chapter 2, INTECH, 2013, pp. 43-68.*
Aigner, A. Application of RNA interference: current state and prospects for siRNA-based strategies in vivo. 2007. Appl Micriobiol Biotechnol. 76:9-21.
Anderson, P., Kedersha, N. 2002. Stressful initiations. Journal of Cell Science 115:3227-3234.
Beck, A. R., Q. G. Medley, S. O'Brien, P. Anderson, and M. Streuli 1996. Structure, tissue distribution and genomic organization of the murine RRM-type RNA binding proteins TIA-1 and TIAR Nucleic Acids Res. 24:3829-35.
Beck, A. R., I. J. Miller, P. Anderson, and M. Streuli 1998. RNA-binding protein TIAR is essential for primordial germ cell development Proc Natl Acad Sci U S A. 95:2331-6.
Blackwell, J.L.. and M.A. Brinton, 1995. BHK cell proteins that bind to the 3' Stem-Loop Structure of the West Nile virus genome RNA. J. Virol. 69(9): 5650-58.
Blackwell, J.L.. and M.A. Brinton, 1997. Translation Elongation Factor-1 Alpha Interacts with 3' stem-loop region of West Nile Virus Genomic RNA.
Blyn, L.B., K.M. Swiderek, O. Richards, D.C. Stahl, B.L. Semler, and E. Ehrenfeld 1996. Poly(rC) binding protein 2 binds to stem-loop IV of the poliovirus RNA 5' noncoding region, Proc Natl Acad Sci USA 93:11115-20.
Blyn, L.B., J.S. Towner, B.L. Semler, and E. Ehrenfeld 1997. Requirement of poly(rC) binding protein 2 for translation of poliovirus RNA J Virol. 71:6243-6.
Brand, S., and H.M. Bourbon 1993. The developmentally-regulated *Drosophila* gene rox8 encodes an RRM-type RNA binding protein structurally related to human TIA-1-type nucleolysins Nucleic Acids Res. 21:3699-704.
Brinton, M.A., 2002. The molecular biology of west nile virus: a new invader of the western hemisphere Annu. Rev. Microbiol. 56:371-402.
Brinton, M.A. 1997. Host susceptibility to viral disease, p. 303-328. In N.N. e. al (ed.), Vi Lippincott-Raven Publishers, Philadelphia.
Brinton, M.A., and J.H. Dispoto 1988. Sequence and secondary structure analysis of flavivirus genome RNA Virology. 162:290-9.
Brinton, M. A., A. V. Fernandez, and J. H. Dispoto 1986. The 3'-nucleotides of flavivirus genomic RNA form a conserved secondary structure Virology. 153:113-21.
Cok, J, S.J. Action, A.R. Morrison 2003 The proximal region of the 3'-untranslated region of cyclooxygenase-2 is recognized by a multimeric protein complex containing HuR, TIA-1, TIAR, and the heterogeneous nuclear ribonucleoprotein.

(Continued)

*Primary Examiner* — Maria Marvich
(74) *Attorney, Agent, or Firm* — Troutman Sanders LLP; Ryan A. Schneider; Troy S. Kleckley

(57) ABSTRACT

The present invention is directed to methods and compositions that are effective in the inhibition of viral replication. In particular, the methods and compositions are effective at interfering with the activity of host cell proteins required in viral replication. For example, an embodiment of the invention is directed to methods and compositions comprising RNA sequences to which the host cell proteins TIAR and/or TIA-1 bind.

7 Claims, 30 Drawing Sheets

(56) References Cited

OTHER PUBLICATIONS

Davanloo, P., A. H. Rosenberg, J. J. Dunn, and F. W. Studier 1984. Cloning and expressions of the gene for bacteriophase T7 RNA polymerase Proc Natl Acad Sci USA. 81:2035-9.

Davis, L.E., Debiasi, R., Goade, D. E., Halland, K.Y., Harrington, J.A., Harnar, J.B., Pergam, S.A., King, M.K., Demasters, B.K., and Tyler, K.L. West Nile virus Neuroinvasive Disease. 2006. Ann Neurol. 60:286-300.

Davis, M. T., and T. D. Lee 1998. Rapid protein identification using a microscale electrospray LC/MS system on an ion trap mass spectrometer J Am Soc Mass Spectrom. 9:194-201.

Davis, M. T., and T. D. Lee 1997. Variable flow liquid chromatography-tandem mass spectrometry and the comprehensive analysis of complex protein digest mixtures J Am Soc Mass Spectrom. 8:1059-1069.

Del Gatto-Konczak, F., C.F. Bourgeois, C. Le Guiner, L. Kister, M.C. Gesnel, J. Stevenin, and R. Breathnach 2000. The RNA-binding protein TIA-1 is a novel mammalian splicing regulator acting through intron sequences adjacent to a 5' splice site Mol Cell Biol 20:6287-99.

Dember, L.M., N.D. Kim, K.Q. Liu, and P. Anderson 1996. Individual RNA recognition motifs of TIA-1 and TIAR have different RNA binding specifications. J. Biol Chem. 271:2783-8.

Forch, P., and J. Valcarcel 2001. Molecular mechanisms of gene expression regulation by the apoptosis-promoting protein TIA-1 Apoptosis. 6:463-8.

Fukui, Y., S. Yumura, and T.K. Yumura 1987. Agar-overlay immunofluorescence: high-resolution studies of cytoskeletal components and their changes during chemotaxis. Methods Cell Biol. 28:347-56.

Geiss, B.J., Pierson, T.C., Diamond, M.S. Actively replicating West Nile virus is resistant to cytoplasmic delivery of siRNA. 2005. Virology Journal. 2(53):1-13.

Gueydan, C., L. Droogmans, P. Chalon, G. Huez, D. Caput, and V. Kruys 1999. Identification of TIAR as a protein binding to the translational regulatory AU-rich element of tumor necrosis factor alpha mRNA J Biol Chem. 274:2322-6.

Iseni, F., D. Garcin, M. Nishio, N. Kedersha, P. Anderson, and D. Kolakofsky, 2002. Sendai virus trailer RNA binds TIAR, a cellular protein involved in virus-induced apoptosis The EMBO Journal vol. 21, No. 19, pp. 5141-5150.

Jessen, T. H., C. Oubridge, C. H. Teo, C. Pritchard, and K. Nagai 1991. dentification of molecular contacts between the U1 A small nuclear ribonucleoprotein and U1 RNA Embo J. 10:3447-56.

Jordan, I., Briese, T., Fischer, N., Lau, Y., Lipkin, W. I., Ribavirin inhibits West Nile replication and cytopathic effect in neural cells. 2000. JID. 182:1214-7.

Kawakami, A., Q. Tian, X. Duan, M. Streuli, S. F. Schlossman, and P. Anderson 1992. Identification and functional characterization of a TIA-1-related nucleolysin Proc Natl Acad Sci U S A. 89:8681-5.

Kedersha, N., S. Chen, N. Gilks, W. Li, I. J. Miller, J. Stahl and P. Anderson 2002. Evidence that ternary complex (elF2-GTP-tRNA(i)(Met))-deficient preinitiation complexes are core constituents of mammalian stress granules Mol Biol Cell. 13:195-210.

Kedersha, N. L., M. Gupta, W. Li, I. Miller, and P. Anderson 1999. RNA-binding proteins TIA-1 and TIAR link the phosphorylation of elF-2 alpha to the assembly of mammalian stress granules J Cell Biol. 147:1431-41.

Kim, Y. J., and B. S. Baker 1993. Isolation of RRM-type RNA-binding protein genes and the analysis of their relatedness by using a numerical approach Mol Cell Biol. 13:174-83.

Kotani, E., T. Ohba, T. Niwa, K. B. Storey, J. S. Storey, H. Saito, Y. Sugimura, and T. Furusawa 2003 De novo gene expression and antisense inhibition in cultured cells of BmTRN-1, cloned from the midgut of the silkworm, *Bombyx mori*, which is homologous with mammalian TIA-1/R. Gene Journal 320:67-9, Elsevier.

Lanciotti, R. S., J. T. Roehrig, V. Deubel, J. Smith, M. Parker, K. Steele, B. Crise, K. E. Volpe, M. B. Crabtree, J. H. Scherret, R. A. Hall, J.S. MacKenzie, C.B. Cropp, B. Panigrahy, E. Ostlund, B. Schmitt, M. Malkinson, C. Banet, J. Weissman, N. Komar, H.M. Savage, W. Stone, T. McNamara, and D. J. Gubler 1999. Origin of the west nile virus responsible for outbreak of encephalitis in northeastern United States Science. 286:2333-7.

Le Guiner C., M. C. Gesnel, and R. Breathnach 2003 TIA-1 or TIAR is required for DT40 cell viability. J Biol Chem. vol. 278, No. 12, pp. 10465-10476.

Le Guiner, C., F. Lejeune, D. Galiana, L. Kister, R. Breathnach, J. Stevenin, and F. Del Gatto-Konczak 2001. TIA-1 and TIAR activate splicing of alternative exons with weak 5' splice sites followed by a U-rich stretch on their own pre-mRNAs J Biol Chem. 276:40638-46.

Lewis, T., C. Gueydan, G. Huez, J. J. Toulme, and V. Kruys 1998. Mapping of a minimal Au-rich sequence required for lipopolysaccharide-induced binding of a 55-kDa protein on tumor necrosis factor-alpha mRNA J Biol Chem. 273:13781-6.

Li, W., Y. Li, N. Kedersha, P. Anderson, M. Emara, K. M. Swiderek, G. T. Moreno, and M.A. Brinton 2002 Cell proteins TIA-1 and TIAR Interact with the 3' stem-loop of the west nile virus complementary minus-strand RNA and facilitate virus replication J Virology vol. 76, No. 23pp. 11989-12000.

Li, W. and Brinton, M.A. The 3' stem loop of the West Nile virus genomic RNA can suppress translation of chimeric mRNAs. 2001. Virology. 287:49-61.

Lindenbach, B. D., and C. M. Rice 2001. Flaviviridae: The viruses and their replication, p. 589-639. In D. M. Knipe, and P. M. Howley (eds), Fields Virology. Lippencott Williams and Wilkins, Philadelphia.

Lu, C. D., J. E. Houghton, and A. T. Abdelal 1992. Characterization of the arginine repressor from *Salmonella typhimurium* and its interactions with the carAB operator J Mol Biol. 225:11-24.

MacKenzie, J. M., M. K. Jones, and E. G. Westaway 1999. Markers for trans-Golgi membranes and the intermediate compartment localize to induced membranes with distinct replication functions in flavivirus-infected cells J Virol. 73:9555-67.

MacKenzie, J. M., A. A. Khromykh, M. K. Jones, and E. G. Westaway 1998. Subcellular localization and some biochemical properties of the flavivirus Kunjin nonstructural proteins NS2A and NS4A Virology. 245:203-15.

Men, R., M. Bray, D. Clark, R. M. Chanock, and C. J. Lai 1996. Dengue type 4 virus mutants containing deletions in the 3' noncoding region of the RNA genome: analysis of growth restriction in cell culture and altered viremia pattern and immunogenicity in rhesus monkeys J Virol. 70:3930-7.

Morrey, J., Smee, D.F., Sidwel, R.W., and Tseng, C. Identification of active antiviral compounds against a New York isolate of West Nile virus. 2002. Anitivral Research. 55:107-116.

Parquet, M. C., A. Kumatori, F. Hasebe, K. Morita, and A. Igarashi 2001. West Nile virus-induced bax-dependent apoptosis FEBS Lett. 500:17-24.

Piecyk, M., S. Wax, A. R. Beck, N. Kedersha, M. Gupta, B. Maritim, S. Chen, C. Gueydan, V. Kruys, M. Streuli, and P. Anderson 2000. TIA-1 is a translational silencer that selectively regulates the expression of TNF-alpha Embo J. 19:4154-63.

Rice, C. M. 1996. Fields Virology, 3rd Edition, pp. 931-959 Lippincott-Raven Publishers, Philadelphia.

Shi, P. Y., M. A. Brinton, J. M. Veal, Y. Y. Zhong, and W. D. Wilson 1996. Evidence for the existence of a pseudoknot structure at the 3' terminus of the flavivirus genomic RNA Biochemistry. 35:4222-30.

Shi, P. Y., W. Li, and M. A. Brinton 1996. Cell proteins bind specifically to West Nile virus minus-strand 3' stem-loop RNA J Virol. 70:6278-87.

Taupin, J. L., Q. Tian, N. Kedersha, M. Robertson, and P. Anderson 1995. The RNA-binding protein TIAR is translocated from the nucleus to the cytoplasm during Fas-mediated apoptotic cell death Proc Natl Acad Sci U S A. 92:1629-33.

Tian, Q., M. Streuli, H. Saito, S. F. Schlossman, and P. Anderson 1991. A polyadenylate binding protein localized to the granules of cytolytic lymphocytes induces DNA fragmentation in target cells Cell. 67:629-39.

Tian, Q., J. Taupin, S. Elledge, M. Robertson, and P. Anderson 1995. Fas-activated serine/threonine kinase (FAST) phosphorylates TIA-1 during Fas-mediated apoptosis J Exp Med. 182:865-74.

(56) References Cited

OTHER PUBLICATIONS

Verma, I.M and Somia, N. 1997. Gene therapy—promise, problems and prospects. Nature. 389:239-242.
Weeks, K. M., and D. M. Crothers 1992. RNA binding assays for Tat-derived peptides: implications for specificity Biochemistry. 31:10281-7.
Wilson, R., R. Ainscough, K. Anderson, C. Baynes, M. Berks, J. Bonfield, J. Burton, M. Connell, T. Copsey, J. Cooper, et al. 1994. 2.2 Mb of contiguous nucleotide sequence from chromosome III of C. elegans Nature. 368:32-8.
Yu, Q., S. J. Cok, C. Zeng, A. R. Morrison, 2003 Translational repression of human matrix metalloproteinases-13 by an alternatively spliced form of T-cell restricted intracellular antigen-related protein (TIAR) J of Biological Chemistry, vol. 278, pp. 1579-1584.
Zeng, L., B. Falgout, and L. Markoff 1998. Identification of specific nucleotide sequences within the conserved 3'-SL in the dengue type 2 virus genome required for replication J Virol. 72:7510-22.
Zhang, T., V. Kruys, G. Huez, and C. Gueydan 2002. Au-rich element-mediated translational control: complexity and multiple activities of trans-activating factors. Biochemical Society Transactions, vol. 30, pp. 952-958.
Zhu, H., R. A. Hasman, K. M. Young, N. L. Kedersha, and H. Lou 2003. U1 snRNP-dependent function of TIAR in the regulation of alternative RNA processing of the human calcitonin/CGRP pre-mRNA.

* cited by examiner

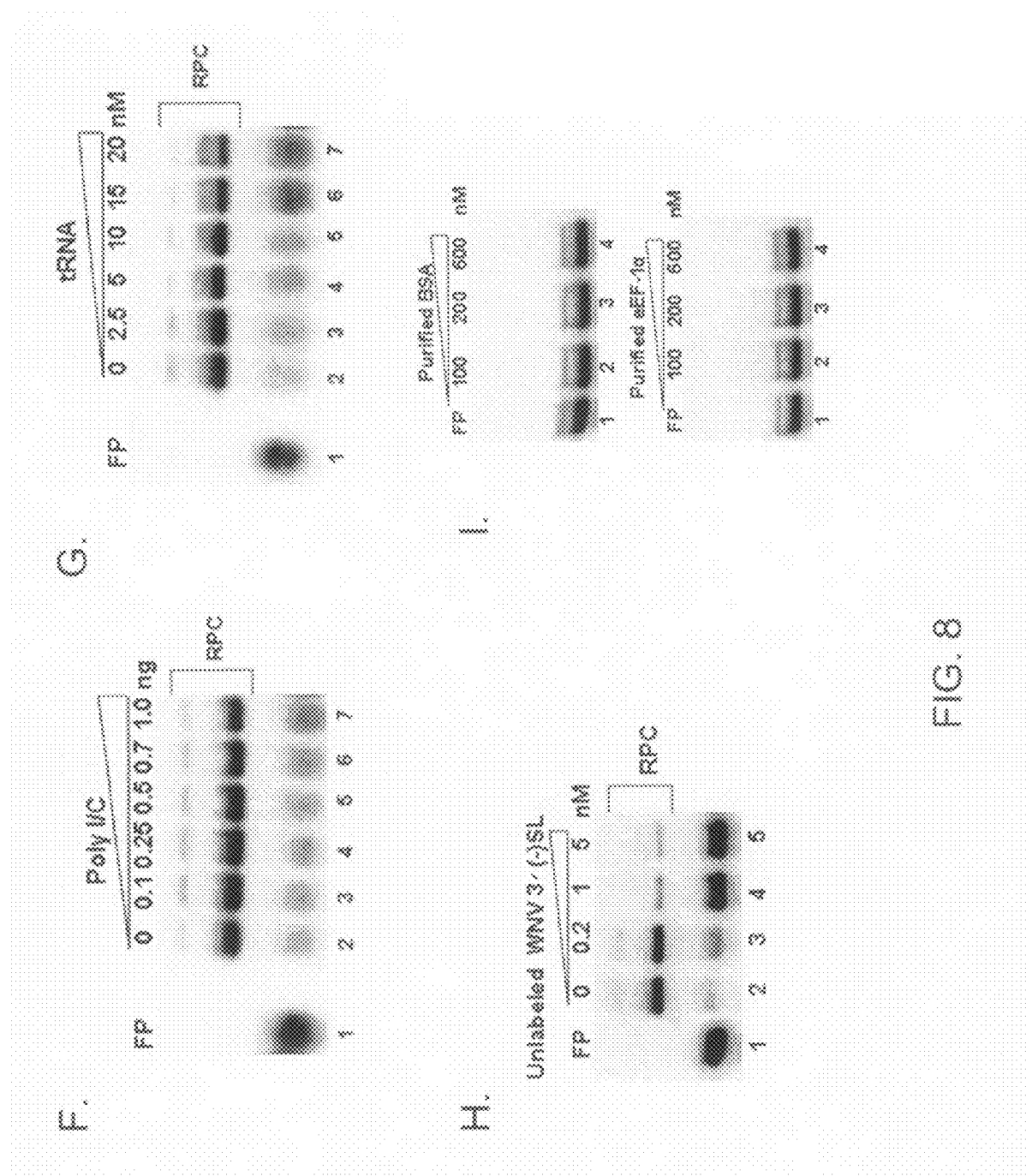

METHODS AND COMPOSITIONS FOR INHIBITION OF VIRAL REPLICATION

RELATED APPLICATIONS

The present invention claims priority to U.S. Provisional Patent Application No. 60/831,001, filed Jul. 14, 2006, and is a continuation-in-part application of U.S. patent application Ser. No. 10/654,273, filed Sep. 2, 2003, which is now U.S. Pat. No. 8,303,946, issued on Nov. 6, 2015, and which claims priority to U.S. Provisional Patent Application No. 60/407,105, filed Aug. 30, 2002, each of which is herein incorporated in its entirety.

STATEMENT OF FEDERALLY SPONSORED RESEARCH

This invention was made with U.S. government support under Grant No. AI048088 awarded by the National Institutes of Health. The U.S. government has certain rights in the invention.

TECHNICAL FIELD

This invention is directed to methods and compositions for the inhibition of viral replication. In particular, the invention is directed to methods and compositions that interact with host proteins necessary for viral replication, or that interact with the viral nucleic acid to inhibit viral replication.

BACKGROUND OF THE INVENTION

Viruses cause some of the most debilitating illnesses known in humans, animals and plants. Vaccination procedures have provided some relief for humans and animals from some of the more deadly viruses, such as smallpox, measles, influenza and poliovirus. However, many viruses still cause much human suffering, loss of work days, death to animals and destruction of plants. Unlike bacteria, viruses use the host's own cellular mechanisms to reproduce.

Increased globalization has resulted in the invasion of new territories by viruses that were previously found only in specific geographic locations. A well known example of this is the spread of human immunodeficiency virus around the world. A recent example is the spread of West Nile virus into and through the United States.

West Nile virus is a mosquito-borne virus that was first isolated in 1937 from the blood of a patient in the West Nile region of Uganda. It has been endemic in parts of Africa, the Middle East and India. Wild birds are the main reservoir hosts, with human and horses acting as incidental hosts with no role in virus transmission.

West Nile virus (WNV) was first detected in the Western hemisphere in 1999, in New York state, United States. The mode of introduction of WNV into the United States is not known, but phylogenic analysis of the envelope gene of a WNV isolate indicates it was closely related to a WNV isolate in Israel. WNV transmission reoccurred in New York during the summers of 2000 and 2001, and the virus has spread southward and westward in the United States. It is expected that the virus will continue to spread throughout the United States, Canada, the Caribbean, and Central and South America. Mosquitoes capable of transmitting WNV to susceptible birds exist in all of these regions.

The incidence of clinical disease among WNV-infected humans is low, though in recent outbreaks there has been an increase in the severity of disease among those that develop clinical symptoms. Fever is the most common symptom, and other symptoms include headache, muscle weakness and disorientation. A few infected individuals develop encephalitis, meningoencephalitis, polio-like paralysis, Parkinson's disease-like symptoms or hepatitis. Most infected persons show no sign of infection. It is thought that in the 1999 outbreak in the U.S., 1900 persons were infected. Sixty-two developed clinical disease and of these, 7 died.

It is expected that microbial agents, such as viruses, will continue to be spread to new territories and that such agents will need to be identified and treatments provided to the unprotected populations. One method of protection, that would not be dependent on specific viral identification, would be to provide compositions that interact with host proteins that are commonly involved in the viral replication pathways of different related viruses, such as flaviviruses, to stop or interfere with viral replication.

What is needed are methods for identification of components of the viral replication cycle that can be interfered with or inhibited so that viral replication or the spread of infection in the host is interrupted, without harming the host, and the development of compositions that are effective in inhibiting or interfering with viral replication.

SUMMARY OF THE INVENTION

The present invention is directed to methods and compositions for inhibiting viral replication. Methods are described herein that identify proteins or regions of the viral nucleic acid that are important in viral replication. In particular, flavivirus replication is described wherein host proteins are important in replication of the virus. Methods of the present invention also include inhibiting the interactions of host proteins with viral components or inhibiting or interfering with viral nucleic acids to inhibit viral replication. Compositions comprising compounds, including nucleic acid constructs or small molecules that inhibit such viral replication are also included in the present invention.

Such compositions are easily administered by oral, subcutaneous, intravenous and routes known to those skilled in the art and can be given in dosages that are safe and provide inhibition of viral replication. The present invention provides methods of treating diseases, found in humans, animals and plants mediated by viral infection, comprising administering compositions comprising anti-viral compounds in dosages effective to inhibit viral replication.

Compositions may comprise the binding sites for TIA-1 and TIAR within the WNV3'(−)SL RNA. Both TIA-1 and TIAR bind to short single-stranded AU-rich sequences in the context of an RNA secondary structure. Compositions comprise sequences for binding of TIA-1 or TIAR including RNA sequences having two closely spaced loops containing either UAAU, AAAA, or UUUU sequences. Mutant WNV are also taught.

DETAILED DESCRIPTION

The present invention is directed to methods and compositions that are effective in inhibiting viral replication. In particular, the present invention is directed to methods for identifying components of the viral replication cycle that are necessary for replication, such as proteins, and testing for compounds that are effective in the inhibition of these components. Inhibition of viral replication leads to little or no infected state in the organism, or reduces or terminates the infection in the organism.

Compositions and methods for the treatment of viral diseases that are mediated by inhibition of viral replication are also provided. Particularly, methods and compositions of the present invention are directed to inhibition of the activity of host cell proteins that are required for replication of viruses. Methods and compositions of the present invention are also directed to inhibiting or interfering with the viral nucleic acids to inhibit viral replication. Methods for the identification of cellular factors that are required to complete various steps of a virus lifecycle are also provided.

For example, one family of viruses that creates debilitating and deadly disease in humans and animals is Flaviviridae. This family consists of three genera, one of which is the genus Flavivirus. Flaviviruses are transmitted between bird and mammalian hosts via mosquitoes or ticks. Flaviviruses, such as dengue, Japanese encephalitis virus, West Nile virus (WNV), yellow fever virus, St. Louis encephalitis virus, Murray Valley encephalitis virus, and tick-borne encephalitis virus, can sometimes cause severe disease in infected humans (10, 24).

The genomes of flaviviruses are single-stranded, positive-polarity RNAs of approximately 11 kb and encode a single large polyprotein that is post-translationally processed by viral and cellular proteases into three structural proteins and seven non-structural proteins (34). During the flavivirus replication cycle, which takes place in the cytoplasm of infected cells, the genomic RNA (plus strand RNA) serves as the only viral mRNA and is also the template for transcription of the complementary minus-strand RNA. The minus-strand RNA in turn serves as a template for the synthesis of genomic RNA. Plus-strand RNA synthesis is 10 to 100 times more efficient than minus-strand synthesis (34).

Figure 7:
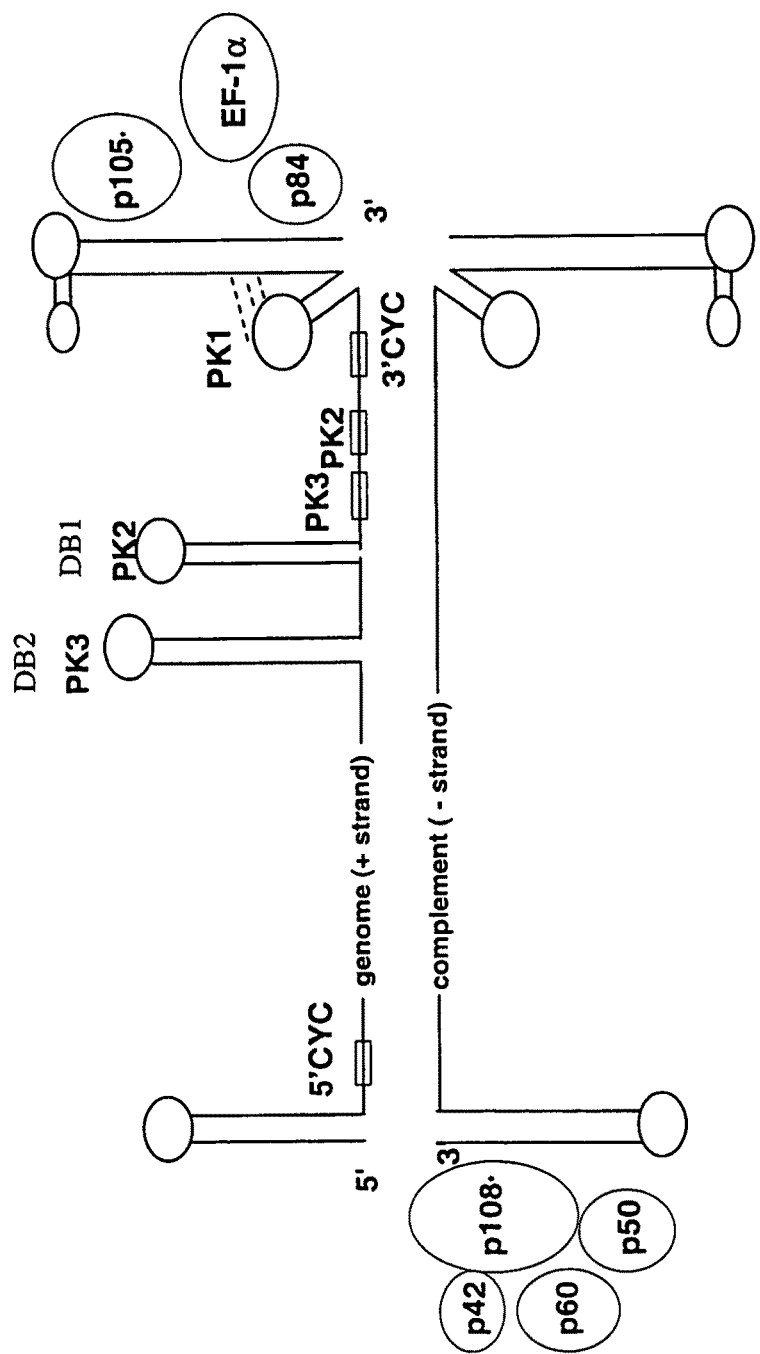
FIG. 7 is a schematic of host proteins interacting with WNV RNA.

The non-coding regions (NCRs) of the flavivirus genome contain terminal RNA structures that are conserved between divergent flaviviruses even though only short sequences in these regions are conserved (8, 9, 27, 36). The terminal RNA structures located at the 3' ends of the genome and complementary minus strand RNAs differ from each other in shape and size. Deletion or mutation of either 3' terminal structure in flavivirus infectious clones resulted in no progeny virus production and indicated that these regions were essential for virus replication (31, 45). However, specific cis-acting signal sequences within these structures have not yet been mapped nor functionally analyzed. The WNV 3' terminal RNA plus strand and minus strand RNA structures have previously been reported to bind specifically to different sets of cell proteins (3, 37; FIG. 7).

The present invention comprises methods and compositions that are effective in modifying the activity or interactions of components or proteins involved in the initiation and regulation of nascent genome RNA synthesis from the minus strand template, nascent minus strand RNA from the genome template, as well as translation of the viral RNA into protein and production of mature proteins for the virus. As used herein, inhibition or interference in viral replication means any change in the rate of viral replication or in the amount of viral components made after infection of a cell by a virus. The change is preferably a decrease in rate or amount of replication, though inhibiting or interfering at one step of the replication pathway may lead to an increase in the precursors necessary for that step.

The presence in solution of the 3' terminal structure of the WNV genomic (plus strand) RNA [WNV 3' (+) SL RNA] was previously confirmed by RNase structure probing (47). Three RNA-protein complexes (RPCs) were detected by gel shift mobility assays performed with Baby Hamster Kidney cell (BHK) cytoplasmic extracts and the WNV 3' (−) SL (stem loop) RNA probe (3). The same pattern of RNA-protein complexes was observed when WNV-infected or uninfected BHK S100 cytoplasmic cell extracts were used, suggesting that the proteins in these complexes were cellular proteins. The results of UV-induced crosslinking and Northwestern blotting studies indicated that the molecular masses of the RNA binding proteins in these complexes were 52, 84, and 105 kDa (FIG. 7). The specificity of these RNA-protein interactions was demonstrated by competition gel mobility shift and competition UV-induced cross-linking assays (3). The p52 protein was identified as EF-1α (46).

The present invention comprises compositions that are effective in prohibiting or interfering with the interactions of host cell proteins, particularly p52, p84 and p105, that are involved in viral replication and particularly with the interactions of these proteins with the WNV 3' (+) SL RNA. Methods of assaying for such compositions comprise adding compositions to cells infected with WNV, or cell-free systems, and measuring the reduction in viral replication, compared to infected cells or cell-free systems without the composition. An embodiment of the invention comprises adding a composition comprising a nucleic acid fragment that mimics the 3' (+) SL RNA in an amount effective to inhibit or interfere with viral replication.

The presence in solution of the 3' terminal structure of the WNV minus-strand RNA [WNV 3' (−) SL RNA] was previously confirmed by RNase structure probing (37). Three RNA-protein complexes (RPCs) were detected by gel shift mobility assays performed with BHK cytoplasmic extracts and the WNV 3' (−) SL RNA probe (37). The same pattern of RNA-protein complexes was observed when WNV-infected or uninfected BHK S100 cytoplasmic cell extracts were used, suggesting that the proteins in these complexes were cellular proteins. UV-induced crosslinking studies indicated that the molecular masses of the RNA binding proteins in these complexes were 42, 50, 60, and 108 kDa (FIG. 7). The specificity of these RNA-protein interactions was demonstrated by competition gel mobility shift and competition UV-induced cross-linking assays (37). p42 has been identified as TIAR/TIA-1.

FIG. 7 is a schematic drawing showing the conserved structures and sequences in WNV RNAs and the cell proteins that bind specifically to the 3' terminal regions of these RNAs. Top line—the WNV genomic RNA; Bottom line—the complementary minus strand RNA; PK—pseudoknot; DB—dumbbell shaped RNA structures; cell proteins are indicated by circles. Competition gel mobility shift data suggest that p108 and p105 are the same protein.

The present invention comprises compositions that are effective in prohibiting or interfering with the interactions of host cell proteins, particularly p42 (TIAR/TIA-1), p50, p60, and p108, that are involved in viral replication and particularly with the interactions of these proteins with the WNV 3' (−) SL RNA. Methods of assaying for such compositions comprise adding compositions to cells infected with WNV, or cell-free systems, and measuring the reduction in viral replication, compared to infected cells or cell-free systems without the composition. An embodiment of the invention comprises adding a composition comprising a nucleic acid fragment that mimics the 3' (−) SL RNA in an amount effective to inhibit or interfere with viral replication.

An embodiment of the present invention comprises methods for identification of one of the WNV 3' (−) SL RNA-binding proteins, p42, as T-cell intracellular antigen-related (TIAR) protein. The closely related protein, T-cell intracellular antigen-1 (TIA-1), was also shown to bind specifically to the WNV 3' (−) SL RNA. Results from WNV growth studies in TIAR-knockout and TIA-1-knockout cells show these cell proteins are important in flavivirus replication. Such knock-out cells are also useful in assays for determining compositions that are effective in inhibiting flavivirus replication. For example, viral infections in knock-out cells for particular host proteins are useful for confirming the effects of selected compositions that are specific for interfering with one or more host proteins involved in viral replication. An embodiment of an assay comprises infecting knock-out cells, for example, cells lacking TIAR, with WNV, adding the composition being tested to one set of cells and not adding the composition to the control set of cells, and comparing the viral replication in the set of knock-out cells with the composition to the control set. Initial comparisons would be made in infected cells that were normal for the protein lacking in the knock-out cells.

A method of the present invention comprises inhibiting replication of a virus, comprising, administering a composition capable of inhibiting at least one host cell protein needed for replication of a virus, preferable wherein the virus is a flavivirus, more preferably wherein the flavivirus is West Nile Virus. Methods include inhibition of at least on host cell, preferably wherein the at least one host cell protein is selected from the group consisting of TIAR/TIA-1, p 52, p84, p105, p108, p42, p 50, or p60. Compositions used in such methods include composition comprising a nucleic acid construct, and include nucleic acid constructs that mimic the 3' end of the negative strand nucleic acid of a flavivirus or that mimic the 3' end of the plus strand nucleic acid of a flavivirus. As used herein, mimicking a nucleic acid means having a nucleotide sequence that is identical to the nucleic acid or has sufficient sequence homology to the nucleic acid such that the mimicking nucleic acid has the same protein interactions or nucleic acid function as the original nucleic acid. Mimicking includes nucleic acid sequences or other molecules or synthetic materials that have the same structure as the original nucleic acid. The original nucleic acid, the one that is being mimicked, can be a fragment of a nucleic acid that includes the end nucleotides or any polynucleotide found between the ends. The original nucleic acid may comprise the sequence of known organisms, or have homology to known organism sequences, or may comprise derived sequences. For example, the nucleic acid sequence may be the sequence of a flavivirus, particularly West Nile Virus. The compositions may comprise a small organic molecule, antibody, peptide, peptoid, or polynucleotide.

Embodiments of the present invention comprise assays for determining compositions that are effective in inhibiting or interfering with viral replication. One assay for determining compositions that inhibit viral replication, comprise, a) adding a composition to cells infected with a virus, and b) comparing the change in viral replication to the cells of a) to control cells infected with the virus. The change in viral replication can be any measurable change the viral replication including, but not limited to, a change in the rate of replication of the virus or a change in the amount of viral components synthesized. One embodiment comprises assays that determine compositions that are effective in inhibiting flavivirus replication, particularly West Nile virus. Another embodiment comprises assays wherein the cells are knockout cells, such as the cells described herein. Knockout cells can comprise cells lacking one or more nucleic acid sequences or proteins, particularly host cell proteins including but not limited to, TIAR/TIA-1, p 52, p84, p105, p108, p42, p 50, or p60.

Methods of the present invention also comprise methods for treating a viral infection, comprising, administering to a human or animal having a viral infection, a composition that alters the interaction of one or more host cell proteins with a viral nucleic acid in an amount effective to inhibit or interfere with viral replication. The compositions comprise those taught herein, including but not limited to, a nucleic acid construct, a small molecule, an antibody, a peptide, peptoid or polynucleotide. The host cell proteins effected include but are not limited to, TIAR/TIA-1, p 52, p84, p105, p108, p42, p 50, or p60. Treatments include treatment of flaviviruses, particularly West Nile virus.

Using methods disclosed herein, p42, one of the four cell proteins previously reported to bind specifically to the WNV 3' (−) SL RNA, has been identified as TIAR/TIA-1. The methods can also be used to identify the other host cells involved in viral replication. It is the inventor's novel finding of the identification of a host protein that interacts specifically with the 3' SL of a flavivirus minus-strand RNA, the site of initiation for nascent genome RNA synthesis. TIA-1 and TIAR are closely related, multifunctional, RNA-binding proteins (20, 40) that have at least partial redundancy in their cellular functions (33). The data herein shows that the binding of TIAR to the WNV 3' (−) SL RNA is functionally important for viral replication.

TIAR and TIA-1 are evolutionarily conserved proteins; homologs in different mammalian species share 96% (TIA-1) and 99% (TIAR) identity (1), while homologs in divergent species such as Drosophila (6, 23) and Caenorhabditis elegans (44) each share about 46% amino acid identity with human TIA-1 and TIAR. Because flaviviruses replicate efficiently in a large number of divergent host species and cycle between invertebrate and vertebrate hosts during their natural transmission cycles, it is expected that these viruses would need to interact with evolutionarily conserved cell proteins to replicate efficiently in different hosts. TIAR and TIA-1 proteins were initially discovered in T cells, hence their name, but have since been found to be expressed in good quantities in many tissues including brain, spleen and macrophages (1), which are sites of flaviviruses replication in vivo.

The present invention is not limited to inhibition or interference with just flavivirus replication, but contemplates the inhibition or interference of other viruses that use host proteins, particularly host proteins that bind to nucleic acids, more particularly host proteins that bind to viral RNAs, and are also not limited to interference or inhibition in any particular species of cells. Thus for example, for proteins that are conserved among species, compositions that are effective in inhibiting the activity of one or both TIAR or TIA-1 of one host species, such as human cells, are effective in inhibiting the replication of the viruses requiring TIAR or TIA-1 in other host species, such as birds or insects Both TIAR and TIA-1 shuttle between the nucleus and the cytoplasm in viable cells. Flaviviruses replicate exclusively in the cytoplasm. Interestingly, the level of TIAR in the cytoplasm of BHK cells is about 10 times higher than in several mouse embryofibroblast cell lines and WNV grows to about 10 times higher titers (peak titer of about $10^{7.5}$ PFU/ml) in BHK cells than in the mouse cell lines (peak titer of about $10^{6.5}$ PFU/ml).

In selection/amplification experiments with pools of randomized RNAs, both TIAR and TIA-1 bound with high affinity to RNAs that contained one or more short sequences of poly U with a dissociation constant of about $2\times10^{-8}$ M (15). Replacement of the Us in these RNAs with Cs eliminated the protein-RNA interaction. Although both proteins selected RNAs containing stretches of Us, the RNA sequences selected by TIA-1 were not identical to those selected by TIAR. The RNA recognition motif 2 (RRM2) domains in both proteins mediated specific binding to uridylate-rich RNAs. However, the presence of the other two RRM domains increased the affinity of the interaction of the proteins with the U-rich RNAs (15).

In the 3' NCR of the TNF-α mRNA, a large fragment of AU-rich sequence containing clustered AUUUA pentamers was required for TIAR/TIA-1 binding (18, 33). The data presented here indicate that both TIAR and TIA-1 can also bind specifically to the WNV 3' (−) SL RNA and that the RRM2 domain mediates this interaction. Since poly U competed efficiently with the WNV 3' (−) SL RNA in the competition gel-mobility shift assays (FIG. 3), it is expected that the viral sequence(s) recognized by TIAR and TIA-1 contains Us. Although the WNV 3' (−) SL RNA is not AU-rich, two of the single stranded loops in this structure contain the sequences, UAAU and UUAAU. These sequences are conserved in single stranded loops in the SLs of other mosquito borne flaviviruses. Mapping studies are underway to identify the individual nucleotides in the WNV 3' (−) RNA required for binding by each of these proteins.

The observed dissociation constant ($K_d$) for the interaction between TIAR RRM2 and the WNV 3' (−) SL RNA was $1.5\times10^{-8}$ M, which is similar to the $K_d$ reported for the interaction between TIAR and U-rich synthetic RNA sequences (and also for other functionally relevant RNA-protein interactions, such as the interaction between the cellular U1A protein and the U1-RNA) (19). Interestingly, the binding activity of TIA-1 ($K_d$ of $1\times10^{-7}$ M) for the WNV 3' (−) SL RNA was about 10 times lower than that of TIAR. Comparison of the RRM2 domain sequences of TIA-1 and TIAR indicate that they differ at eight amino acid residues and that TIAR also contains an eleven amino acid deletion at the beginning of RRM2 (1). The ten fold lower binding activity of TIA-1 for the WNV 3' (−) SL RNA would be expected to result in TIAR out-competing TIA-1 for binding to the viral RNA affinity column and would reduce the likelihood of detecting unique TIA-1 peptides in the protein eluted from the viral RNA affinity column.

A number of cellular functions have been attributed to the RNA binding properties of TIA-1/TIAR. Both TIAR and TIA-1 regulate the generalized translational arrest that occurs following an environmental stress. Stress-induced phosphorylation of the translation initiation factor eIF-2[α is followed by recruitment of poly (A)+ RNA into cytoplasmic stress granules by TIAR and TIA-1 (22). Stress granules and polysomes appear to be in equilibrium in cells (21). TIA-1/TIAR also function as specific translational silencers (18, 33). For example, TNF-α translation is blocked by the binding of TIAR and TIA-1 to specific U-rich sequences in the 3' NCR of this mRNA. Upon stimulation with lipopolysaccharides (LPS), this translational repression is overcome by the binding of an additional protein, p55, to the 3' NCR of the TNF-α mRNA (26). TIA-1 and TIAR have recently been shown to function as alternative splicing regulators by binding to specific U-rich intron (IAS1) sequences adjacent to cryptic 5' splice sites and enhancing the use of these 5' splice sites (14, 25). Such intron sequences exist in a subset of pre-mRNAs, including those of TIA-1 and TIAR, and it is thought that both proteins can regulate their own expression at the level of splicing as well as the expression of some other proteins (16). The yeast protein, Nam8p, a component of the U1 snRNP, is distantly related to TIA-1 and TIAR. It is interesting to note that even though the majority of the known cellular functions of TIAR and TIA-1 involve interactions with cellular mRNAs, it is the 3' terminal region of the WNV minus strand, not the positive strand genome, that interacts with these proteins.

Although both TIAR and TIA-1 have previously been implicated as effectors of apoptotic cell death, the specific roles of these proteins in apoptosis have not as yet been delineated. Introduction of purified TIAR or TIA-1 into the cytoplasm of thymocytes permeabilized with digitonin resulted in fragmentation of genomic DNA into nucleosome-sized oligomers (20, 40). Increased amounts of TIAR were translocated from the nucleus to the cytoplasm in response to exogenous triggers of apoptosis (39). TIA-1 was shown to be phosphorylated by a serine/threonine kinase activated during Fas-mediated apoptosis (41). Although not rigorously tested, no evidence of apoptosis was observed when rodent cells infected with WNV were examined at intervals up to 32 hr post infection after fixation and nuclear staining with Hoerchst dye (data not shown). A study with WNV indicated that apoptosis occurred by 72 hr in infected human mononuclear (K562) cells and mouse neuroblastoma (Neuro 2a) cells via the BAX pathway (32).

Both TIAR and TIA-1 appear to play important roles in embryo development. However, the specific functions of these proteins during development are not known. It was not possible to produce double knock-out mice because of lethality prior to embryonic day 8 (Kedersha and Anderson, unpublished data).

Interestingly, of the five types of the viruses tested in the TIAR and TIA-1 knock-out cells, only the growth of the flavivirus, WNV, was decreased in cells lacking TIAR. In contrast, the growth of the four other types of viruses was more efficient in one or both types of knock-out cells as compared to that in wild type cells. These data suggest that in the wild type cells, one or both of these proteins have a negative effect on the production of these viruses. However, the negative effect that the loss of TIAR and to a lesser extent the loss of TIA-1 have on WNV replication suggests that these proteins provide a necessary function for WNV during its replication cycle.

Though not wishing to be bound by any particular theory, one possible explanation for why the growth of WNV was not reduced to a greater extent in TIAR-knockout cells could be that the TIA-1 protein, which is present in increased amounts in the TIAR-knockout cells (FIG. 6), can substitute for TIAR by providing the function needed by the WNV. However, WNV replication in cells lacking TIAR was never as efficient as when TIAR was present. Also, although the efficiency of virus replication increased when TIAR-knockout cells were reconstituted with vector expressed TIAR (FIGS. 5 and 6), neither the amount of TIAR nor WNV replication reached wild type levels in these reconstituted cells.

The only known function of the flavivirus minus strand RNA is as a template for the synthesis of nascent genomic RNA. Specific binding of TIA-1/TIAR to the 3' terminus of the viral minus strand RNA template appears to play a positive role in virus replication. Possible functions of this interaction include assisting in the formation or stabilization the 3' terminal (−) SL and/or in the recognition of the minus template by the polymerase.

Whether the ability of TIA-1/TIAR to associate with stress granules is utilized by flaviviruses and/or the other types of viruses tested is not known. Flavivirus infections do not shut off host cell translation (27) and flaviviral nonstructural proteins and dsRNA (indicative of viral replication intermediates) have been co-localized to redistributed endoplasmic reticulum, trans-Golgi and intermediate compartment membranes (29, 30). Nevertheless, further studies are needed to investigate whether stress granules are present in flavivirus infected cells and if so, whether they are associated with viral replication complexes. If the binding of TIA-1/TIAR to viral minus strand RNAs in replicative intermediates results in their co-localization with stress granules, this would provide an environment in which the translation of growing nascent viral plus strand RNAs would be inhibited. Alternatively, the binding of TIA-1/TIAR by the viral RNA could keep it from caring out its normal cell functions during stress.

Though not wishing to be bound by any particular theory, it is believed that TIAR/TIA-1 may have several roles in viral replication, one role is in enhancing WNV replication by acting as transcription factors for plus strand synthesis. Another role involves stress granule formation. TIAR/TIA-1 form compartments much like stress granules that sequester viral plus strand RNA synthesis, so that translation of nascent plus strands into protein is inhibited. Another function is the inhibition of formation of stress granules by the cell in response to infection by a virus, which would prevent the shut off of cell protein translation and lead to a delay in the onset of apoptosis in the cells. Interference with the activity of TIAR/TIA-1 by the compositions of the present invention results in decreased synthesis of genome RNA, results in the shut off of cell protein synthesis and leads to the onset of apoptosis. The ability to affect the onset of apoptosis or to delay apoptosis can be applied to many disease states and treatments of such diseases by providing compositions that are effective in delaying or initiating apoptosis are contemplated by the present invention.

Compositions contemplated by the present invention include compounds capable of inhibiting viral replication, preferably by inhibiting the activity of host cell proteins involved in viral replication. Such compounds are capable of inhibiting the activity of host cell proteins in vitro and in vivo and show antiviral activity both in vitro and in vivo. In addition, the compositions of the present invention are capable of inhibiting the activity of host cell proteins without detrimentally affecting cellular viability.

One aspect of the present invention comprises administration of compositions comprising compounds such as nucleic acid constructs. For example, a nucleic acid construct can be a DNA molecule that is transcribed by the host cells to form decoy RNA molecules. The decoy RNA molecules then compete with the binding of host proteins, for example TIAR/TIA-1, to viral 3' RNA. Other preferred compounds include RNA molecules, small organic molecules, antibodies, peptides, peptoid, or polynucleotides that interfere with the binding of host proteins, for example TIAR/TIA-1, to the viral 3' RNA. An alternative method of administration comprises administration of compositions of decoy RNA made in vitro. Routes of administration comprise those known in the art, though preferably such compositions are delivered via injection or intranasal methods. Preferably, the decoy RNA comprises modified ribonucleic acid nucleosides that provide stability and resistance to nucleases. For example, 2-O-methyl RNA is very stable and is readily taken up by cells and is used for clinical applications. The present invention contemplates this and other modified RNAs.

The present invention comprises compositions and methods for inhibiting replication of flavivirus. The present invention comprises methods and compositions for inhibiting West Nile Virus replication. An aspect of the invention comprises providing interfering RNA sequences that bind host cell proteins. Such host cell proteins are host cell proteins, proteins that are not encoded by the viral genetic sequence such as TIA-1 and TIAR, that bind to the RNA minus strand of the virus.

An aspect of the invention comprises RNA sequences that bind host cell proteins, wherein the RNA sequences have a structure having two loops, closely spaced to each other, having UAAU, AAAA or UUUU sequences therein. RNA sequences having closely spaced loops are effective for binding host cell proteins and may be useful for inhibiting replication of the flavivirus, such as West Nile Virus (WNV). An aspect of the invention comprises compositions comprising an RNA sequence comprising two loop structures, in close relation with each other, wherein at least one loop has an UAAU, AAAA or UUUU sequence. RNA sequences having two loops that are in close relation with each other such as loops within 4-10 base pairs from each other, within 3-8 base pairs from each other, within 4-6 base pairs from each other, within 4 base pairs from each other, within 5 base pairs from each other, within 6 base pairs from each other, within 7 base pairs from each other, within 8 base pairs from each other, within 9 base pairs from each other, within 10 base pairs from each other, as shown by two dimensional mapping programs, are contemplated by the present invention.

RNA sequences that can form two loop structures within close relation to each other, at least within 3-10 base pairs, and wherein at least one loop, wherein at least two loops, contain sequences UAAU, AAAA or UUUU are contemplated by the present invention. Such sequences include the 3' terminal 75 nucleotides of the WNV minus-strand RNA, SEQ ID NO. 3. Compositions and methods of the present invention comprise SEQ ID NO. 3, SEQ ID NO. 4, SEQ ID NO.8, SEQ ID NO. 11, SEQ ID NO. 18, SEQ ID NO. 19, and SEQ ID NOs. 20-23. Other sequences of the present invention comprise SEQ ID NOs. 35-38, SEQ ID NOs.40-47, 49, 50-53.

Other RNA sequences that may be used in the present invention comprise SEQ ID NOs. 5-7, 9, 10, 12, 14, 15, and 27. RNA sequences that bind one host cell protein more effectively than another host cell protein are also contemplated by the present invention. For example, SEQ ID NO. 13 will bind TIAR, but not TIA-1. RNA sequences that bind either TIA-1 or TIAR or both proteins more effectively than wild-type minus strand 3' end RNA are also contemplated by the present invention and compositions and methods comprise, but are not limited to, SEQ ID NO. 24-26 for both TIA-1 and TIAR, and SEQ ID NO. 20-23 for TIA-1. SEQ ID NO. 20-23 also bind TIAR effectively.

Sequences taught herein may be truncated to comprise the binding regions for TIA-1 and TIAR that comprise the two loop structures, wherein at least one loop has UAAU, AAAA or UUUU sequence therein. Compositions and methods comprise use of RNA sequences comprising less than 75 nucleotides of the 3' end of the minus strand of WNV, including the sequences taught herein. Compositions of the present invention for binding of host cell proteins TIA-1 and/or TIAR comprise sequences having at least nucleotides 14-61 of SEQ ID NO. 3 and the mutations and deletions of that sequence taught herein, such as SEQ ID NOs. 4, 8, 11, 18, 19, 20-23, and others including SEQ ID NOs. 35-38, 40-47, 49, 50-53, 5-7, 9, 10, 12, 14, 15, 27, 20-23, and 24-26. Sequences for the present invention comprise those taught herein with nucleotides 1-13 deleted and/or 62-75 deleted. Sequences remaining after deletion, such as nucleotides 14-61, may be incorporated into vectors or other nucleotide sequences, such as other RNA sequences. Vectors may include viral vectors or other known methods of delivery of RNA sequences. The present invention contemplates delivery of RNA sequences in vitro and in vivo.

Methods of the present invention comprise binding host cell proteins, such as TIA-1 and TIAR by providing RNA sequences comprising two closely spaced loops having UAAU, AAAA or UUUU sequences therein. Such an RNA structure effectively binds the host cell proteins, such as TIA-1 and TIAR, and prevents such host proteins from participation in the replication of WNV. Methods for inhibiting flavivirus, such as WNV, comprise providing an RNA sequence and structure capable of binding TIA-1 and TIAR. Interference with the binding of TIA-1 and/or TIAR to the WNV minus strand interferes or inhibits the replication of WNV. RNA sequences having the structure and sequences to which the host proteins TIA-1 and TIAR bind include but are not limited to SEQ ID NOs. 3, 4, 8, 11, 18, 19, 20-23, and others including SEQ ID NOs. 35-38, 40-47, 49, 50-53, 5-7, 9, 10, 12, 14, 15, 27, 20-23, and 24-26.

The present invention comprises a mutant WNV, wherein the viral positive strand codes for a sequence wherein the RNA minus strand has a sequence such that the minus strand 3' terminal 75 nucleotides comprise one of SEQ ID NOs. 4-27, 32-53, 56 or 57. Such sequences and viruses are taught herein.

Although first discovered in T cells, T-cell intracellular antigen-1 (TIA-1) (Anderson et al., 1990) and T-cell intracellular antigen related protein (TIAR) (Kawakami et al., 1992) are expressed in most types of cells and tissues (Beck et al., 1996; Jin et al., 2000). Both proteins are found in the cytoplasm and nucleus and shuttle between these two compartments. These evolutionarily conserved, multifunctional cellular proteins have been reported to regulate alternative splicing (Dirksen et al., 2003; Yu et al., 2003; Zhu et al., 2003; Shukla et al., 2004; Shukla et al., 2005) or translation (Piecyk et al., 2000; Dixon et al., 2003; Kandasamy et al., 2005) of a subset of mRNAs; to play a regulatory role in Fas-mediated apoptosis (Taupin et al., 1995; Tian et al., 1995; Li et al., 2004); and to sequester cytoplasmic mRNAs into stress granules (Kedersha et al., 1999; Kedersha et al., 2000). Both proteins were shown to be essential for embryonic development (Beck et al., 1998; Piecyk et al., 2000). The lack of TIA-1 or TIAR in mice results in embryonic lethality in a strain dependent manner. BALB/c mice lacking TIAR showed a 100% embryonic lethality whereas C57BL/6 mice showed 90% embryonic lethality. In TIA-1 deficient mice of both strains the rate of embryonic lethality was 50% (Piecyk et al., 2000). Attempts to knock out both proteins in mice were unsuccessful (Piecyk et al., 2000). Suppression of both TIA-1 and TIAR in DT40 chicken cells resulted in cell death (Le Guiner et al., 2003).

TIA-1 and TIAR are members of the RNA recognition motif (RRM) family of RNA binding protein (Anderson, 1995). Both proteins contain three N-terminal RRMs and a C-terminal glutamine-rich auxiliary domain (Tian et al., 1991; Kawakami et al., 1992). The C-terminal domain was reported to be structurally similar to the prion protein (Tian et al., 1991; Kawakami et al., 1992). TIA-1 and TIAR share 80% overall amino acid (aa) identity with the highest degree of similarity (91% identity) in the third RRM and the lowest degree of similarity (51% identity) in the C-terminal domain (Kawakami et al., 1992; Anderson, 1995; Beck et al., 1996). RRM2 was sufficient for specific binding of either protein to uridylate-rich RNA. RRM1 and RRM3 enhanced RRM2 RNA binding (Dember et al., 1996). In somatic cells, RRM2 and the first half of the C-terminal domain mediate TIA-1 and TIAR nuclear accumulation, whereas RRM3 facilitates their nuclear export (Zhang et al., 2005).

The two isoforms of both TIA-1 and TIAR are translated from alternatively spliced mRNAs (Beck et al., 1996). The TIA-1 isoforms differ by the presence (TIA-1a) or absence (TIA-1b) of a mini exon encoding 11 aa within RRM1. TIARa includes a mini exon that encodes 17 aa within RRM1, whereas TIARb lacks this exon. The molecular masses of the long isoforms of both proteins are ~42 kDa, whereas those of the short isoforms are ~40 kDa (Beck et al., 1996). The two TIA-1 isoforms are equally abundant in cells, while the short isoform of TIAR is 6 times more abundant than the long isoform (Beck et al., 1996).

TIA-1 and TIAR proteins were previously reported to bind specifically to AU-rich regions in the 3' noncoding region (NCR) of a subset of cellular mRNAs, including TNF-α (Gueydan et al., 1999; Piecyk et al., 2000), cyclooxgenase-2 (COX-2) (Dixon et al., 2003; Cok et al., 2004), and $β_2$-adrenegic receptor ($β_2$-AR) (Kandasamy et al., 2005) mRNAs. The minimal sequence required for TIAR binding was mapped to 39 AU nts in the 3' NCR of the TNF-α mRNA (Lewis et al., 1998; Gueydan et al., 1999).

West Nile Virus (WNV) is a member of the family Flaviviridae, genus flavivirus (Lindenbach and Rice, 2001). The WNV genome is a single-stranded RNA of positive polarity that is approximately 11 Kb in length (Rice et al., 1985). The genome contains a single, long open reading frame (ORF) encoding a polyprotein that is co- and post-translationally processed by viral and cellular proteases into three structural proteins and seven nonstructural proteins (Chambers et al., 1990). During the flavivirus replication cycle, which takes place in the cytoplasm of infected cells, the genomic RNA serves as the only viral mRNA and is also the template for transcription of complementary minus-strand RNA. The viral minus-strand RNA in turn serves as a template for the synthesis of genomic RNA (Brinton, 2002). The terminal 5' and 3' NCRs of the WNV genomic RNA are 96 and 631 nts (nts) in length, respectively (Chambers et al., 1990). Previous studies indicated that both the 3' and 5' terminal nts of the flavivirus genome RNA (Brinton et al., 1986; Brinton and Dispoto, 1988; Chambers et al., 1990) as well as the 3' terminal nts of the complementary minus-strand (Shi et al., 1996) form stem-loop (SL) structures. Deletion or mutation of either of the terminal regions in flavivirus infectious clones was lethal demonstrating that these regions contain essential cis-acting elements for virus replication (Cahr et al., 1995; Men et al., 1996)

Particular host cell proteins have previously been reported to bind specifically to regions within the 3' and 5' NCRs of a number of animal RNA virus genomes (Lai, 1998). The 3'-terminal stem loop structure of the WNV minus-strand RNA [WNV3'(−)SL] binds specifically to hamster cell proteins with molecular masses of about 42, 50, 60, and 108 kDa (Shi et al., 1996). p42 was identified as TIAR and recombinant TIA-1 was also shown to bind to this RNA (Li et al., 2002). Consistent with previous data obtained with the NCRs of cell mRNAs (Dember et al., 1996), the binding of TIA-1 and TIAR to the WNV3'(−)SL RNA is mediated by RRM2 (Li et al., 2002). Kinetic studies indicated that the binding activity of the TIAR RRM2 for the WNV3'(−)SL RNA was 10 times higher than that of the TIA-1 RRM2 for this RNA (Li et al., 2002).

Expression and Purification of Recombinant TIA-1 and TIAR

Although it was previously reported that both TIA-1 and TIAR bind to AU-rich sequences in the 3'NCRs of cell mRNAs (Gueydan et al., 1999; Dixon et al., 2003; Cok et al., 2004; (Kandasamy et al., 2005), these studies did not fine map the RNA binding sequences nor consider the structural context. The WNV3'(−)SL RNA differs from the long (39 nts) "assumed linear" AU-rich sequences shown to bind to TIA-1 and TIAR in cell mRNAs by having a few short single-stranded AU-rich regions and by having the majority of the adjacent bases paired in stems of a secondary structure.

Figure 8:
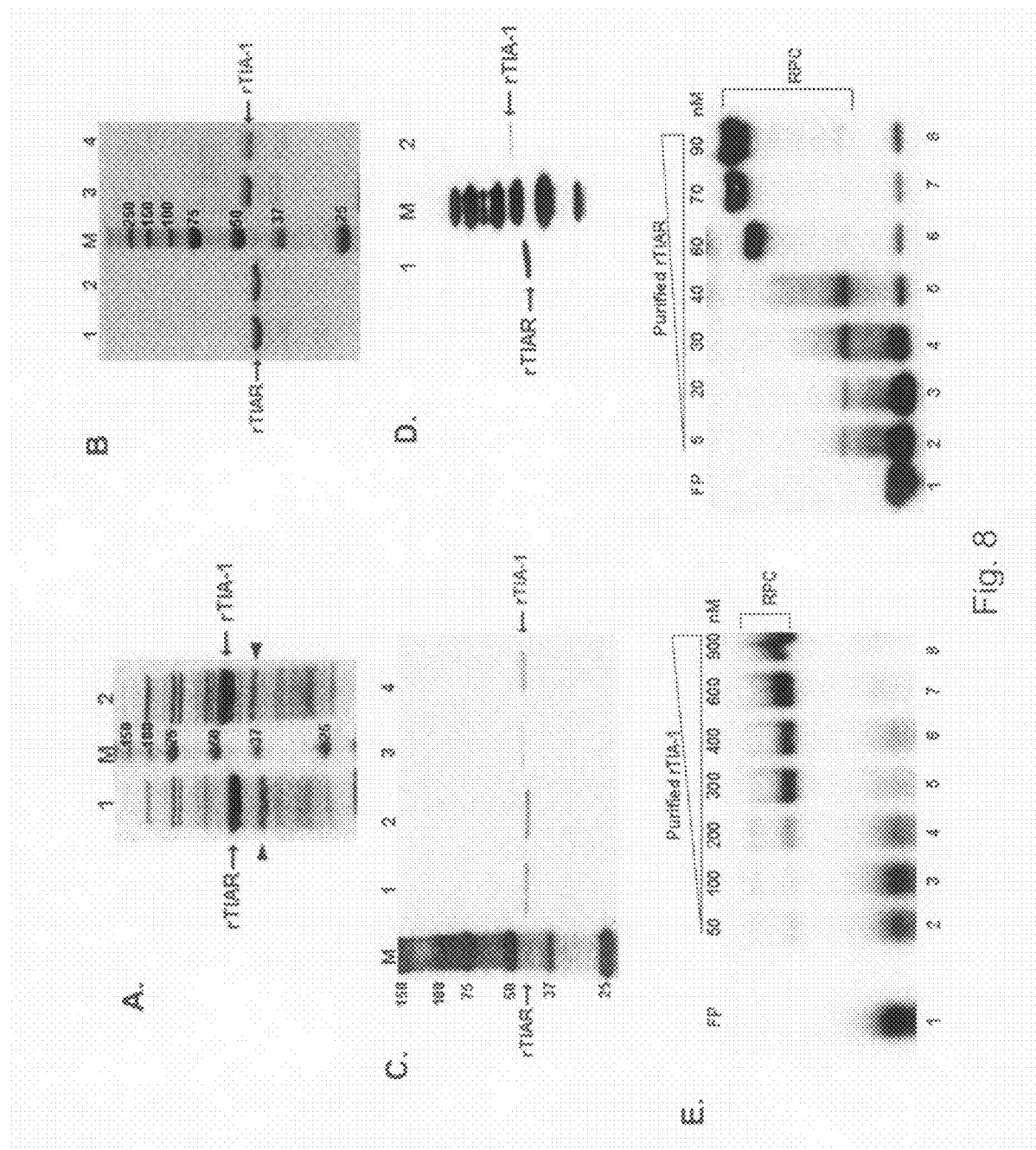
FIG. 8 A-I shows expression, purification, and RNA binding activities of recombinant TIA-1 and TIAR proteins.

Recombinant TIA-1 and TIAR proteins were expressed from a pCRT7/CT-TOPO expression vector in *E. coli* Rosetta cells and purified as described in Examples and then used in gel mobility shift assays with mutant WNV3'(−)SL RNA probes to fine map the binding sites of these proteins. To easily distinguish the two proteins on gels, the longer isoform of TIA-1 and the shorter isoform of TIAR were expressed. A His-tag was added to the C-terminus of both proteins to facilitate their purification. Expressed recombinant proteins of about 47 kDa (rTIA-1) and 45 kDa (rTIAR) were observed in the soluble fractions of induced vector-containing bacterial cell lysates (FIG. 8A). Additional bands of ~36 or 38 kDa were also reproducibly observed (FIG. 8A, arrow heads). The observation of these additional bands was previously reported (Tian et al., 1991; Kawakami et al., 1992; Taupin et al., 1995).

The expressed recombinant proteins were purified by either a one step protocol on a cobalt affinity column (FIG. 8B) or by a two step protocol utilizing an anion exchange column followed by a cobalt column (FIG. 8C) as described in Examples. It was estimated that both recombinant proteins were purified to ~85% and 98% homogeneity by one and two step protocols, respectively. The presence of purified rTIA-1 or rTIAR protein was confirmed by Western blot analysis using protein specific polyclonal antibodies directed against the C-terminus of each protein (FIG. 8D).

RNA Binding Activities of Recombinant TIA-1 and TIAR

The binding activities of the purified recombinant proteins obtained from the two purification protocols were tested by gel mobility shift assay with a WNV3'(−) SL RNA probe as described in Examples. Although RNA-protein complexes (RPC) were formed with the highly purified proteins (~98% homogeneity) and increased with increasing protein concentrations, extensive protein aggregation was observed and much of the protein remained in the wells (data not shown). Partially purified proteins (~85% homogeneity) were therefore used in all subsequent gel mobility shift assays. For rTIAR, binding activity was detected at concentrations as low as 5 nM (FIG. 8E, right panel), whereas for rTIA-1 concentrations of ~50 nM were required to detect binding (FIG. 8E, left panel). This 10-fold difference in binding activity was consistent with data previously reported for GST fusion, recombinant proteins (Li et al., 2002). RNA-protein complex aggregates were observed with both proteins at concentrations of 50 nM or higher (FIG. 8E).

To show the specificity of the interactions between the WNV3'(−)SL RNA (0.2 nM), SEQ ID NO. 3, and the two recombinant proteins, competition gel-shift assays were done. For rTIA-1, a small amount of competition was observed only at 200 fold excess of poly I/C (1.0 ng) (FIG. 8F, lane 7) or 100 molar fold excess of tRNA (20 nM) (FIG. 8G, lane 7), whereas competition was observed with concentrations of unlabeled WNV3'(−)SL RNA as low as 0.2 nM (FIG. 8H). Similar results were observed with rTIAR (data not shown). Two additional nonspecific viral RNA probes, WNV3'(+)SL and WNV5'(+)SL, SEQ ID NO. 31, were also tested as competitors. Neither protein bound to either of these RNA probes (data not shown).

Also, two control proteins, purified BSA and purified recombinant elongation factor 1 alpha (eEF-1α), did not bind to the WNV3'(−)SL RNA in gel mobility shift assays at concentrations of 100, 200, or 600 nM (FIG. 8I). These results demonstrate that the interactions between recombinant TIA-1 and TIAR and the WNV3'(−)SL RNA are specific.

Analysis of the WNV3'(−)SL RNA Structure

Two alternative optimal secondary structures 3'(−)S1 (FIG. 9A) and 3'(−)S2 (FIG. 9B), were predicted for the 3' terminal 75 nts of the WNV minus-strand RNA by M-fold version 3.1 (Zuker, 2003). The minimum free energy values for 3'(−)S1 and 3'(−)S2 were ~15.4 and ~14.6, respectively. The 3(−)S2 structure was similar to that predicted for the first 75 nts of the complementary 5'(+)SL RNA (FIG. 16C) by M-fold on 5'WNV sequences ranging in length from 75 to 3000 nts and by a whole WNV RNA genome (11,022 nts) fold (personal communication, Drs. A. Palmenberg and J.-Y. Sgro, University of Wisconsin Madison). The predicted 3'(−)S1 structure was similar to that obtained in the structure probing study of Shi et al. (1996), in the upper and the lower portions, but differed in the middle part of the structure.

Figure 9:
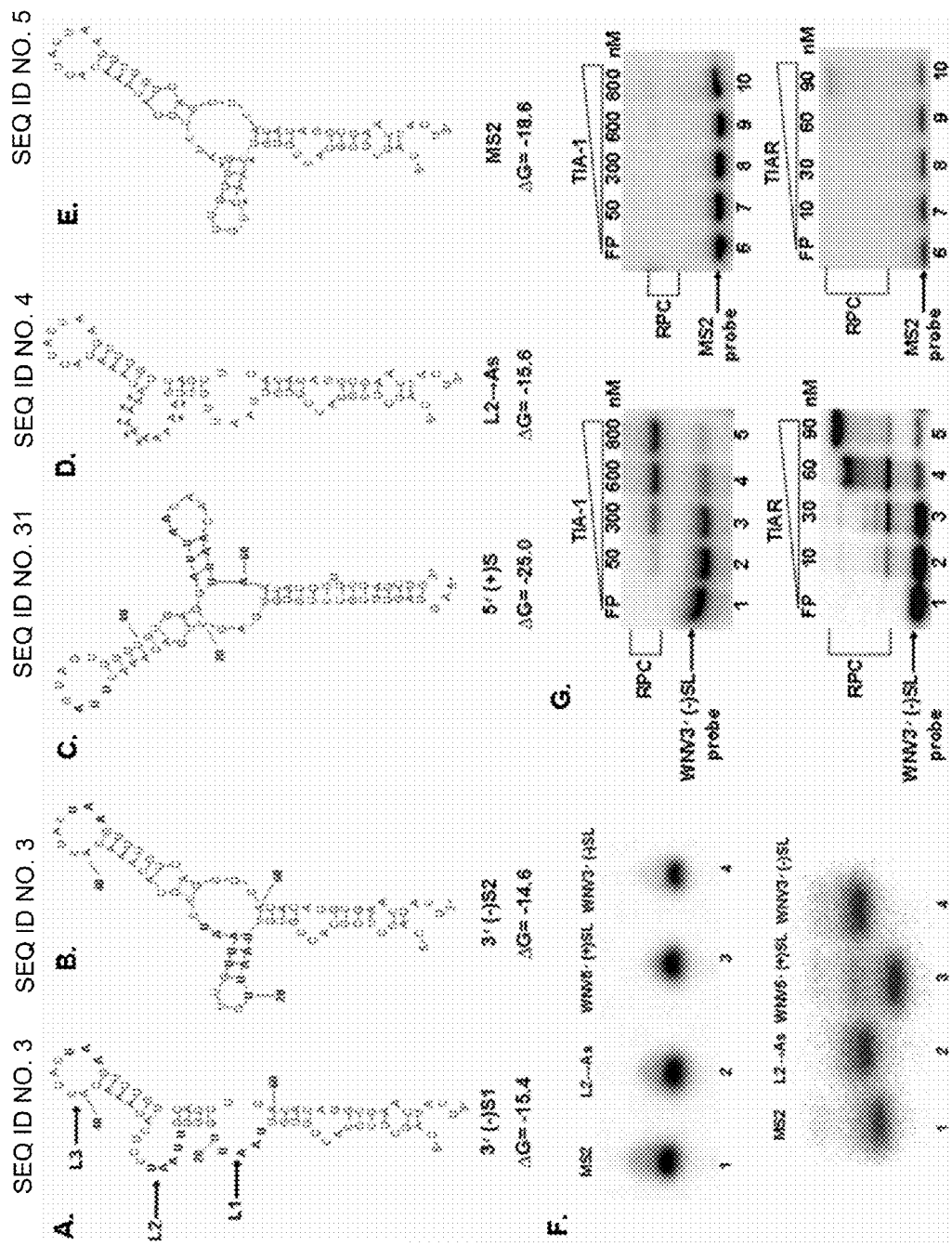
FIG. 9 A-G shows analysis of the WNV3'(−)SL RNA structure.

To show which of the structures predicted for the WNV3'(−)SL RNA was the optimal structure for binding to TIA-1 and TIAR, mutations were introduced to lock the structure into one or the other of the predicted conformations (FIG. 9D SEQ ID NO. 4, and E, SEQ ID NO. 5). A single optimal M-fold secondary structure was predicted for each of these mutant RNAs. The migration of these two mutant RNAs, wild type WNV3'(−)SL RNA, and the complementary WNV5'(+)SL RNA were compared on denaturing and non-denaturing gels. The four RNAs migrated to the same position on a denaturing gel (FIG. 9F, upper panel), but on the non-denaturing gel (FIG. 9F, lower panel), the wild type WNV3'(−)SL RNA and the L2→As RNA migrated to similar positions, while both the WNV5'(+)SL and MS2 RNAs migrated faster.

In gel mobility shift assays, rTIA-1 (FIG. 9G, right upper panel) and rTIAR (FIG. 9G, right lower panel) showed minimal binding to the MS2 probe, SEQ ID NO. 5. In contrast, the wild type RNA (FIG. 9G, left panels) and the L2→As RNA, SEQ ID NO. 4, (see FIG. 14) bound efficiently to both recombinant proteins. Since these results as well as those of Shi et al. (1996) indicated that 3'(−)S1 is the primary secondary structure of the WNV3'(−)SL RNA, this structure was used to design mutant RNAs for mapping the protein binding sites.

Mapping the Binding Sites for the TIA-1 and TIAR Proteins within the WNV3'(−)SL RNA Both TIA-1 and TIAR were previously reported to bind specifically to AU-rich regions in the 3' NCRs of cell mRNAs and a minimal binding sequence of 39 AU nts was mapped for the TNF-α mRNA that contained 7 AUUUA sequences hypothesized to be the protein binding sites (Lewis et al., 1998; Gueydan et al., 1999). In the WNV3'(−)SL RNA, short AU-rich sequences are located in three single-stranded loop regions (L1, L2, and L3; FIG. 9A). To determine whether the TIA-1 and TIAR proteins bind to one or more of these AU-rich sequences, mutations and/or deletions were introduced into each of these loops (FIG. 10A) and the mutant RNAs were used as probes in gel mobility shift assays with the recombinant proteins. AU nts in each loop were first replaced with Cs. These substitutions were at positions 16 to 20 (5'UAAUU3', L1→Cs) SEQ ID NO.6, at positions 26 to 29 (5'UAAU3', L2→Cs) SEQ ID NO. 7, at positions, 40 to 47 (5'ACUACUAA3', L3→Cs) SEQ ID NO. 8, and at positions 16 to 20 plus 26 to 29 (L1+L2→Cs) SEQ ID NO. 9 (FIG. 10A). Mfold analysis indicated that the predicted RNA secondary structure of the wild type RNA was preserved in each of these mutants. The gel shift assays shown in this figure and in all the subsequent figures are representative of three replicate experiments. The binding activities of both recombinant proteins for mutant RNAs L1→Cs and L2→Cs were significantly reduced (FIG. 10B, Lanes 7-10 and 12-15; FIGS. 10C and D) as compared to those for the wild type RNA (FIG. 10B, Lanes 2-5; FIGS. 10C and D). Even less efficient binding was detected with either protein to the L1+L2→Cs RNA (FIG. 10B, Lanes 17-20; FIGS. 10C and D). In contrast, the mutant L3→Cs RNA formed complexes with both proteins (FIG. 10B, lanes 22-25) as efficiently as the wild type RNA (FIGS. 10C and D).

Figure 11:
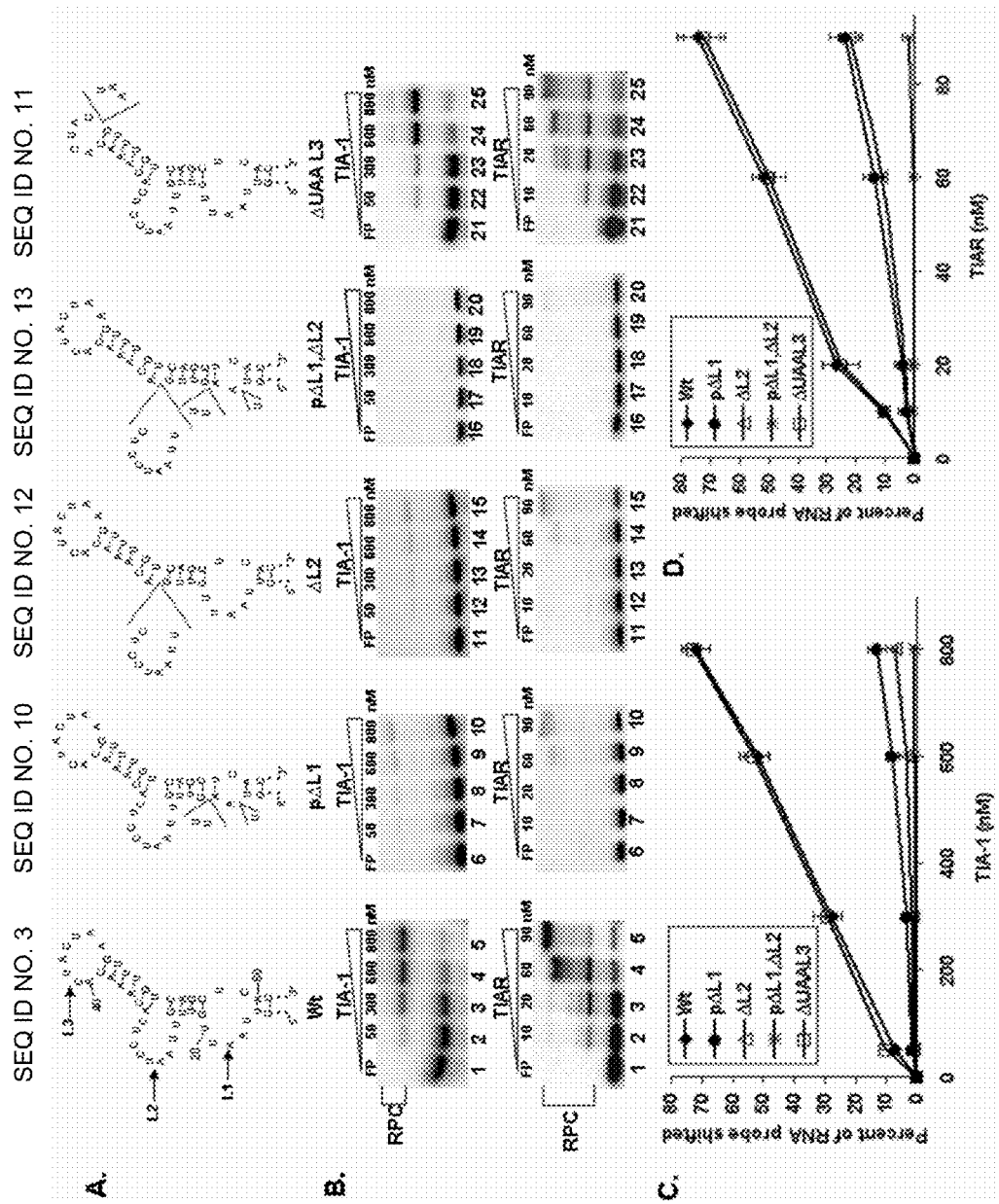
FIG. 11 A-D shows the effect of deletions in L1, L2, or L3 of the WNV3'(−) SL RNA on TIA-1 and TIAR binding activity.

As an alternative strategy, deletions in each loop were made separately or in combination. Only 3 nts could be deleted in L1 (U16, U19, and U20, pΔL1) SEQ ID NO. 10, or in L3 (U45, A46, and A47, ΔUAAL3), SEQ ID NO. 11, without affecting the predicted RNA secondary structure of the WNV3'(−)SL RNA, while all of L2 (ΔL2) SEQ ID NO. 12, could be deleted (FIG. 11A). The reduced binding observed for the pΔL1 and ΔL2 RNAs (FIG. 11B, lanes 7-10 and 12-15; FIGS. 11C and D) was similar to that observed with the L1→Cs and L2→Cs RNAs. No rTIA-1 RNA-protein complexes were detected with the pΔL1, ΔL2 RNA SEQ ID NO. 13, (FIG. 11B, upper panel, lanes 17-20; FIG. 11C) and minimal rTIAR binding was detected with this RNA (FIG. 11B, lower panel, lanes 17-20; FIG. 11D). As observed with the L3→Cs RNA, the binding activities of both proteins for the AUAAL3 RNA were similar to those for wild type RNA (FIG. 11B, lanes 22-25; FIGS. 11C and D). These results showed that the AU-rich sequences in L1 and L2 of the WNV3'(−)SL RNA, but not those in L3, were required for efficient binding of both TIA-1 and TIAR in vitro.

Determination of the Minimum Sequence in Each Loop Required for TIA-1 and TIAR Binding The nts deleted in the pΔL1 and ΔL2 RNAs were next sequentially restored. RNA with U20 restored was designated pΔL1+U, ΔL2 SEQ ID NO. 14, and RNA with both U19 and U20 restored was designated pΔL1+UU, ΔL2 SEQ ID NO. 15 (FIG. 12A). A slight increase in the percent of RNA probe shifted was observed with the restoration of U19 and the restoration of U20 give a further increase for both proteins (FIGS. 12C and D). Sequential restoration of U25, U26, A27, and A28 in the pΔL1, ΔL2 RNA generated pΔL1, ΔL2+U, SEQ ID NO.16, pΔL1, ΔL2+UU, SEQ ID NO. 17, pΔL1, ΔL2+UUA, SEQ ID NO. 18, and pΔL1, ΔL2+UUAA SEQ ID NO. 19, RNAs, respectively (FIG. 12B). No increase in the binding activity of either protein was observed until three nts (5'UUA3') had been restored to the pΔL1, ΔL2 RNA (FIGS. 12E and F). Further increases in the binding activities of both proteins were observed with the pΔL1, ΔL2+UUAA and pΔL1 RNAs (FIGS. 12E and F).

Effect of Substitution of L1 and L2 with As or Us

Both TIA-1 and TIAR were previously reported to bind poly(A) (Tian et al., 1991; Taupin et al., 1995) and poly(U) (Kawakami et al., 1992; Taupin et al., 1995). Although both proteins have a higher binding affinity for poly(U) than for poly(A), TIA-1 binds to poly(A) more efficiently than does TIAR (Kawakami et al., 1992; Taupin et al., 1995). To determine whether increasing the number of As in L1 and L2 preferentially increased the binding of rTIA-1 to the WNV3'(−)SL RNA, the Us in L1, L2, and L3 were replaced with As separately or in combination and the mutant RNAs were tested in binding reactions with both proteins. L1 (5'UAAUU3') was replaced by 5'AAAAC3' to form the L1→As mutant RNA, SEQ ID NO.20. U20 was mutated to a C to preserve the predicted RNA secondary structure. L2 and L3 were replaced separately with As to make RNA mutants L2→As, SEQ ID NO. 21, and L3→As, SEQ ID NO. 22, respectively. The L1+L2→As mutant RNA had As in both L1 and L2, SEQ ID NO.23. None of these mutations altered the predicted RNA secondary structure (FIG. 13A). With rTIAR, similar levels of binding was observed with the wild type, L1→As, L2→As, and L3→As mutant RNAs (FIG. 13B lower panel, lanes 2-5, 7-10, 12-15, and 22-25 and FIG. 13D), but increased binding was observed with the L1+L2→As RNA (FIG. 13B lower panel, lanes 17-20 and FIG. 13D). In contrast, all the mutant RNAs bound more efficiently than the wild type RNA to rTIA-1. The L1+L2→As RNA gave the most efficient binding, while the L3→As, L2→As, and L1→As RNAs showed sequentially reduced binding (FIG. 13B upper panel, lanes 7-10, 12-15, 17-20 and 22-25 and FIG. 13C).

The nts in L1, L2, and L3 were next replaced with Us and the mutant RNAs were designated L1→Us, SEQ ID NO. 24; L2→Us, SEQ ID NO. 25; and L3→Us, SEQ ID NO. 26, respectively. The predicted RNA secondary structure was preserved in all of these mutant RNAs. With both proteins all of the U substitution RNAs bound more efficiently than the wild type RNA with L3→Us RNA giving the highest level of binding. A 4, 11, and 19% increase in the binding activity of rTIAR (60 nM) was observed for L1→Us, L2→Us, and L3→Us mutant RNAs, respectively, as compared to that for wild type RNA (data not shown). The binding activity of rTIA-1 (600 nM) for the L1→Us, L2→Us, and L3→Us mutant RNAs was 10, 23, and 35% higher than for the wild type RNA, respectively (data not shown). These results indicate that either protein can bind to single-stranded A or U tracts in the context of a secondary structure and that TIA-1 binds more efficiently to tracts of As or Us than to a mixture of AU nts.

Figure 10:
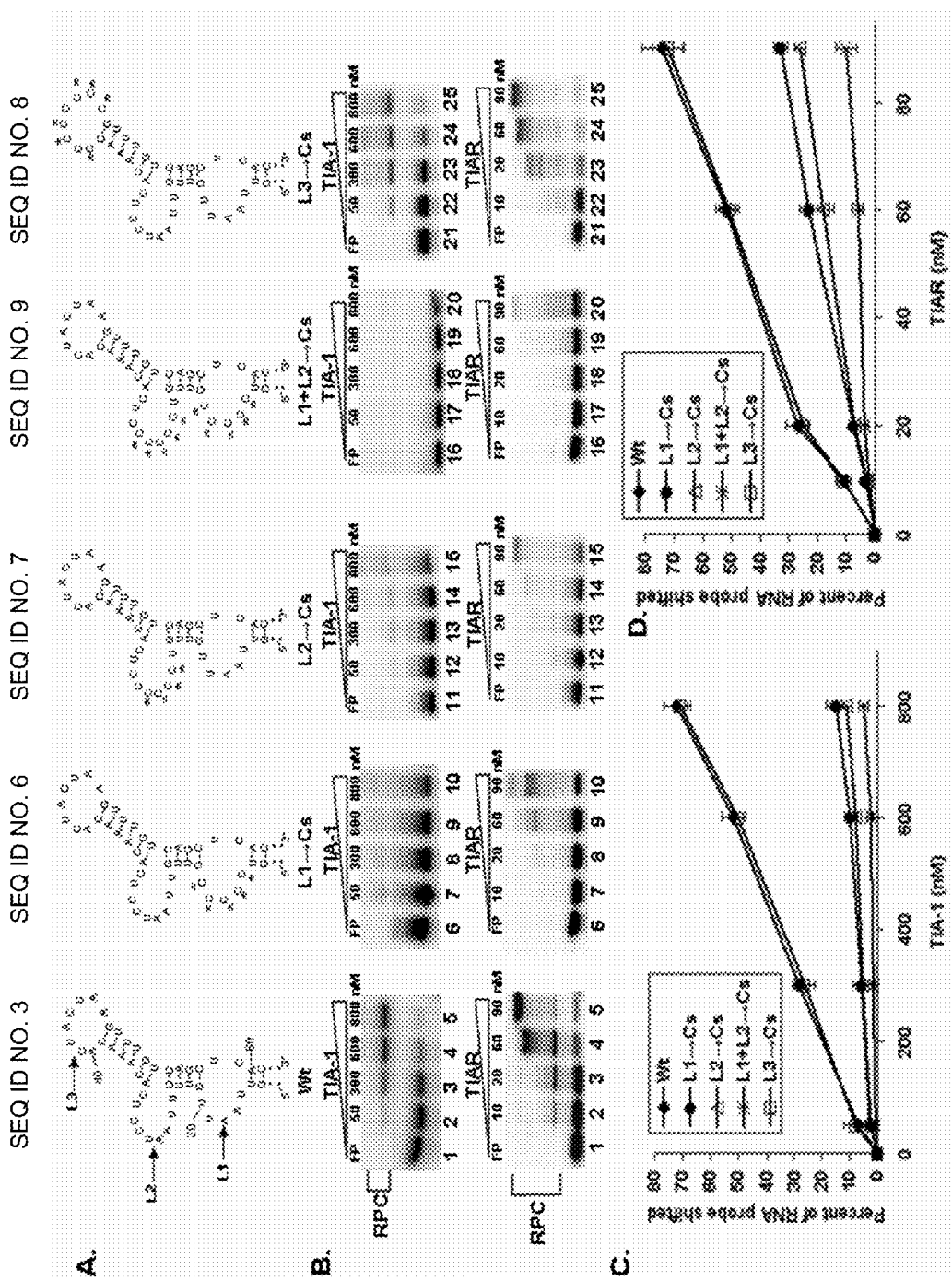
FIG. 10 A-D shows the effect of C substitutions in L1, L2, and L3 of the WNV3'(−)SL RNA on TIA-1 and TIAR binding activity.

Effect of Increasing the Distance Between L1 and L2 on the Binding Activities of TIA-1 and TIAR The mapping above indicated that both L1 and L2 are required for efficient TIA-1 and TIAR binding to the WNV3'(−)SL RNA. In the predicted secondary structure of the WNV3'(−)SL RNA, these two loops are located in a close proximity to each other (FIG. 14A). To determine if the distance between L1 and L2 is important for efficient protein binding, four base pairs were inserted to increase the distance between these two loops (LS RNA). This mutation did not alter the predicted secondary structure of the WNV3'(−)SL RNA (FIG. 14A). The LS RNA SEQ ID NO. 27, bound significantly less efficiently to both proteins (FIG. 14B, lanes 7-10; FIGS. 14C and D) as compared to wild type RNA and the binding levels were similar to those observed when either L1 or L2 was deleted or mutated (FIGS. 10, 11C, and 11D). These results indicated that the efficiency of binding was dependent on an optimal distance between the two small loops in the viral RNA.

The RNA binding sites of TIA-1 and TIAR proteins within the WNV3'(−)SL RNA were fine mapped to single-stranded UAAUU sequences in two loops (L1 and L2) of the WNV3'(−)SL RNA. This is the first identification of individual nts required for the binding of these proteins. The minimum sequence required for detectable protein binding in vitro was UAA. Optimal binding of both proteins was only observed when L1 and L2 were in a close proximity to each other.

Data from a previous SELEX study identified ~18 different RNA sequences each for TIA-1 and TIAR from random pools of RNA sequences that could bind efficiently. Each of these RNAs contained at least one U tract of 3 to 11 nts, as well as other AU sequences (Dember et al., 1996). These authors concluded that a single U stretch of at least 3 nts in length was essential for TIA-1 and TIAR protein binding. SELEX selects RNAs that bind with very high efficiency and based on the data obtained in the present study, it is likely that each of these RNAs contained more than one binding site. The secondary structure of these sequences was not considered by (Dember et al., 1996). These selected RNA sequences were folded using M-fold, version 3.1, and in the predicted optimal secondary structure of each RNA there were two single-stranded loops that contained either U or AU tracts. The results obtained for two of these RNAs are shown in FIGS. 15A and B. In general, the single-stranded loops in these predicted structures contained higher numbers of AU sequences than U tracts, suggesting that AU sequences rather than U tracts represented the TIA1- or TIAR binding sites.

Two previous studies (Lewis et al., 1998; Gueydan et al., 1999) utilized deletion/truncation mutants of the 3' NCR TNF-α mRNA to map the binding regions for TIA-1 and TIAR. The binding region was first identified as an ~80 nts fragment that contained 7 AUUUA pentamer motifs, two of which overlapped. This region could be further truncated to a sequence of 39 nts, that contained the two overlapping pentamer motifs and an additional single AUUUA pentamer, without diminishing protein binding, but the TIA-1 and TIAR binding sites within this RNA were not fine mapped. The secondary structure of the 3' NCR TNF-α mRNA was not considered. When the secondary structure of the full length TNF-α mRNA was predicted using M-fold version 3.1 (Zuker, 2003), two AU-rich loops (T-L1 and T-L2) in close proximity to each other were predicted for the 80 nt binding region (FIG. 15C, bracketed sequence) SEQ ID NO. 30, and an additional nearby AU-rich loop (T-L3) was also observed (FIG. 15C). The predicted secondary structure of the 3' NCR TNF-α mRNA was similar to that of the WNV3'(−)SL RNA in having three single-stranded AU rich loops (T-L1, T-L2, and T-L3). Although the distance between T-L1 and T-L2 was greater than that observed between L1 and L2 in the WNV3'(−)SL RNA, these cell RNA loops were larger than those in the viral RNA. T-L1 contained 4 and T-L2 contained one the AUUUA pentamer motifs previously predicted to be the binding sites for TIA-1 and TIAR. T-L3 contained one AUUUA pentamer that was not located within the mapped binding region of either protein. When the AU-rich 80 nt binding sequence was deleted from the 3' NCR of TNF-α mRNA, no binding was observed with either protein (Gueydan et al., 1999). Prediction of the secondary structure of a full length TNF-α mRNA with this deletion showed only minimal local alterations in the structure and T-L3 was maintained. Since both T-L1 and T-L2 contain tracts of AU nts in addition to the AUUUA pentamers, without further testing the actual binding sites for these proteins within this 3' UTR can not be predicted.

AU-rich elements have been defined as class I ARE RNA (1 to 3 copies of the canonical sequence AUUUA), class II (at least two overlapping copies of the nanomer UUAUUUA (U/A) in a U rich region), and class III (a U-rich region). The third class has also been called the non AUUUA group. Gueydan et al., (1999) classified TIA-1 and TIAR as class II ARE proteins based on the assumption that the AUUUA pentamers were the binding sites. The results of the present study show that TIA-1 and TIAR bind efficiently to two UAAUU sequences in the WNV3'(−)SL RNA and suggest that TIA-1 and TIAR may be class III ARE proteins.

Previous studies showed that recombinant TIA-1 and TIAR proteins interacted specifically with the WNV3'(−)SL RNA (Li et al., 2002). The binding sites of both proteins were previously mapped to the AU sequences in L1 and L2 in the context of the secondary structure of the WNV3'(−)SL RNA using in vitro gel mobility shift assays (FIG. 16A) (Emara and Brinton, 2006). In TIAR knockout cells, the replication of WNV was reduced by 6- to 8-fold compared to control cells (Li et al., 2002). To determine whether disruption of the TIA-1 and TIAR binding sites in L1 or L2 affect virus production, mutations and/or deletions were introduced into these loops in a WNV infectious clone. BHK monolayers were transfected with wild type or mutant infectious clone RNA as described in Examples and virus plaques produced by 72 hr after transfection in the overlayed transfection plates were assayed.

Figure 16:
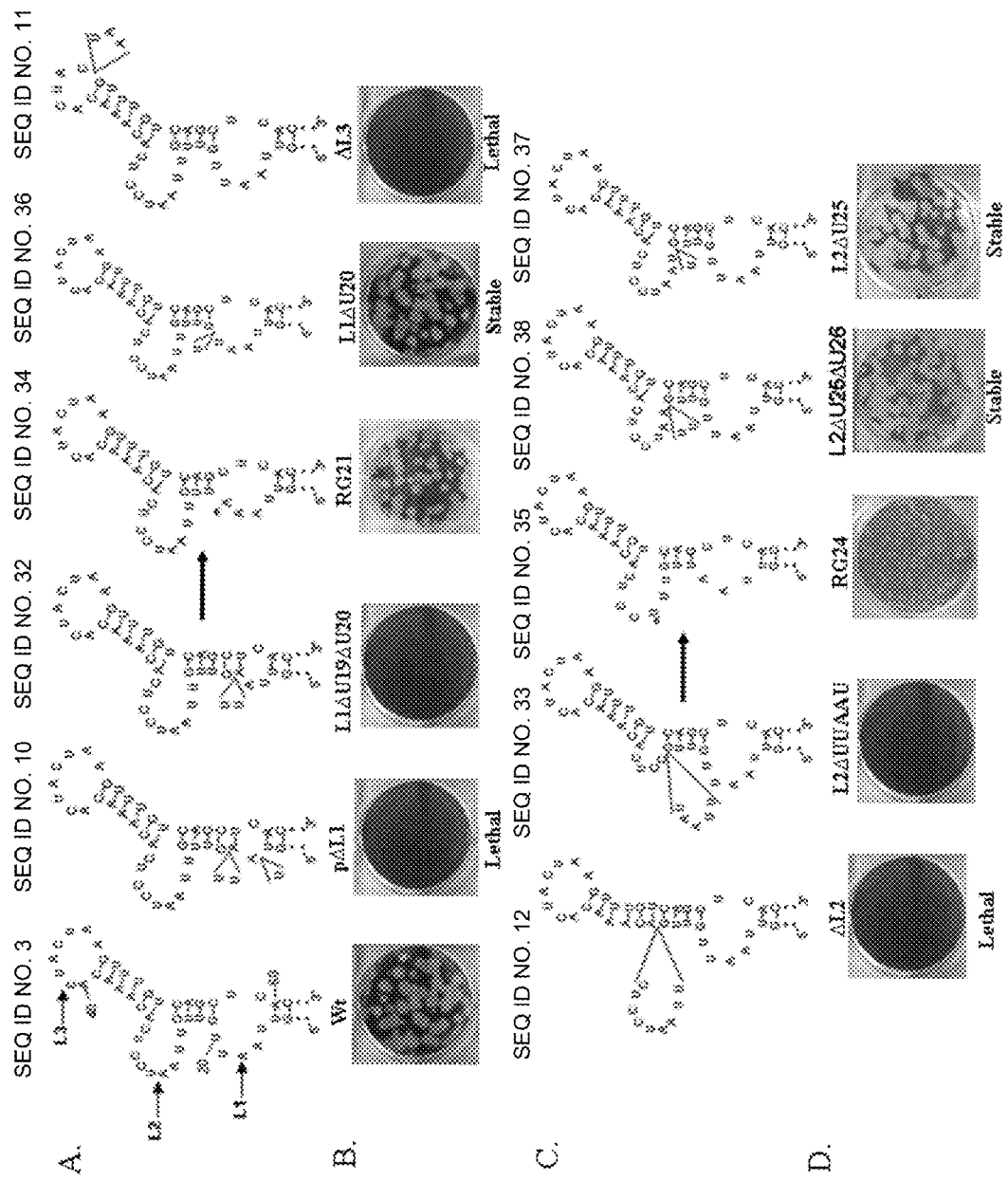
FIG. 16 A-D shows the effect of deletion of A and U nucleotides in L1, L2, or L3 (arrows) of the WNV3'(−)SL RNA on virus production.

Deletion of each loop was done separately or in combination. Mfold analysis indicated that the predicted RNA secondary structure of the wild type RNA was preserved in each of these mutants (FIGS. 16A and C). Only 3 nts could be deleted in L1 (U16, U19, and U20, pΔL1) without affecting the predicted RNA secondary structure of the WNV3'(−)SL RNA, while all of L2 could be deleted (ΔL2) (FIG. 16C). Deletion of both U19 and U20 in L1 or 5'UAAUU3' in L2 created L1ΔU19U20, SEQ ID NO. 32, and L2ΔUAAUU SEQ ID NO. 33, RNAs, respectively (FIGS. 16A and C). No plaques were observed in plates transfected with pΔL1, (SEQ ID NO. 10) ΔL2, (SEQ ID NO. 12) L1ΔU19U20 (SEQ ID NO.32), or L2ΔUAAUU (SEQ ID NO. 33) RNA (FIGS. 16B and D).

To test whether those mutants that produced no plaques after transfection could revert, culture media harvested from a non-overlayed duplicate well was serially passaged three times in BHK cells and the 72 hr harvest from each passage was tested by plaque assay. The viral RNA in each passage supernatant was extracted, amplified by RT-PCR and the cDNA sequenced. For pΔL1 and ΔL2, neither viral plaques nor viral RNA was detected after passage. In contrast, after one passage small plaques and large plaques were observed with L1ΔU19U20 and ΔUAAUUL2, respectively (FIGS. 16B and D). RNA extracted from the L1ΔU19U20 small plaque virus contained the second site reversion G21 to A (RG21) SEQ ID NO. 34, (FIG. 16A), whereas RNA extracted from the ΔUAAUUL2 large plaque virus contained the second site reversion G24 to a U (RG24) SEQ ID NO. 35, (FIG. 16C). These reversions restored three As or Us to L1 or L2, respectively (FIGS. 16A and C). Deletion of a single U from either loop (U20 in L1, L1ΔU20 SEQ ID NO. 36, or U25 in L2, L2ΔU25, SEQ ID NO.37) or 2 Us (U25 and U26, L2ΔU25Δ26, SEQ ID NO. 38) in L2, which left a minimum sequence of UAA, had no effect on virus growth (FIGS. 16B and D). These results indicate that the same minimal AU sequences in L1 and L2 found to be required for TIA-1 and TIAR in vitro binding were required for virus viability. Although there was no effect on TIA-1 and TIAR in vitro binding when UAA in L3 (ΔL3) SEQ ID NO. 39, (FIG. 16C) was deleted, these mutations were lethal in the infectious clone (FIG. 16D), suggesting that L3 is involved in other interactions.

Figure 17:
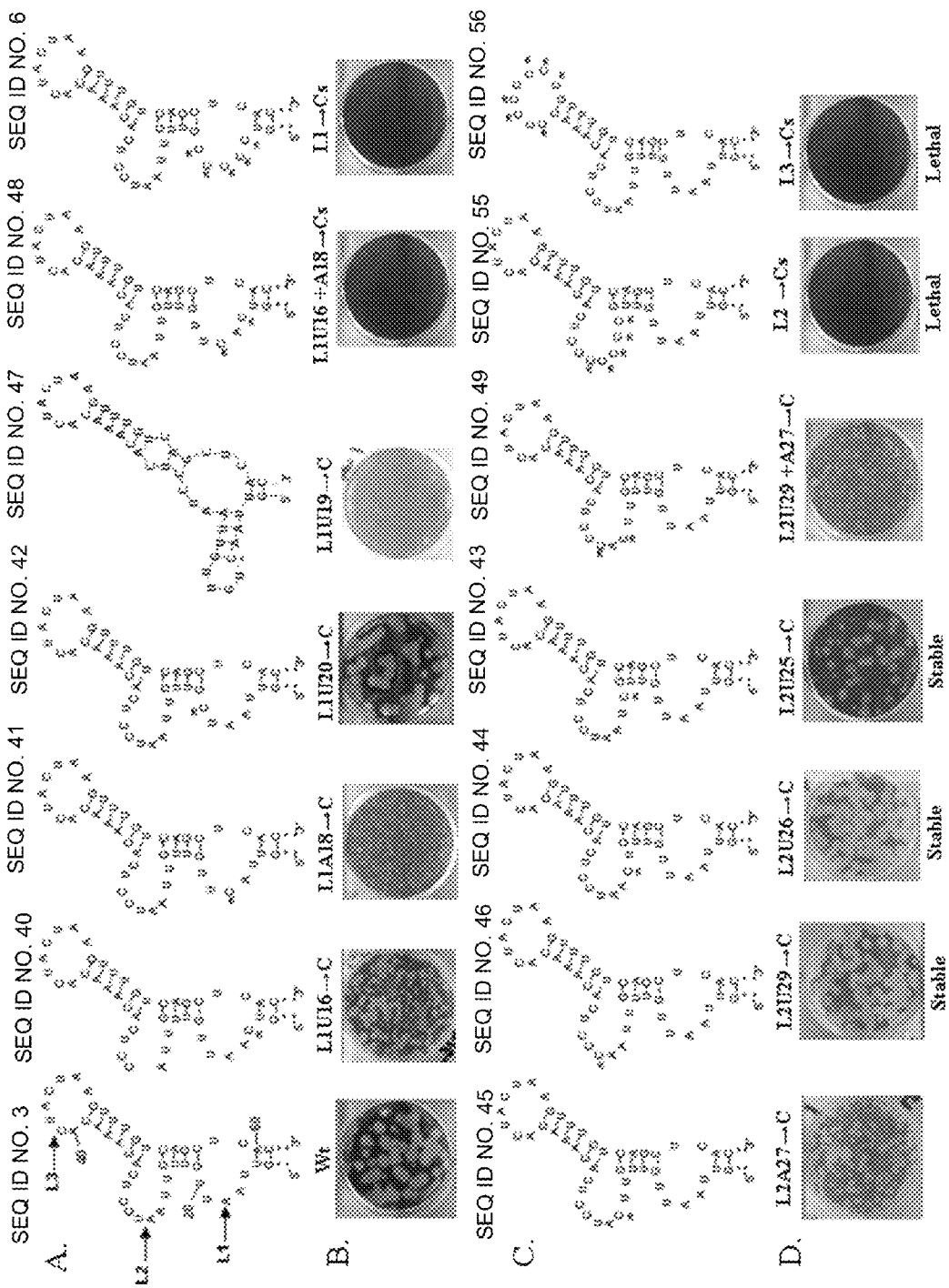
FIG. 17 A-D shows the effect of C substitutions in L1, L2, or L3 of the WNV3'(−) SL RNA on virus production.

Effect of substitution of L1 and L2 with Cs on virus production. As an alternative mutational strategy, Cs were substituted for Us or As in L1 or L2. First, individual substitutions were introduced at positions U16, A18, and U20 in L1 to generate L1U16→C SEQ ID NO.40, L1A18→C SEQ ID NO.41, and L1U20→C, SEQ ID NO. 42, RNAs (FIG. 17A), respectively, and at positions U25, U26, A27, and U29 in L2 to create L2U25→C, SEQ ID NO.43, L2U26→C, SEQ ID NO.44; L2A27→C, SEQ ID NO.45; and L2U29→C, SEQ ID NO. 46, RNAs (FIG. 17C), respectively. None of these mutations altered the predicted secondary structure of the WNV3'(−)SL RNA. L1U16→C, L1A18→C, and L2U27→C produced virus with a small plaque phenotype (FIGS. 17B and D). After one passage, large plaques similar to those of the wild type virus were observed and in the RNA extracted from these plaques the mutated nts had reverted to the wild type sequence. When U19 was changed to a C (L1U19→C), SEQ ID NO. 47, the 3'(−)SL structure was predicted to change (FIG. 17A) and only a few pinpoint plaques were observed by 72 hr on the transfection plate (FIG. 17B). After the first passage, large size plaques were observed and in the RNA extracted from these plaques C19 had reverted to the wild type U19. In contrast, L1U20→C, L2U26→C, and L2U29→C had no effect on virus growth (FIGS. 17B and D).

Figure 1A:
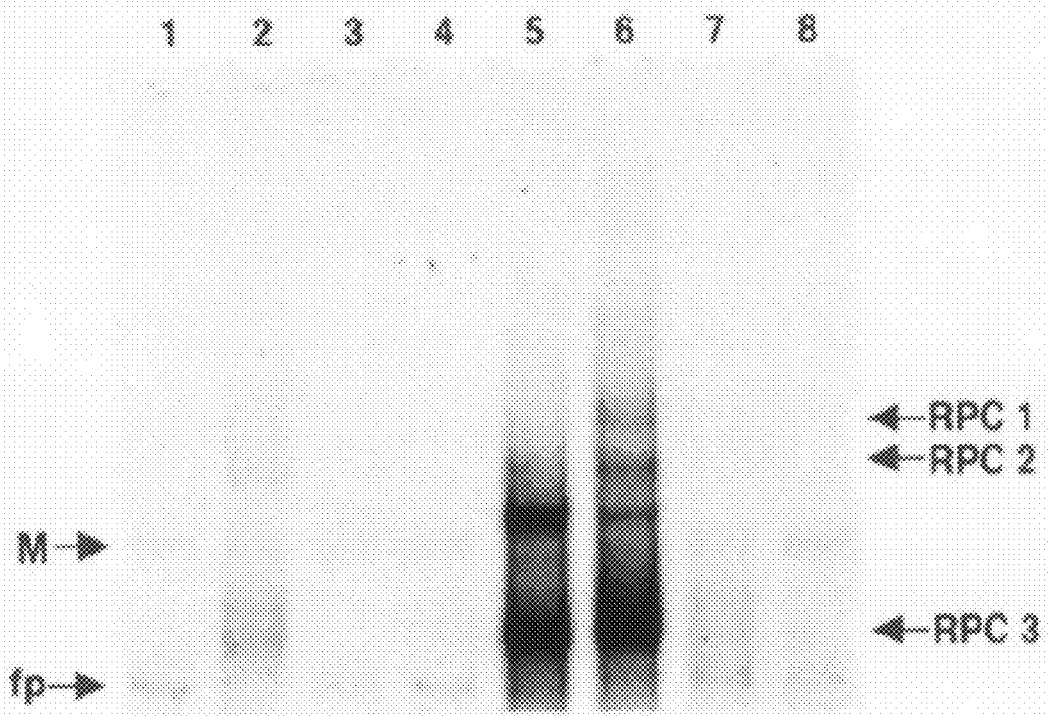
FIG. 1 A-B shows polyacrylamide gels showing gel mobility shift experiment results.
Figure 1B:
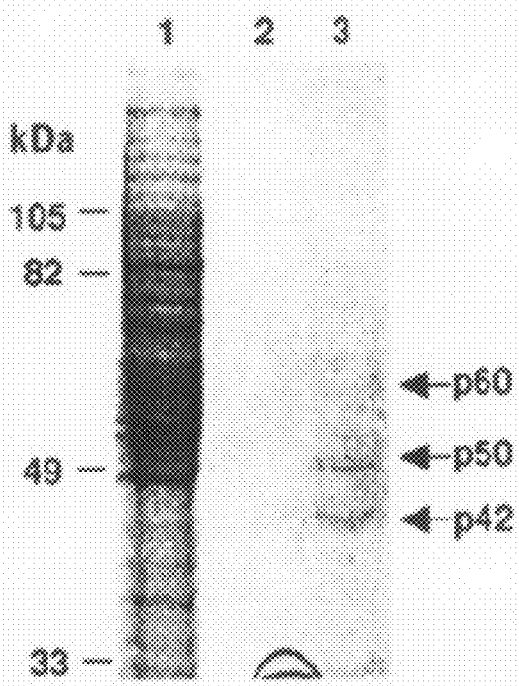

No plaques were detected on the transfection plate when both U16 and A18 were substituted with Cs (L1U16+A18→C) SEQ ID NO. 48, (FIG. 17B), but after one passage, small plaques similar to those detected with either the L1U16→C or L1A18→C mutants were observed (FIG. 17B). RNA extracted from these small plaques contained a double reversion of C16 to the wild type U16 and C18 to A18. Substitution of both A27 and U29 with C (L2U27+U29→C) SEQ ID NO.49 produced virus with a small plaque phenotype. After one passage, large plaques similar to those detected with L2U29C were observed (FIG. 17D) and the RNA extracted from these large plaques contained a reversion of C27 to the wild type A27. The observation that mutants L1A18→C, L2U27→C, and L2U27+U29→C were not lethal but produced small plaques even though a minimal UAA sequence was absent from one of these two loops suggests the existence of an alternative binding sequence that contains a C as well as Us and As. Finally, global substitutions were introduced at positions 16 to 20 (L1→Cs), at positions 25 to 29 (L2→Cs), SEQ ID NO.55, and at positions 40 to 47 (L3→Cs) SEQ ID NO. 56 (FIGS. 1A and C). As observed with the pΔL1, ΔL2, or ΔL3 RNAs, the L1→Cs, L2→Cs and L3→Cs mutants were lethal (FIGS. 1B and D). These results confirmed that a minimum sequence of UAA is required in both L1 and L2 for virus viability.

Effect of Substitution of L1 and L2 with As and Us.

Figure 18:
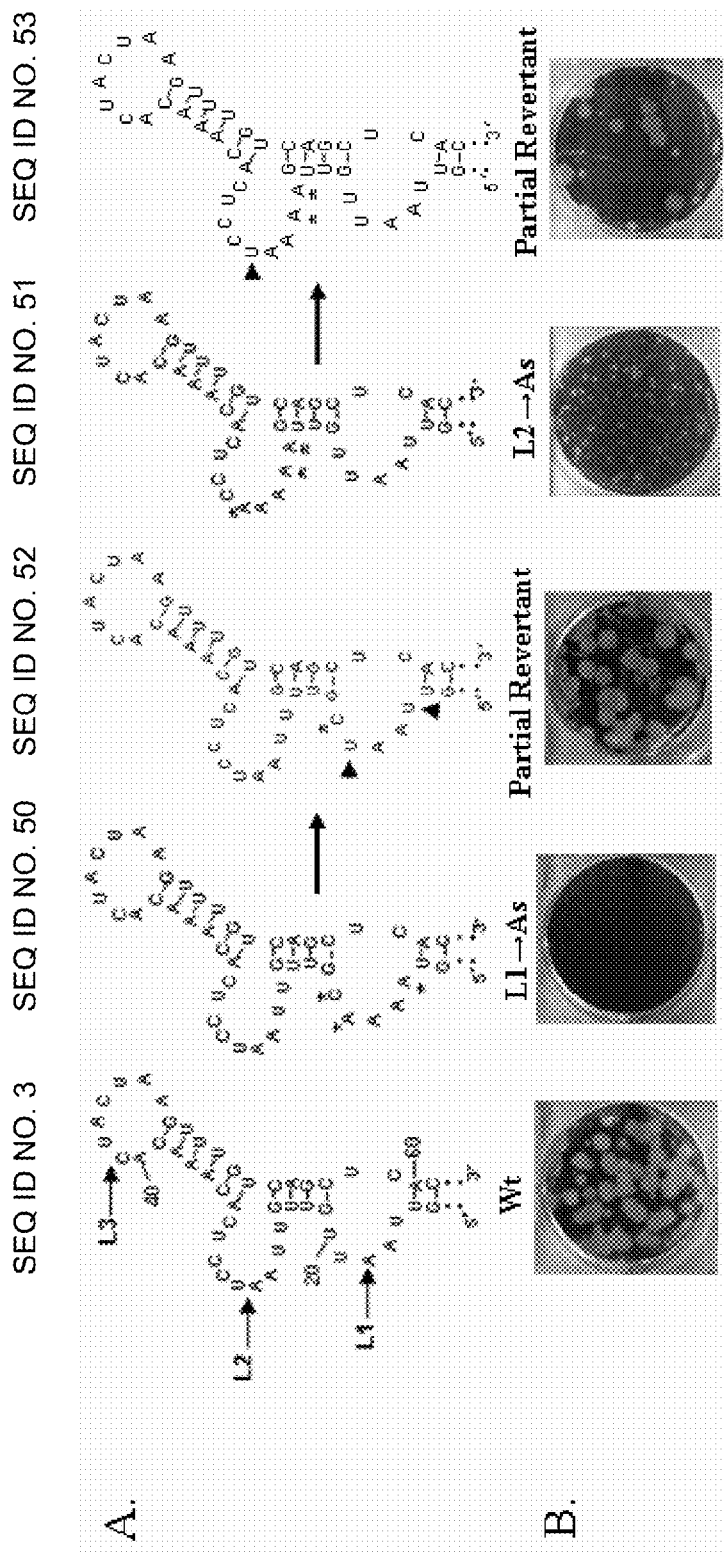
FIG. 18 A-B shows the effect of A substitutions in L1 or L2 within the WNV3'(−) SL RNA on virus production.

Substitution of Us in L1 or L2 to As did not alter TIAR binding activity but enhanced TIA-1 binding activity. To determine whether increasing the number of As in L1 or L2 affected virus production, Us in L1 and L2 were replaced separately with As and the mutant RNAs were transfected into BHK cells. L1 (5'UAAUU3') was replaced with 5'AAAAC3' to form the L1→As. In this mutant, U20 was mutated to a C instead of an A to preserve the predicted RNA secondary structure (FIG. 18A). Us within L2 was replaced with As to make L2→As. No plaques were detected 72 hr post transfection of L1→As, SEQ ID NO. 50, whereas small plaques were detected on the plate transfected with L2→As, SEQ ID NO. 51 (FIG. 18B). After one passage, large plaques were observed with both mutant RNAs (FIG. 18B), indicating that both of these mutants had a negative effect on virus growth, but that the L1 mutation had a greater effect. RNA extracted from these plaques contained reversion of both A16 and A19 in L1 (SEQ ID NO. 52) and A29 in L2 (SEQ ID NO. 53) to the wild type U nts (FIG. 18A). These results showed that mixtures of A and Us in L1 and L2 are optimal for virus viability.

Figure 19:
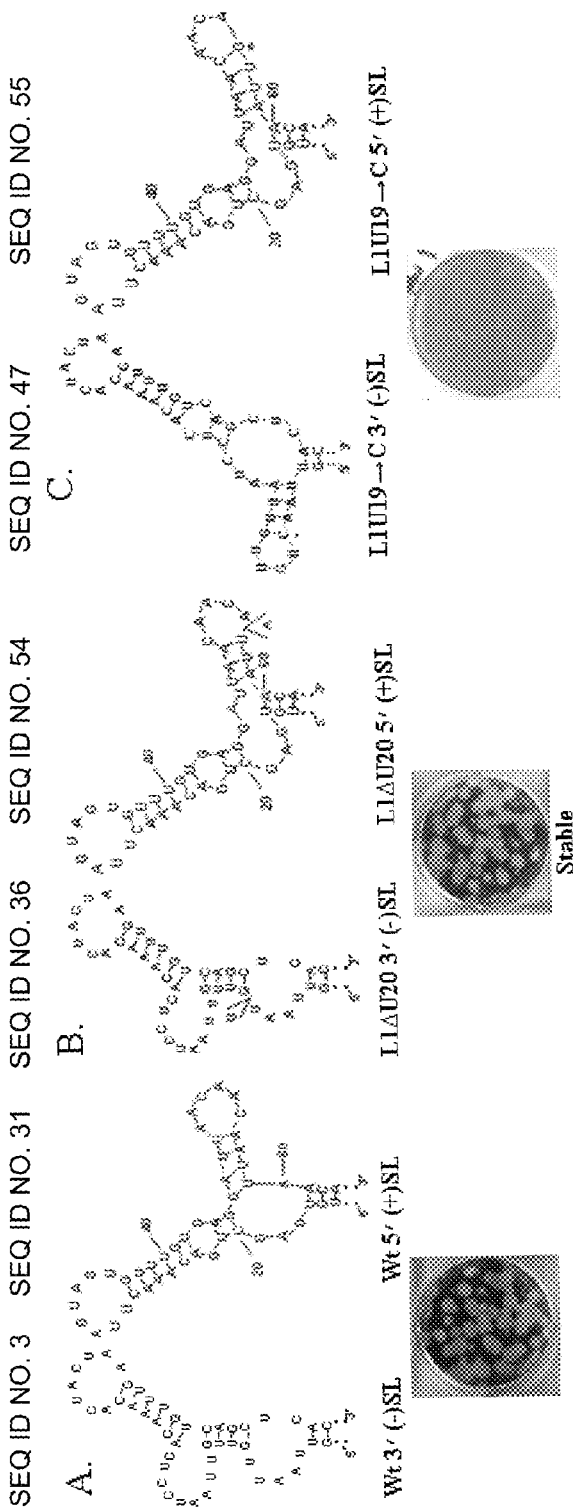
FIG. 19 A-C shows the effect of the introduced mutations on the predicted secondary structure of the complementary 5'(+)SL RNA.
Figure 20:
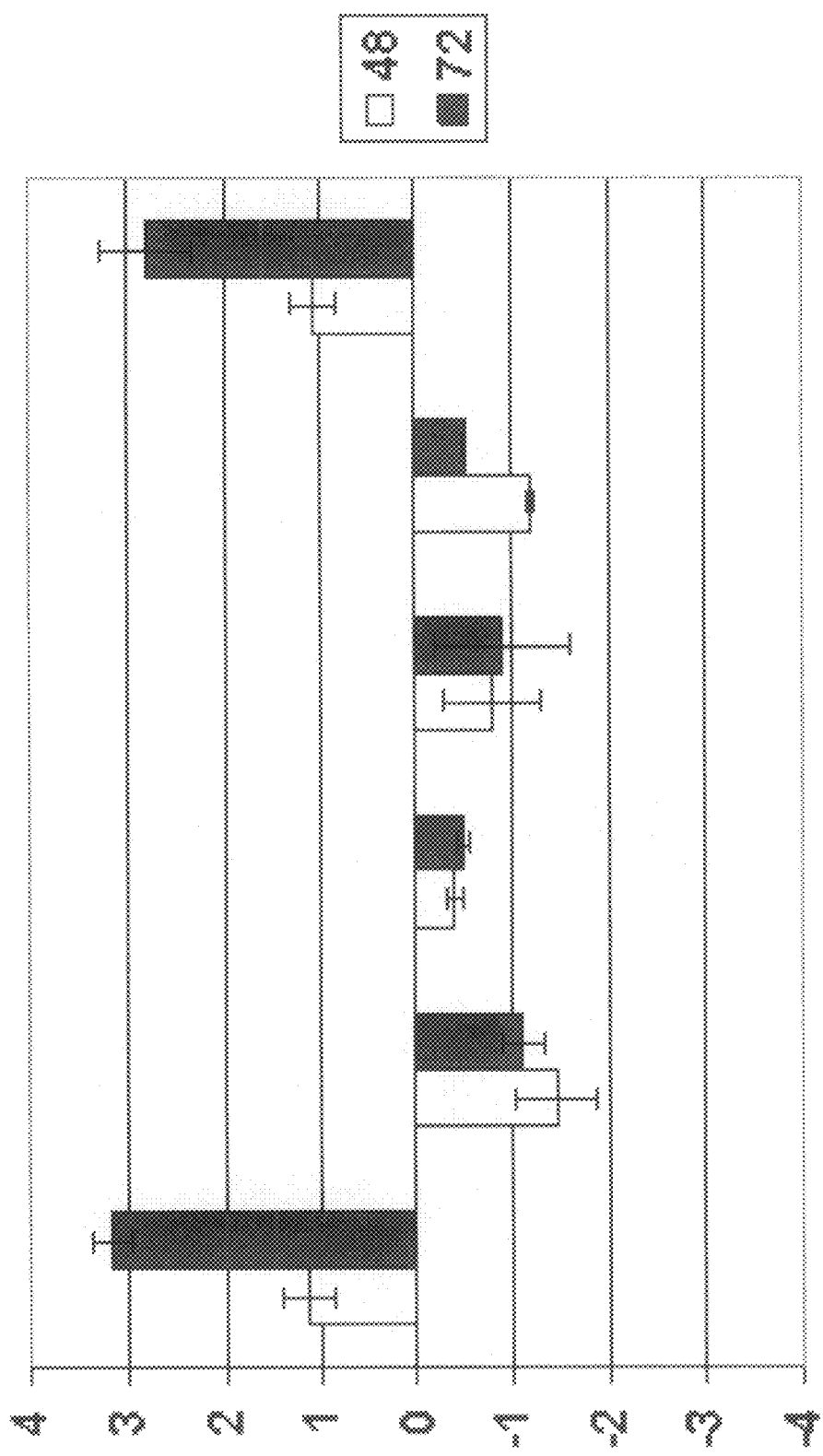
FIG. 20 shows the relative quantification of the levels of the intracellular viral genomic RNA at 6, 48, and 72 hr post transfection of either wild type or mutant infectious clone RNA by real-time RT-PCR.

Effect of the introduced mutations on the predicted secondary structure of the complementary 5'(+)SL RNA. It was previously shown that the predicted secondary structure of the terminal 75 nts of the WNV3'(−)SL RNA differed from that for the complementary WNV5'(+)SL RNA (FIG. 19A). To exclude the possibility that some of the mutations analyzed in this study might change the predicted secondary structure of the complementary WNV5'(+)SL RNA, the effects of these mutations on the predicted structure of WNV5'(+)SL RNA were analyzed. Selected examples are shown. Deletion of U20 from L1, which had no effect on the predicted secondary structure of the WNV3'(−)SL RNA (L1ΔU20 3'(−)SL) and had no effect on viral growth was predicted to alter the lower part of the structure of the complementary WNV5'(+)SL RNA (L1ΔU20 5'(+)SL), SEQ ID NO. 54 (FIG. 19B). A similar altered structure was predicted for the complementary WNV5'(+)SL SEQ ID NO.55, of the U19→C mutant (U19→C 5'(+)SL), which grow very poorly (FIG. 19C). These results show that structural changes in the complementary WNV5'(+)SL RNA do not correlate with the viral phenotype observed.

Relative quantification of genomic RNA replication by real-time RT-PCR. As another means of assessing the effect of mutations in the WNV3'(−)SL on viral replication, total cell RNA was extracted at 6, 48, and 72 hr post transfection from BHK cells transfected with wild type or mutant viral RNA. The RNA was subjected to real-time RT-PCR using primers located in the viral NS1 region. GADPH was used as the endogenous control gene to normalize variation between replicate samples and viral RNA levels were normalized to the amount of input viral RNA present at 6 hr post transfection. A steady increase in RNA levels between 48 and 72 hr post transfection was observed after transfection of the wild type genomic RNA. The various L1 and L2 mutant RNAs that formed no plaques at 72 hr post transfection also showed no significant increase in RNA levels during the same period of time. The results of these experiments showed that loop 1 and loop 2, which were found to be the binding sites of TIA-1 and TIAR proteins are essential for virus production.

Effect of the Introduced Mutations on the Virus Translation.

It was next determined whether the mutations made affected viral RNA transcription and/or translation. Viral RNA transfected BHK cells were fixed and permeabilized 4 hours after transfection. Cells were incubated with a mouse anti-WNV hyper-immune sera and the effect of mutations on viral translation was observed by confocal microscopy. Those with Mutants ΔL1, ΔL2, L1→Cs, and L2→Cs were lethal. Mutation U16→C produced small plaques and mutation L1ΔU25 produced wild-type plaques. All produced similar levels of viral protein expression at four hours after tranfection as wild-type RNA.

Methods and compositions for inhibition of viral replication are disclosed in U.S. patent application Ser. No. 10/654,273, herein incorporated in its entirety.

The present invention comprises compositions comprising nucleotide sequences to which proteins involved in viral replication, whether viral or host proteins bind. Such sequences include but are not limited to, two closely spaced loops containing UAAU, AAAA, or UUUU, sequences comprising UAAU, AAAA, or UUUU, or UAAU, AAAA, or UUUU, or modified nucleotides or variants thereof. Methods for inhibiting viral replication comprise providing an effective amount of replication inhibiting sequences to a subject or cell culture prior to or during a viral infection to inhibit the replication of the virus. Methods of replication inhibition are taught herein. Deletions or mutations in the stem loop structure or AU sequences may also effect the viral inhibition. Providing of such interfering sequences, such as the compositions taught herein, interfere with the binding of the proteins to the viral sequences and thus inhibit viral replication.

Compositions for inhibiting the activity of host cell proteins such as p50, p60, p108, p105, p 52, p84, TIAR or TIA-1 can be provided as pharmaceutically acceptable formulations using formulation methods known to those of ordinary skill in the art. These formulations can be administered by standard routes. In general, the compositions may be administered by the topical, transdermal, oral, rectal or parenteral (e.g., intravenous, subcutaneous or intramuscular) route. In addition, the compositions may be incorporated into biodegradable polymers allowing for sustained release of the compound, the polymers being implanted in the vicinity of where drug delivery is desired, for example, in infected tissues or provided to the organism for sustained release of the compound to the entire organism, for example, via gastrointestinal absorption.

The dosage of the compound will depend on the condition being treated and the extent of infection, the particular compound, and other clinical factors such as weight and condition of the human or animal and the route of administration of the compound. It is to be understood that the present invention has application for human, veterinary or plant use. For example, for administration to humans, a dosage of between approximately 0.1-75 mg/kg/day, preferably, a dosage of between approximately 10-50 mg/kg/day, most preferably, a dosage of between approximately 10-30 mg/kg/day. Alternatively, nucleic acid constructs provided in methods of gene therapy are provided in dosages of picogram to micrograms/kg/day, between approximately 0.001 µg/kg/day to 100 µg/kg/day. Depending on the route of administration, the compound administered and the toxicity of that compound, a preferable dosage would be one that would yield an adequate blood level or tissue fluid level in the human, animal or insect that would effectively inhibit replication of the virus.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations suitable for nasal administration, wherein the carrier is a solid, include a coarse powder having an appropriate particle size, microns, which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

The compositions of the present invention are used in methods of treatment of viral diseases. Such methods comprise administration of a composition effective in interfering or inhibiting viral replication in an individual having a viral infection. Such compositions include compounds that are effective in interfering or inhibiting the interactions of host proteins in the viral replication pathway. In particular, such compositions interfere with the interactions by one or more of p 50, p 60, p108, p105, p 52, p84, TIAR or TIA-1 with viral nucleotides or alter other functions of the proteins, such as stress granule formation or apoptosis. An embodiment of a composition comprises a nucleic acid construct that mimics a portion of a viral nucleic acid, such that the nucleic acid construct, and competes for the binding of one or more host cell proteins, such as p 50, p 60, p108, p105, p 52, p84, TIAR or TIA-1. An embodiment of a method of treatment of a viral disease comprises administering to a human, animal or insect a composition comprising a nucleic acid construct capable of competing for binding of one or more host cell proteins related to viral replication, in an amount effective to inhibit viral replication. An embodiment of a method of treatment of West Nile virus infection comprises administering to an individual, including a human or an animal, infected with West Nile virus, a composition comprising a compound capable of affecting one or more host cell proteins involved in West Nile virus replication, in an amount effective to interfere with or inhibit viral replication.

As used herein, individual can mean humans, animals, birds, insects, plants or other organisms that can be infected by viruses.

As used herein, "a" or "an" can mean multiples. For example, "a cell" can mean at least one cell or more than one cell.

It should be understood, of course, that the foregoing relates only to preferred embodiments of the present invention and that numerous modifications or alterations may be made therein without departing from the spirit and the scope of the invention as set forth in the Examples and appended claims.

EXAMPLES

Example 1

Materials and Methods Used Herein

Cells.

Baby hamster kidney (BHK-21/WI2) cells (42) (referred to hereafter as BHK cells) were used to prepare S100 cytoplasmic extracts or ribosomal salt wash cell extracts. BHK, CV-1 and Vero cells were maintained at 37° C. in a $CO_2$ incubator in Minimal Essential Medium (MEM) supplemented with 10 µg/ml gentamycin and 5% or 10% fetal calf serum (FCS).

TIAR-knockout C57BL/6 mice and TIA-1-knockout Balb/C mice were prepared as described previously (2, 33). Embryo fibroblast cell lines were established from wild type (W4 and TIA$^{+/+}$43), TIAR-knockout (NaR4 and TIAR$^{-/-}$43) and TIA-1-knockout (a$^{-/-}$43 and TIA$^{-/-}$44) mouse embryos using the standard NIH 3T3 protocol.

To prepare control-reconstituted and TIAR-reconstituted (TIAR-REC) cell lines, TIAR-knockout (TIAR$^{-/-}$43) cells were transfected with a pSR-α-hygromycin vector containing full-length human TIAR cDNA (a gift from Dr. M. Streuli, Dana Farber Cancer Institute, Boston, Mass.) by the calcium phosphate method (35). Stable cell lines were established from clones that grew in the presence of hygromycin. Reconstituted cells were re-selected by growth in hygromycin for one week prior to use in experiments. These cell lines were maintained in MEM supplemented with 10% FCS, 10 mM HEPES and 10 µg/ml gentamycin in a $CO_2$ atmosphere at 37° C.

Viruses.

Stocks of WNV, strain EG101, (titer=$2\times10^8$ PFU/ml) and Sindbis virus, strain SAAR 339, (titer=$7\times10^9$ PFU/ml) were prepared as 10% (w/v) newborn mouse brain homogenates. A stock of vaccinia virus, Wyeth strain, was prepared as a CV-1 cell lysate (titer=$1.2\times10^8$ PFU/ml). A stock of herpes simplex virus [HSV-1; strain H129 (HO], was prepared as a media pool in Vero cells (titer=$1.6\times10^8$ PFU/ml) and vesicular stomatitis virus (VSV), strain Indiana, was prepared as a media pool in L cells (titer=$4.8\times10^7$ PFU/ml).

For virus growth experiments, confluent monolayers of wild-type or knockout cells in T25 flasks were infected with WNV at a multiplicity of infection (MOI) of 1, and culture fluid samples (0.5 ml) were harvested at different times post-infection (p.i.). At each time point, 0.5 ml of fresh media was replaced to maintain a constant volume in the flask. Harvested WNV samples were titrated in duplicate on BHK cells by plaque assay. Monolayers of cells in T25 flasks were also infected at an MOI of 1 with Sindbis virus, vaccinia virus, herpes simplex virus (HSV)-1, or vesicular stomatitis virus (VSV). Virus yields at different times post-infection were determined by plaque assay. Sindbis was plagued on BHK cells, vaccinia on CV-1 cells, HSV-1 on Vero cells, and VSV on BHK cells.

In Vitro Transcription of $^{32}$P-Labeled RNA Probes and Unlabeled RNA Transcripts Plasmid p75nt(-)3' was previously constructed by P.-Y. Shi (36). A PCR product, PCRT73' (-)SL, that consisted of the 75 3' terminal nts of the WNV minus-strand RNA with three extra C's at the 5' end copied from the T7 promoter, was amplified from plasmid p75nt(-)3' DNA using a M13 reverse primer SEQ ID NO 1: (5'-CAGGAAACAGCTAT-GACCATG-3'), and a forward primer SEQ ID NO 2: (5'-AGTAGTTCGCCTGTGTGAGC-3'). The 3' (-)SL RNA was transcribed from the amplified PCR DNA. The T7 polymerase used for in vitro RNA transcription was expressed from BL21 cells containing pAR1219 (kindly provided by Dr. F. W. Studier, Brookhaven National Laboratory) and purified as described by Davanloo et al. (11).

The methods used for in vitro transcription and gel purification of the $^{32}$P-labeled RNA probes and unlabeled competitor RNAs were described previously (37). Large scale batches of unlabeled RNAs, needed for RNA affinity columns, were prepared by scaling up the in vitro transcription reaction to 1 ml and extending the reaction time to 4 h.

RNA-Affinity Column.

In vitro transcribed WNV 3' (−)SL RNA was oxidized with periodate in the presence of NaOAc (pH 5) and then attached to an agarose adipic acid matrix as described by Blyn et al. (4, 5). The RNA-matrix (1 ml) was poured into a 10 ml column and then equilibrated with column binding buffer [5 mM HEPES (pH 7.5), 25 mM KCl, 2 mM $MgCl_2$, 0.1 mM EDTA, and 2 mM dithiothreitol].

BHK S100 cell extracts prepared as described previously (37) were subjected to ammonium sulfate precipitation prior to passage through an RNA-affinity column. Ammonium sulfate was first added to a final concentration of 16%. Ammonium sulfate was then added to the supernatant obtained from the first precipitation to a final concentration of 45% and the resulting pellet was resuspended in storage buffer. The pellet fraction was preincubated with non-specific competitors polyIC (1 mg/ml) and heparin (500 µg/ml) at 4° C. for 10 min, and then passed over the RNA-affinity column three to five times. The column was then washed several times with column binding buffer and once with the same buffer containing 0.2 M NaCl. The bound proteins were eluted with column binding buffer containing 1 or 2 M NaCl. The eluted fractions were subjected to buffer exchange in a Centricon-30 (Amicon). Aliquots of each fraction were analyzed for RNA binding activity by gel mobility shift assay. Proteins were detected by Gold blot staining (Integrated Separation Systems). The proteins in the eluted fractions were then separated by SDS-PAGE, visualized by Coomassie blue staining. Protein bands were excised and peptides were generated by trypsin digestion. The peptides were separated by HPLC and the sequences of selected peptides were determined by automated liquid chromatography-tandem mass spectrometry using a Finnigan MAT LCQ ion trap mass spectrometer as described previously (12, 13, 38).

RNA-Protein Interaction Assays.

Gel mobility shift and UV-induced crosslinking assays were performed as described previously (37). Prior to use in these assays, RNA probes were denatured by incubation at 90° C. for 10 min followed by renaturation by slow cooling to 60° C. and incubation at 60° C. for ~2 min. The probe was then kept on ice until use.

Immunoprecipitation of UV-Crosslinked Proteins.

Proteins in S100 cytoplasmic extracts were first crosslinked to $^{32}$P-labeled WNV 3' (−)SL RNA as described above. The cross-linked proteins were then incubated for 2 h at 4° C. with 1 µg/ml of anti-TIAR antibody [6E3, murine mAb IgG2a; (1)] or anti-TIA-1 antibody [ML29, murine mAb IgG1; (22, 39)] that had been preincubated with Sepharose A CL-4B beads (Pharmacia). The precipitated complexes were pelleted by centrifugation at 300×g, washed twice with dilution buffer [0.1% Triton X-100 and 0.5% nonfat dry milk in TSA buffer (0.01 M Tris-HCl, pH 8.0, 0.14 M NaCl, 0.025% $NaN_3$)], once with TSA buffer and once with 0.05 M Tris-HCl (pH 6.8). The immunoprecipitated complexes were then separated by 10% SDS-PAGE and visualized by autoradiography.

Immunoblotting.

BHK cells from a confluent monolayer in a T75 flask were trypsinized, pelleted by centrifugation for 3 min at 150×g, and washed three times with 1× phosphate-buffered saline (PBS). The cell pellet was resuspended in ice-cold lysis buffer (1×PBS, 1% Nonidet P-40, 0.5% sodium deoxycholate, 0.1% SDS) containing freshly added protease inhibitors (1× Complete, Roche), and passed through a 21-gauge needle four times. Nuclei were removed from the cytoplasmic extracts by centrifugation at 10,000×g for 10 min at 4° C. The total protein concentration in the extracts was determined using a Dc protein assay kit (BioRad). Proteins in 20 µg of extract were separated by 10% SDS-PAGE and then electrophoretically transferred to a nitrocellulose membrane (0.45 micron pore size, BioRad). The membrane was blocked with Blotto A [10 mM Tris-HCl, pH 8.0, 150 mM NaCl (TBS), 5% non-fat dry milk, 0.05% Tween 20] for 1 hr at room temperature or overnight at 4° C., and probed first with an anti-protein primary antibody and then with a horseradish peroxidase (HRP)-conjugated secondary antibody diluted in Blotto A. The membrane was washed three times with 1×TTBS (1×TBS containing 0.05% Tween 20) and then once with 1×TBS prior to incubation with Chemiluminescence Reagent (Santa Cruz Biotech) and detection of the proteins by autoradiography.

Mouse anti-TIAR monoclonal antibody 6E3 was used at 0.8 µg/ml and goat anti-TIA-1 polyclonal antibody (Santa Cruz Biotech) was used at 0.5 µg/ml. HRP-conjugated goat anti-mouse IgG and donkey anti-goat IgG were used at 0.2 µg/ml (Santa Cruz Biotech).

Indirect Immunofluorescence.

Cells were grown to about 50% confluency in the wells of a two-chamber Lab-Tek II slide (Nalge Nunc International) and infected with WNV at a MOI of 5. At various times after infection, the cells were fixed with 2% paraformaldehyde for 10 min at room temperature, permeabilized with ice-cold methanol for 10 min, stained with a 1:100 dilution of a hyperimmune mouse anti-WNV antibody (Walter Reed Army Institute of Research) for 1 h, and then washed three times with PBS. The cell nuclei were then stained with Hoechst Dye (33258) and FITC-goat anti-mouse IgG (Jackson ImmunoResearch Laboratories) for 1 h and washed three times with PBS. The coverslips were mounted in vinol mounting media (17) and viewed with a Nikon Eclipse 800 microscope equipped with epifluorescence optics and appropriate filters for detection of FITC, Texas red or Hoechst dye.

Preparation of Figures.

Autoradiographs of gels or membranes were scanned with an Arcus II Agfa scanner. The digitalized images were adjusted using Adobe Photoshop (version 5.5) software on a Power PC Macintosh G3.

Example 2

Purification of the WNV 3' (−) SL RNA-Binding Proteins

Three RNA-protein complexes, RPC1, -2 and -3, were detected in gel mobility shift assays done with a $^{32}$P-WNV 3'(−) SL RNA probe and BHK S100 extracts (37). UV-induced crosslinking assays indicated that these complexes contained four cell proteins (p42, p50, p60, and p108) that bound specifically to the WNV 3' (−) SL RNA. An RNA affinity column was used to purify these viral RNA binding proteins.

In a preliminary experiment, a BHK S100 cytoplasmic extract that was prepared from ten T150 flasks of cells was subjected to precipitation with different concentrations of ammonium sulfate. Supernatant and pellet fractions were analyzed for viral RNA binding activity by gel mobility shift and UV-induced crosslinking assays. Although a pellet was obtained after precipitation with 16% ammonium sulfate, none of the four cell proteins that bound to the viral 3' RNA were present in this pellet in detectable amounts. After precipitation with 45% ammonium sulfate, there was good recovery of RPC2 and RPC3, but only a small amount of RPC1 were detected in the pellet fraction by gel mobility shift assay. UV-induced crosslinking assays indicated that p60, p50, p42, but only a small amount of p108, were present in the pellet fraction.

The proteins in the 45% ammonium sulfate pellet were resuspended in column binding buffer, incubated with non-specific RNA competitors, and then passed through a WNV 3' (−) SL RNA affinity column several times (4, 5). The column was washed and the bound proteins eluted. Each eluted fraction was concentrated with a Centricon-30 and assayed for viral RNA binding activity by gel-mobility shift and UV-induced cross-linking assays. FIG. 1 shows the analysis of WNV 3'(−) SL RNA-binding proteins in fractions eluted from an agarose-adipic acid hydrazide RNA affinity column. FIG. 1-A, Gel-shift assays, Lane 1, free probe; lane 2, final flow-through fraction from the RNA-affinity column; lane 3, first binding buffer wash fraction; lane 4, 0.2 M NaCl wash fraction; lanes 5 and 6, fractions eluted with 1 or 2 M NaCl respectively; lanes 7 and 8, fractions eluted from a "beads-only" control column with 1 or 2 M NaCl, respectively. For each of the fractions, 1 μl of a total of 100 μl was analyzed on the gel. The positions of the three RPCs are indicated by arrows. B. Coomassie blue staining of the eluted fractions from an agarose-adipic acid hydrazide RNA affinity column. Lane 1, aliquot of sample loaded on the affinity column (10 μl of 3 ml); lane 2, fraction eluted with 2 M NaCl from a "beads only" a control column (30 μl of 100 μl); lane 3, fraction eluted with 2 M NaCl from the RNA-affinity column (30 μl of 100 μl). The positions of the eluted proteins are indicated by arrows. The protein markers are shown on the left side of the gel. M, multimer of the probe; fp, free probe.

Little or no specific binding activity was detected in the flow-through fraction by gel-mobility shift assay (FIG. 1A, lane 2) or in the wash fractions (FIG. 1A, lanes 3 and 4). The majority of the RNA binding activity was eluted with 2 M NaCl (FIG. 1A, lane 6). Proteins in aliquot of the eluate was separated by 10% SDS-PAGE, transferred to a nitrocellulose membrane and stained with GoldBlot. Bands with molecular masses similar to those of three of the expected proteins (p60, p50 and p42), as well as some background bands were observed (data not shown). The p42 band was clearly the strongest band. The remainder of the eluted protein was then electrophoresed on one lane of a 10% SDS-PAG and then stained with Coomassie blue (FIG. 1B, lane 3). The p42 and p50 bands were excised from the gel and peptides were generated by trypsin digestion. The peptides were separated by HPLC and the sequences of selected peptides were determined by automated liquid chromatography-tandem mass spectrometry (Beckman Research Institute of the City of Hope). Insufficient unique sequence for p50 was obtained to allow the identification of this protein. The sequences of four peptides obtained from p42 were identical to sequences found in both TIA-1 and TIAR, while the sequences of two additional p42 peptides were unique to TIAR. TIAR and TIA-1 are closely related RNA binding proteins that bind U-rich sequences interspersed with As (15). Both proteins contain three N-terminal RRM domains, each approximately 100 amino acids in length, and a C-terminal auxiliary domain of approximately 90 amino acids (1). TIAR and TIA-1 share 80% overall amino acid identity, with the highest degree of similarity in RRM domain 3 (91% identity) and the lowest degree of similarity (about 50% identity) in the C-terminal auxiliary domain. The data suggest that p42 is TIAR. However, because of the high degree of sequence homology between TIAR and TIA-1, the possibility that TIA-1 also binds specifically to the WNV 3' (−) SL RNA could not be ruled out.

Studies to identify the other three cell proteins that bind to the WNV 3' (−) RNA are in progress. Previous preliminary studies showed that neither anti-EF-1α nor anti-La antibody produced a supershift when added to S100 cytoplasmic extracts incubated with the WNV 3' (−) SL RNA probe (Li and Brinton, unpublished data).

Example 3

Confirmation that TIAR and TIA-1 Bind to the WNV 3' (−) RNA

Figure 2:
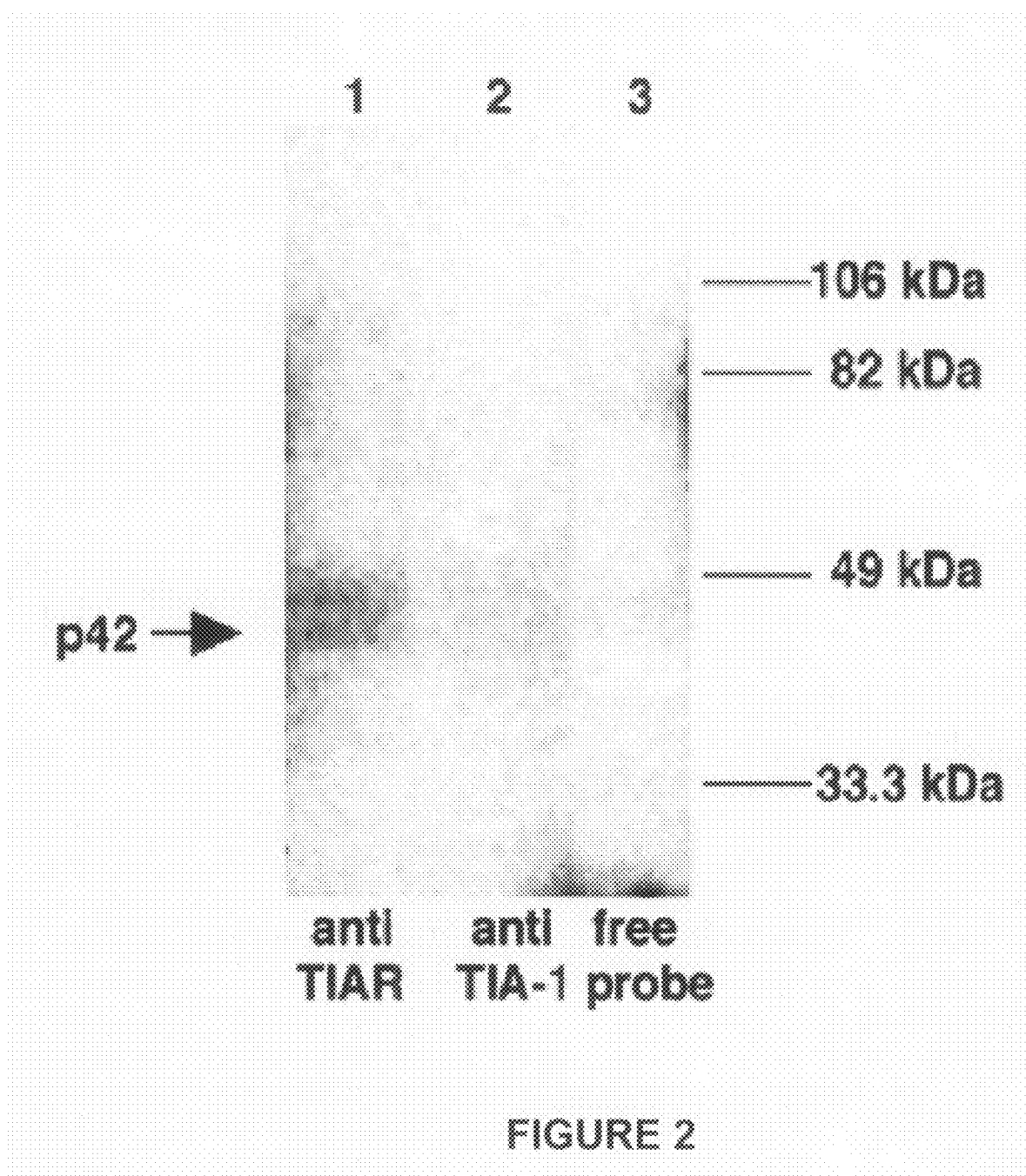
FIG. 2 shows immunoprecipitation of UV-induced cross-linking RNA-protein complexes by protein specific antibodies.

Anti-TIAR (6E3) and anti-TIA-1 (ML-29) antibodies were used to immunoprecipitate UV-induced crosslinked WNV 3' (−) SL RNA-protein complexes from BHK S100 cytoplasmic extracts after treatment with RNase. Results from this experiments are shown in FIG. 2. BHK S100 cytoplasmic extracts from BHK cells were incubated with a $^{32}$P-labeled WNV 3'(−) SL RNA probe. The complexes were cross-linked by exposure to UV light, treated with RNase and then precipitated with anti-TIAR or anti-TIA-1 antibody. The precipitates were analyzed by 10% SDS-PAGE. Lane 1, anti-TIAR antibody was added; lane 2, anti-TIA-1 antibody was added; lane 3, free probe. The expected UV-induced cross-linked p42 product is indicated by an arrow. The protein markers are shown on the right side of the gel. Even though four cell proteins (p108, p60, p50, and p42) that crosslinked to the viral RNA probe were present in these extracts, only the anti-TIAR antibody precipitated the p42-WNV 3' (−) SL RNA complex (FIG. 2, lane 1). Anti-TIA-1 antibody also precipitated the p42-WNV 3' (−) SL RNA complex (FIG. 2, lane 2). However, the band obtained after immunoprecipitation with anti-TIA-1 antibody was not as strong as that seen with the anti-TIAR antibody. These data suggest that the p42 band detected in UV crosslinking experiments with S100 extracts contained both TIAR and TIA-1.

Example 4

Analysis of the Specificities of the Viral RNA-Cell Protein Interactions

Purified GST-TIAR and GST TIA-1 fusion proteins (41) were tested for their ability to bind to the WNV 3' (−) SL RNA in a gel mobility shift assay. The results of preliminary experiments showed that at least a four times higher concentration of GST-TIA-1 was required to detect binding in gel mobility shift assays as compared to GST-TIAR (data not shown). Therefore, different concentrations of GST-TIA-1 (200 nM) and GST-TIAR (50 nM) were used for the representative competition gel shift assays shown in FIGS. 3 A and B. Although the predominant gel shift band observed with both of the fusion proteins migrated to the middle of the gel, additional slower and faster migrating complexes were also observed. The slower migrating bands most likely contain aggregated complexes, since the density of these bands increased with increasing protein concentration (data not shown). The faster migrating bands most likely contained breakdown fragments that retained the RRM2 region containing the viral RNA binding site (see FIGS. 3, C and D).

FIG. 3 shows the analysis of the specificities of the interactions between the WNV 3'(−) SL RNA and the recombinant TIAR or TIA-1 proteins. FIG. 3-A. Competition gel-shift assays with a purified GST-TIA-1 fusion protein. Lane 1, free probe; lane 2, probe plus 200 nM of purified GST-TIA-1 fusion protein; lanes 3 to 14, probe plus 200 nM of purified GST-TIA-1 fusion protein and the indicated competitor RNA. FIG. 3-B. Competition gel shift assays with a purified GST-TIAR fusion protein. Lane 1, free probe; lane 2, probe plus 50 nM of purified GST-TIAR fusion protein; lanes 3 to 14, probe plus 50 nM of purified GST-TIAR fusion protein and the indicated competitor RNA. SC, specific competitor-unlabeled 75 nt WNV 3'(−) SL RNA; M, multimer of the probe; fp, free probe. FIG. 3-C. Purified GST-fusion proteins (500 nM), each containing a single RRM domain of TIA-1, were analyzed by gel mobility shift assay. Lane 1, free probe; lane 2, probe plus the GST-TIA-1 RRM1; lane 3, probe plus the GST-TIA-1 RRM 2; lane 4, probe plus the GST-TIA-1 RRM3. M, multimer of the probe; fp, free probe. FIG. 3-D. Purified GST-fusion proteins (200 nM), each containing a single RRM domain of TIAR, were analyzed by gel mobility shift assay. Lane 1, free probe; lane 2, probe plus the GST-TIAR RRM1; lane 3, probe plus the GST-TIAR RRM2; lane 4, probe plus the GST-TIAR RRM3.

Figure 3A:
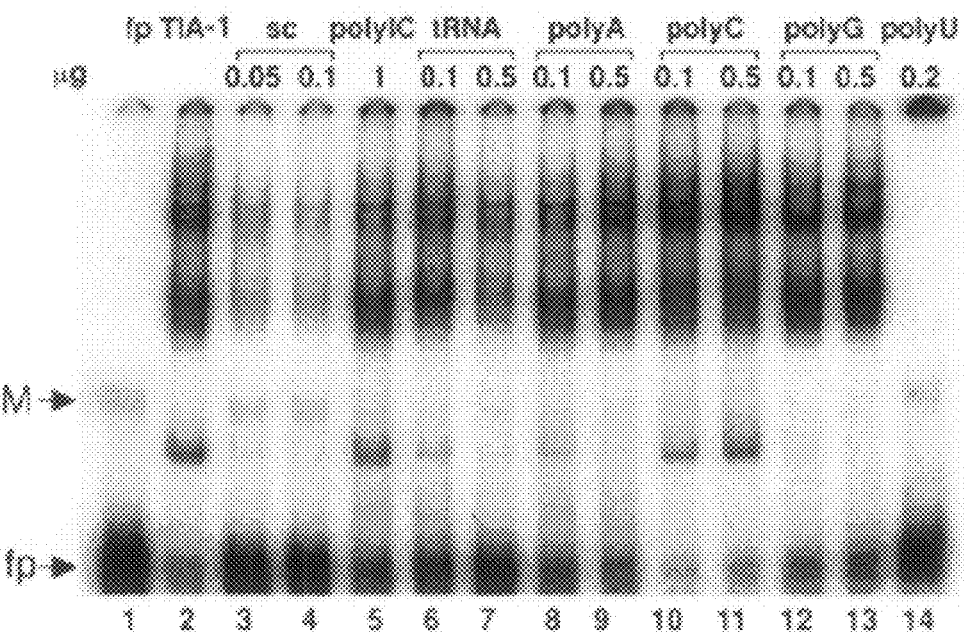
FIG. 3 A-D shows analyses of the specificity of the interactions between the WNV 3'(−) SL RNA and recombinant TIAR or TIA-1 proteins.
Figure 3B:
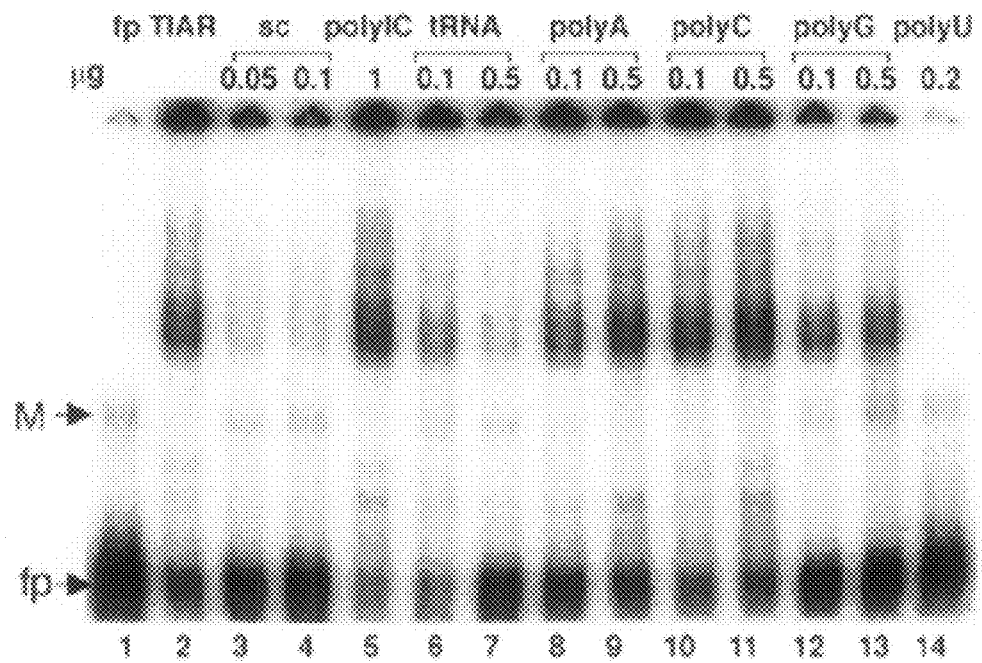
Figure 3C:
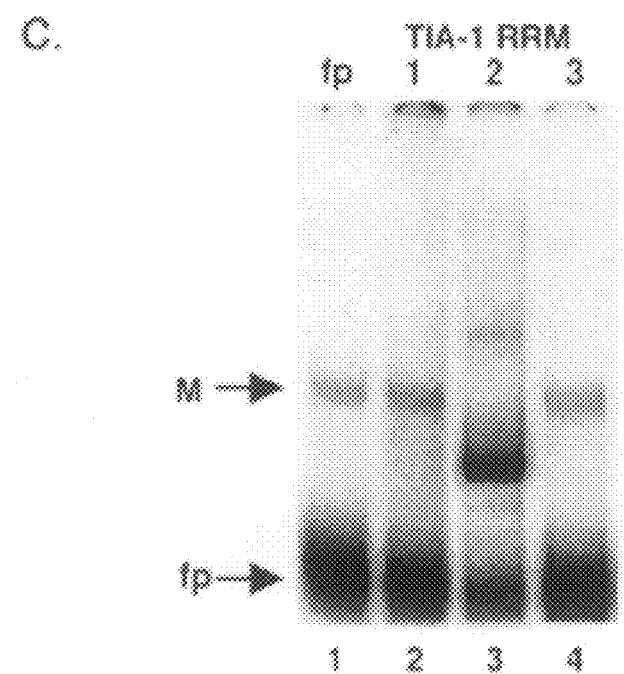
Figure 3D:
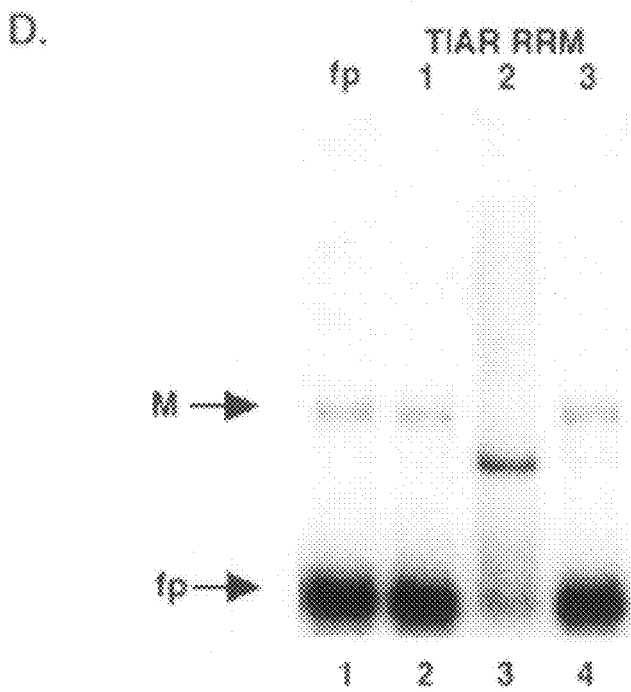

Unlabeled WNV 3' (−) SL RNA (50 or 100 ng) was used as the specific competitor and competed efficiently with the labeled probe (FIG. 3A, lanes 3 and 4; FIG. 3B, lanes 3 and 4). The nonspecific competitors, poly (IC), poly (A), poly (G), and poly (C), showed little or no competition even at concentrations of 500 ng or 1 µg (FIGS. 3, A and B). tRNA (100 or 500 ng) partially competed, but with a lower efficiency than the specific competitor (FIG. 3A, lanes 6 and 7 and FIG. 3B, lanes 6 and 7). As expected from previous studies showing that TIAR and TIA-1 bound to U rich sequences (1), poly U competed efficiently (FIG. 3A, lane 14 and FIG. 3B, lane 14). These data indicate that both the GST-TIAR and GST-TIA-1 proteins bind specifically to the WNV 3' (−) SL RNA.

TIA-1 and TIAR each contain three RRM domains. To determine whether one of these RRM domains contains the major binding site for the WNV 3' (−) SL RNA, purified truncated GST fusion proteins, GST-TIA-1 RRM1, GST-TIA-1 RRM2, and GST-TIA-1 RRM3 (FIG. 3C, lanes 2 to 4), and GST-TIAR RRM1, GST-TIAR RRM2, GST-TIAR RRM3 (FIG. 3D, lanes 2 to 4), were tested for their ability to bind to the WNV 3' (−) SL RNA in gel mobility shift assays. Only the GST-TIA-1 RRM2 (FIG. 3C, lane 3) and the GST-TIAR RRM2 (FIG. 3D, lane 3) were able to bind the WNV 3' (−) SL RNA. These data suggest that the major WNV 3' (−) SL RNA binding site in both TIAR and TIA-1 is RRM 2.

Example 5

Determination of the Relative Dissociation Constants ($K_D$) for the Viral RNA-Cell Protein Interactions FIG. 4 shows quantification of the protein-RNA interactions. FIG. 4-A shows a representative gel mobility shift assay done with increasing amounts of the GST-TIA-1 RRM2 protein and a constant amount of WNV 3'(−) SL RNA. Lane 1, free probe; lanes 2 to 9, probe plus the GST-TIA-1 RRM2 in the amounts indicated. M, multimer of the probe; fp, free probe. FIG. 4-B. The percent $^{32}$P-WNV 3'(−) SL RNA bound was plotted against the concentration of TIA-1 to generate a theoretical saturation binding curve. Inset, the data from the saturation binding curve were transformed as described previously (28, 43). The stoichi- ometry of the interaction of TIA-1 with the WNV 3'(−) SL RNA, as determined by the slope of the line in the inset graph, was about 1:1. The dissociation constant was calculated using the equation log (% bound/% unbound)+2=n{log [TIA-1 (nM)]+1}−log $K_d$. The Kd was estimated to be 112 nM for TIA-1. FIG. 4-C. A representative gel mobility shift assay done with increasing amounts of the GST-TIAR RRM2 protein and a constant amount of WNV 3'(−) SL RNA. Lane 1, free probe; lanes 2 to 9, probe plus the GST-TIAR RRM2 in the amounts indicated. FIG. 5-D. The percent $^{32}$P-WNV 3'(−) SL RNA bound was plotted against the concentration of TIAR to generate a theoretical saturation binding curve. Inset, the data from the saturation binding curve were transformed. The Kd was estimated to be 15 nM for TIAR. The stoichiometry of the interaction of TIAR with the WNV 3'(−) SL RNA, as determined by the slope of the line of the inset graph, was about 1:1. M, multiprobe; fp, free probe.

Figure 4A:
FIG. 4 A-D shows quantification of the RNA-protein interactions.
Figure 4B:
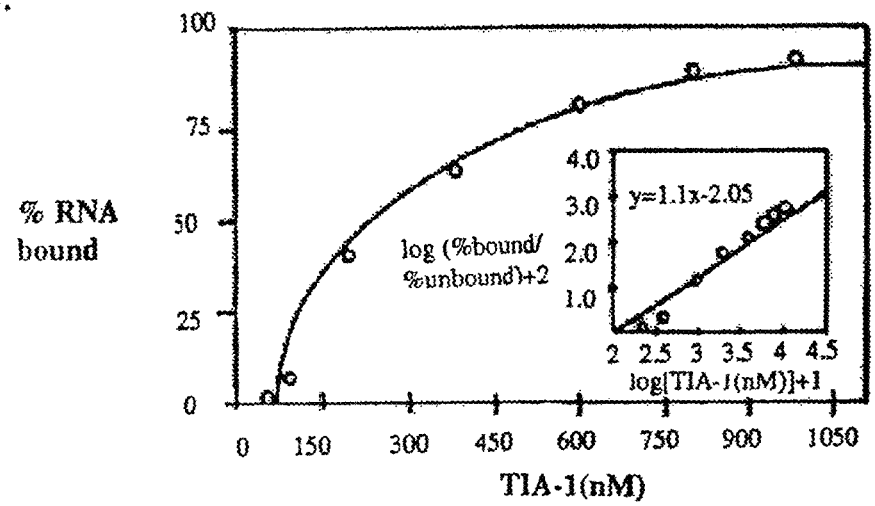
Figure 4C:
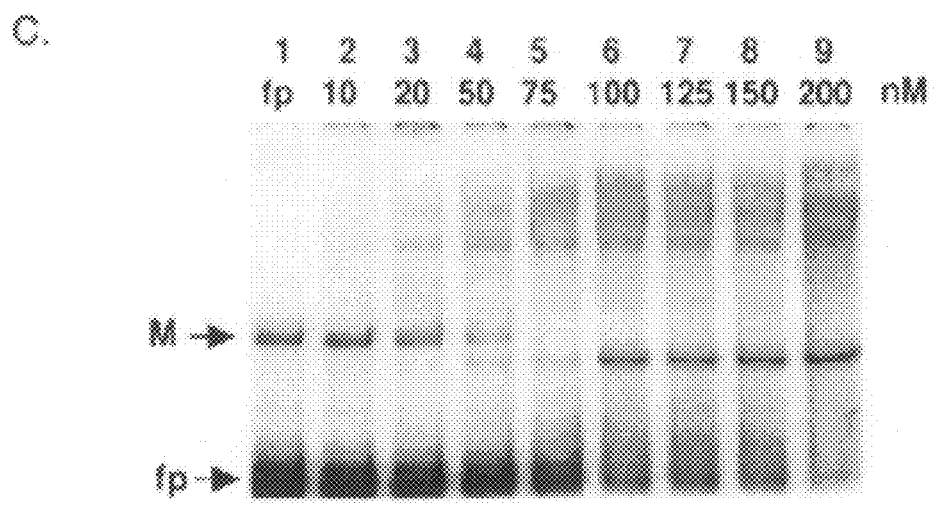
Figure 4D:
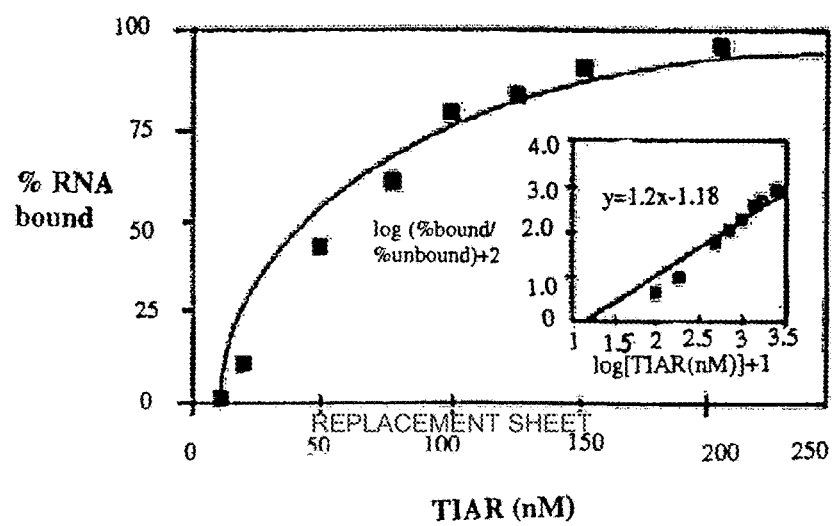

Gel mobility shift assays were performed using different amounts of GST-TIA-1 RRM2 or GST-TIAR RRM2 protein and a constant amount of the $^{32}$P-WNV 3' (−) SL RNA. Although gel shift bands were observed with 10 nM of GST-TIAR RRM2, bands for GST-TIA-1 RRM2 were first observed when 50 nM of protein were used (FIGS. 4A and 4C). A theoretical saturation binding curve was generated by plotting the percentage of bound WNV 3' (−) SL RNA versus the concentration of either GST-TIA-1 RRM2 or GST-TIAR RRM2. The data from the saturation binding curve were transformed as described previously (28, 43). The relative $K_d$ for the interaction between GST-TIA-1 RRM2 and the WNV 3' (−) SL RNA was estimated to be about $1.12 \times 10^{-7}$ M (FIG. 4A), while the relative $K_d$ for the interaction between GST-TIAR RRM2 and the WNV 3' (−) SL RNA was estimated to be about $1.5 \times 10^{-8}$ M (FIG. 4C). The slope (n) of the line represents the ratio of GST-TIA-1 RRM2 or GST-TIAR RRM2 molecules to WNV 3' (−) SL RNA molecules in each RNA-protein complex (FIGS. 4B and D, insets). For both proteins, the slope was calculated to be about 1 (1.1 for TIA-1 and 1.2 for TIAR), suggesting that approximately one TIAR or TIA-1 molecule binds to each WNV 3' (−) SL RNA molecule. Similar $K_d$ and n values were obtained from four independent experiments with standard deviations of +15 nM and +0.15 for GST-TIA-1 RRM2 and +5 nM and +0.1 for GST-TIAR RRM2, respectively. These data indicate that the relative binding activity of the TIAR-RRM2 for the WNV 3' (−) SL RNA is more than 10 times higher than that of the TIA-1-RRM2 for the same RNA. Although the RRM2 domain was shown to contain the main binding site for the viral RNA (FIG. 3), both proteins also contain two additional RRM domains that are likely to participate in stabilizing the RNA-protein interaction. The relative binding activities of the complete proteins for the viral 3' RNA therefore would be expected to be somewhat higher.

Example 6

Effect of TIAR and TIA-1 on the Replication of WNV

Figures 5A, 5B:
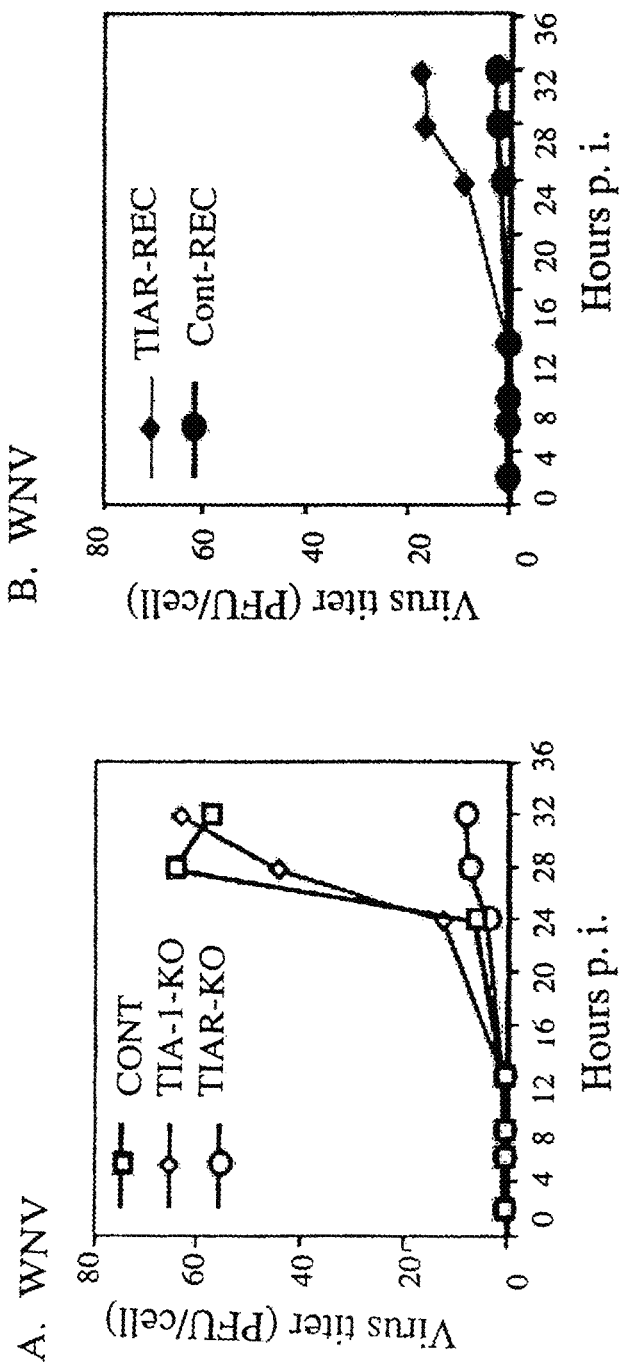
FIG. 5 A-F are graphs showing the growth of virus in TIAR or TIA-1-knockout cell lines.
Figure 5C:
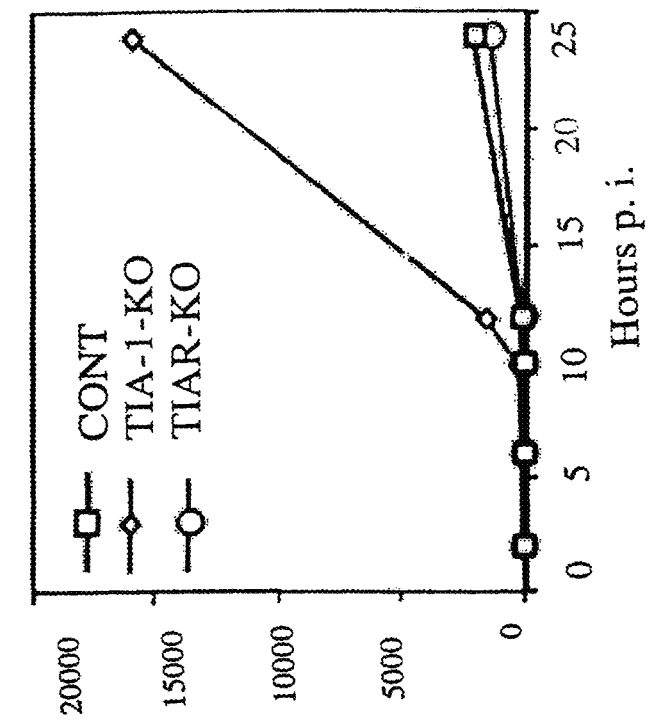
Figure 5D:
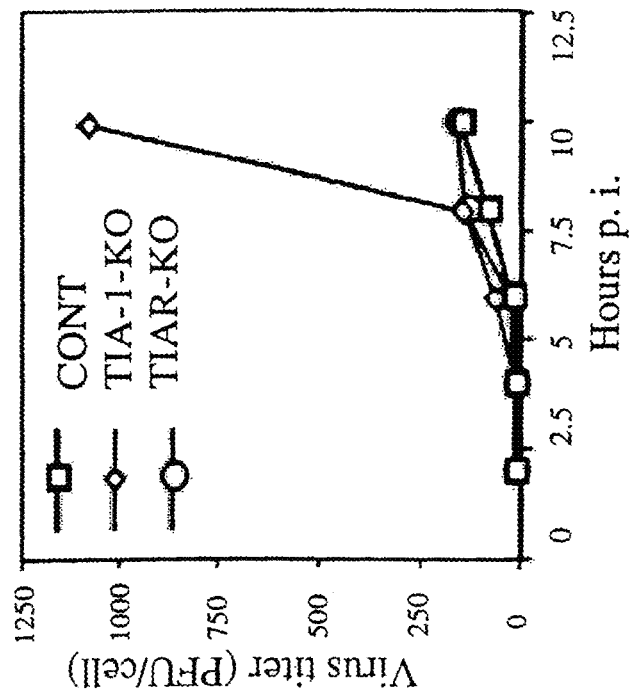
Figure 5E:
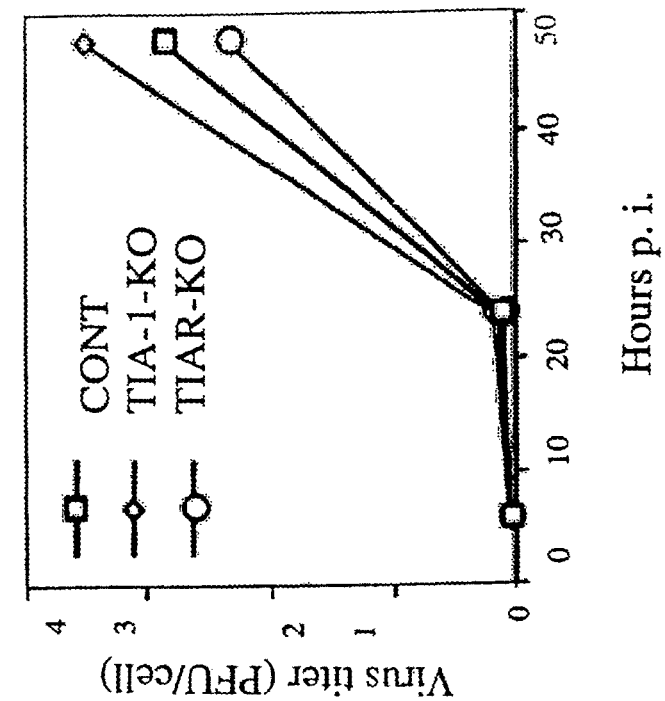
Figure 5F:
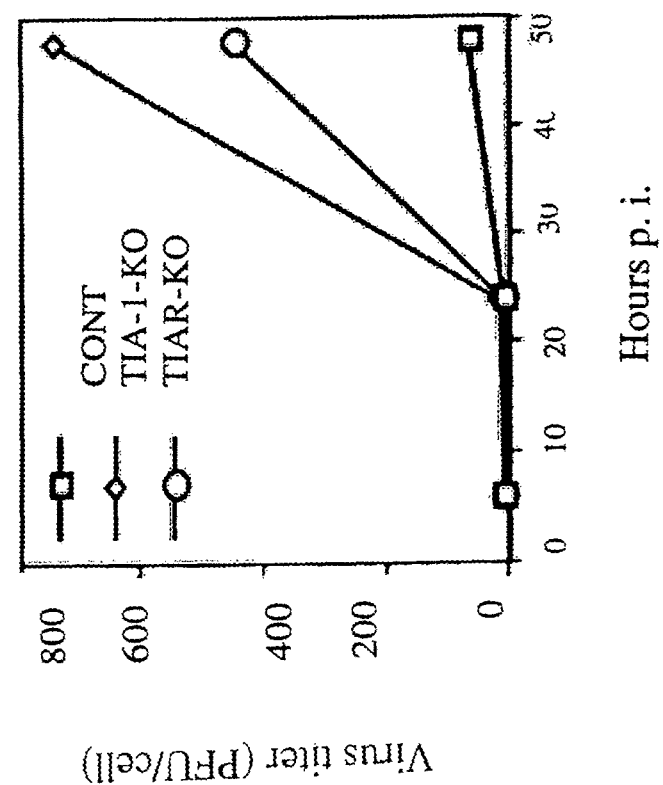

As one means of assessing the effect of the TIAR and TIA-1 proteins on WNV replication, virus growth was compared in TIAR-knockout, TIAR-reconstituted, TIA-1-knockout, and control murine embryo fibroblast cell lines. Confluent cell monolayers were infected with WNV at an MOI of 1. Culture fluid samples were taken at 2, 8, 12, 24, 28, and 32 hr postinfection (p.i.). A representative growth curve of WNV in wild type (W4), TIAR-knockout (NaR4), and TIA-1-knockout ($a^{-/-}43$) cells is shown in FIG. 5A. Virus titers were expressed as PFU/cell, because the various cell lines grew to different but characteristic densities when confluent. The peak titer of WNV produced by TIAR-knockout cells was significantly lower (6-8 fold) than that produced by control cells (FIG. 5A). WNV grew to comparable peak titers in TIA-1-knockout cells and control cells, but peak virus levels were not attained until 6 hr later in TIA-1-knockout cells. Similar results were obtained with an additional set of separately derived control and knockout cell lines (data not shown) suggesting that the decrease in WNV replication observed in the knockout cells was not due to a peculiarity of a single cell line.

The efficiency of infection of these cells with WNV was investigated by indirect fluorescence. Control, TIAR-knockout and TIA-1 knockout cells were infected with WNV for 24 h, 28 h, or 32 h, fixed, and then stained with Hoechst dye and anti-WNV antibody. At 24 hr post infection, bright virus-specific perinuclear staining was observed in about 40% of the control and TIA-1-knockout cells. However, the stained perinuclear areas in the infected control cells were generally wider than those in the TIA-1-knockout cells. Although a similar percentage of TIAR-knockout cells showed virus-specific perinuclear staining at 24 hr, the fluorescence in these cells was faint and the areas of staining were focal. The intensity of the perinuclear staining in the infected TIAR-knockout cells increased somewhat by 28 h post infection and thin perinuclear rings were observed in some cells. At 32 h, although the intensity and distribution of the fluorescence had increased in the WNV-infected TIAR-knockout cells, only about 10-20% of the cells contained broad, brightly stained perinuclear rings. These results suggest that WNV infects similar numbers of cells in the three types of cultures but that virus replication is most efficient in the control cells, slightly less efficient in the TIA-1-knockout cells and least efficient in the TIAR-knockout cells.

Example 7

Growth of Other Types of Viruses in TIAR-Knockout and TIA-1-Knockout Cells

To determine whether other types of viruses also showed reduced growth in TIAR-knockout cells, control, TIAR-knockout, and TIA-1-knockout cells were infected with Sindbis virus, vaccinia virus, VSV or HSV-1 at an MOI of 1. Sindbis virus is another plus strand RNA virus but from the alpha togavirus family. VSV, a rhabdovirus, is a minus strand RNA virus, while vaccinia, a poxvirus, is a DNA virus. Similar to WNV, these three viruses replicate in the cytoplasm of infected cells. HSV-1, a herpes virus, is a DNA virus that replicates in the nucleus. Culture fluid samples were harvested at the indicated times after infection and titered by plaque assay. Representative growth curves obtained for each of the viruses are shown in FIG. 5C through F. Confluent monolayers of control (W4), TIA-1-knockout ($a^{-/-}43$) and TIAR-knockout (NaR4) cells were infected with (A) WNV, (C) VSV, (D) Sindbis virus, (E) HSV-1, or (F) vaccinia virus at an MOI 1. Confluent monolayers of control (W4), TIAR-reconstituted (TIAR-Rec) or control reconstituted (Cont-Rec) cells were infected with (B) WNV at MOI 1. Culture fluid samples were taken at the indicated hours post-infection (p. i.) and titered by plaque assay.

Figures 6A, 6B:
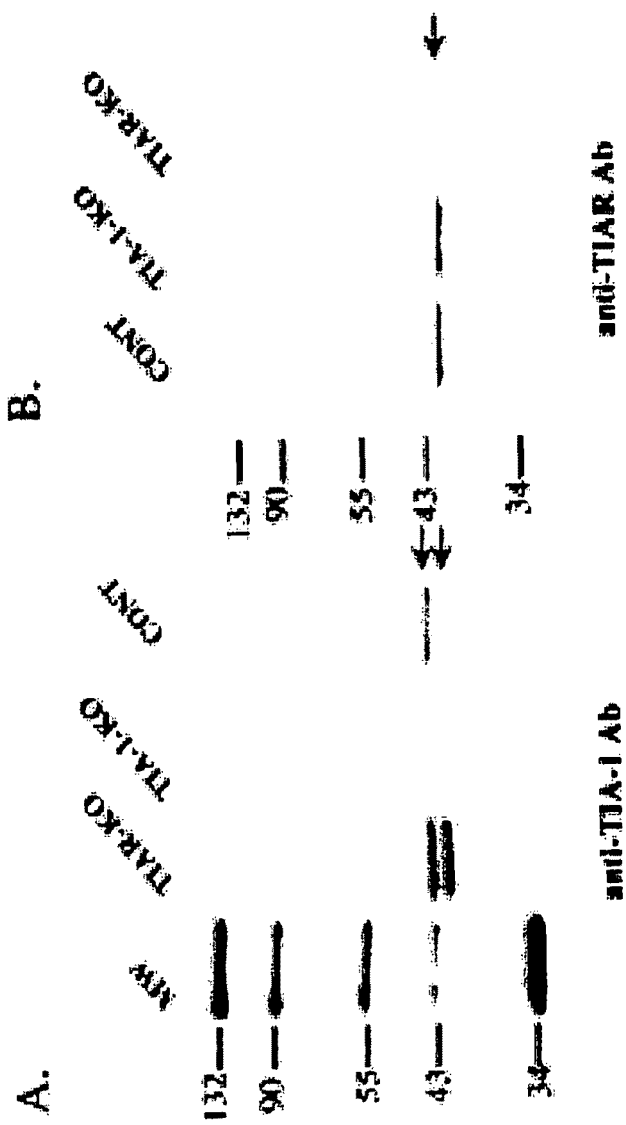
FIG. 6 A-F shows Western blot analyses of the amounts of TIAR and TIA-1 proteins in various cell lines.
Figure 6C:
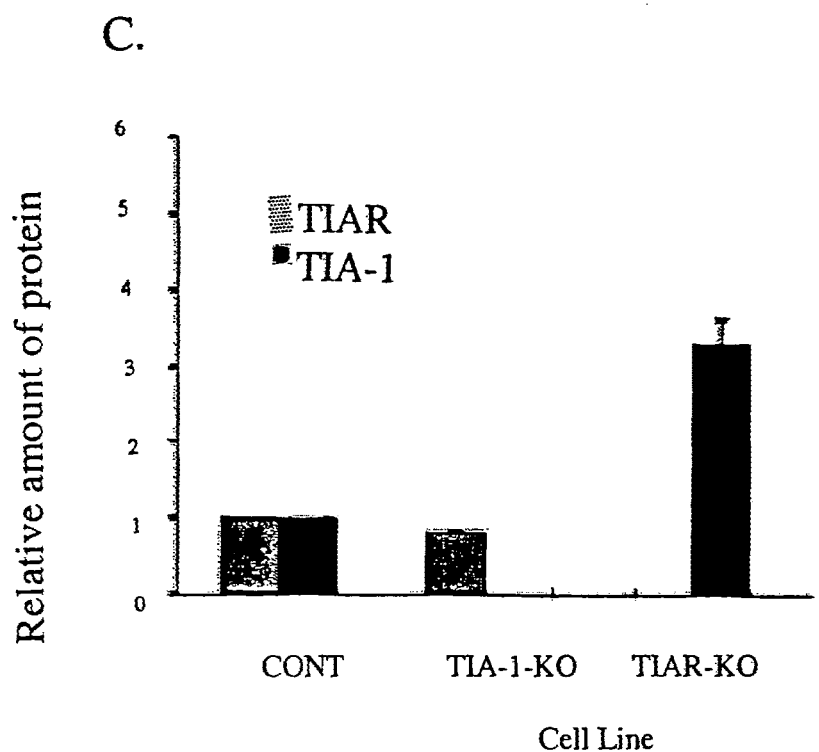
Figures 6D, 6E:
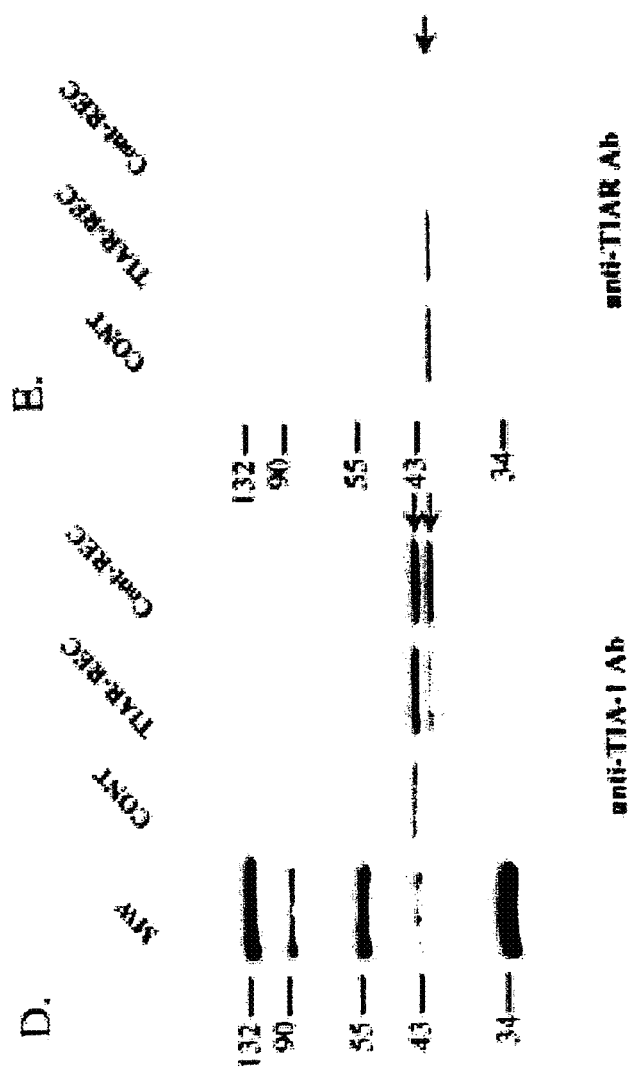
Figure 6F:
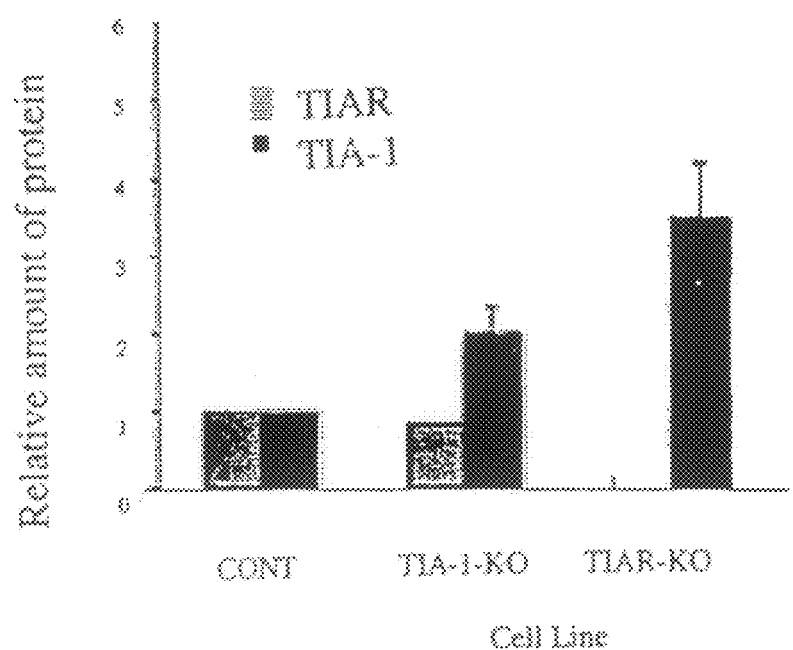

VSV (FIG. 5C) and Sindbis virus (FIG. 5D) grew to similar titers in TIAR-knockout and control cells, whereas in TIA-knockout cells, both of these viruses grew to significantly higher titers suggesting that the presence of TIA-1 had a negative effect on the growth of these viruses. HSV-1 also grew to significantly higher levels in TIA-1 knockout cells than in control cells (FIG. 6E). However, the growth of HSV-1 in TIAR-knockout cells was also more efficient than in control cells, but not as efficient as in TIA-knockout cells. The efficiency of growth of vaccinia virus (FIG. 5F) in all three types of cells was similar. Because the majority of the vaccinia progeny virus is cell associated, the extracellular virus titers detected were significantly lower than those for the other viruses. These results indicate that only the growth of WNV was less efficient in the TIAR-knockout cells.

To further investigate the effect of TIAR on viral growth, the growth of WNV in a TIAR-reconstituted stable cell line, TIAR-REC, was tested. Another stable cell line, Cont-REC, which had been transfected with the same vector, but did not express TIAR at detectable levels (FIG. 6E), was used as a control for possible nonspecific effects of the vector. FIG. 5B shows representative WNV growth curves obtained with control, TIAR-REC and Cont-REC cells. Although the peak titer of WNV produced by TIAR-reconstituted cells was higher than that produced by Cont-REC cells, it was lower than that produced by control cells.

Example 8

Comparison of the Relative Amounts of TIAR and TIA-1 Proteins in the Various Cell Lines The relative amounts of TIAR and TIA-1 in cytoplasmic extracts from each of the cell lines were estimated by immunoblotting using protein-specific antibody. Previous studies showed that two isoforms generated by alternative splicing exist for both TIA-1 and TIAR (1). The two TIA-1 isoforms, 42 kDa TIA-1a and 40 kDa TIA-1b, differ from each other by an 11 amino acid deletion. These isoforms are usually found in cells in a 1:1 ratio. The two TIAR isoforms, 42 kDa TIARa and 40 kDa TIARb, differ from each other by a 17 amino acid deletion. Because TIARb is six times more abundant in cells than TIARa, it is the only isoform that is detected by Western blotting. Representative Western blots are shown (FIGS. 6A, B, D, and E). Twenty 1 µg of total cell protein were run on each lane. The TIAR protein and two isoforms of the TIA-1 protein are indicated by arrows. Quantification of the relative amounts of protein in the various types of cells is shown in FIGS. 6 C and F. The relative amount of each protein in the control cells was defined as 1. The relative amounts of the proteins in other cell lines were expressed as the ratio of the protein band intensity divided by the density of the band in control cells. The values shown are means of the values obtained from 3 to 5 separate experiments.

As expected, no TIA-1 protein was detected in cytoplasmic extracts from TIA-1-knockout cells (FIG. 6A) and no TIAR protein was detected in cytoplasmic extracts from TIAR-knockout cells (FIG. 6B). The level of the TIAR protein in cytoplasmic extracts from TIA-1 knockout cells ($a^{-/-}43$) was slightly decreased (FIG. 6B), but the amount of TIA-1 protein in the cytoplasm of TIAR-knockout cells was significantly increased (by 3.3 fold) as compared to the amounts of these proteins present in the control (W4) cells (FIGS. 6A and C). These data indicate that the level of TIA-1 is down-regulated by TIAR. No significant differences in the cytoplasmic levels of either protein were observed after WNV infection (at 5 or 8 hr p.i.) in the various cell lines tested (data not shown).

The amount of TIAR protein detected in the TIAR-REC cells was about 80% of that detected in control (W4) cells (FIGS. 6E and F), while no TIAR protein was detected in Cont-REC cells (FIG. 6E). The amount of TIA-1 protein in the TIAR-REC cells was 2 fold higher, while the amount of TIA-1 protein in Cont-REC cells was 3.5 fold higher, as compared to controlW4 cells (FIGS. 6D and F). These data indicate that the TIAR-REC cells had intermediate levels of the two proteins.

Example 9

Comparison of TIAR and TIA-1 cDNA Sequences from Cells Obtained from Flavivirus Resistant and Susceptible Mice A single, dominant gene, Flv, that maps to chromosome 5 confers a flavivirus resistance phenotype in mice. Data from previous studies showed that resistant mice as well as cells obtained from a number of different tissues of resistant mice produced significantly lower titers of flaviviruses than did congenic susceptible mice or cells and that genomic RNA levels, but not minus strand viral RNA levels, were lower in resistant cells (7; Li and Brinton, unpublished data). Since both TIAR and TIA-1 bind to the WNV 3'(−)SL RNA and this SL is located at the site of initiation of genomic RNA synthesis, it was of interest to determine whether the sequences of TIAR and TIA-1 cDNAs differed in cells from resistant C3H/He and congenic susceptible C3H.RV mice. Cell RNA was extracted from resistant and susceptible embryo fibroblasts with TRIZOL-LS (Life/Gibco) according to the manufacturer's instructions. Using primers designed from mouse (strain 129 SVJ) TIA-1 and TIAR cDNA sequences previously reported by Beck et al. (1996), cDNAs were amplified by RT-PCR from cell mRNA and TA cloned into pCR 2.1-TOPO (Invitrogen). At least three cDNA clones for each isoform were sequenced. The sequences obtained for the two TIAR isoform cDNAs and for the two TIA-1 isoform cDNAs from resistant C3H.RV were identical to those of the comparable isoforms obtained from susceptible C3H/HE cells. These sequences were also identical to the previously reported sequences for these proteins from 129SVJ mice (Accession numbers: U55861 and U55862) by Beck et al. (1). Also, as assessed by Western blotting, the expression levels of the TIAR and TIA-1 proteins in resistant cells and susceptible cells were similar. These data indicate that neither TIAR nor TIA-1 is the product of the Flv gene.

Example 10

Cloning, Expression, and Purification of Recombinant TIA-1 and TIAR from E. coli TIA-1b and TIARa cDNAs were amplified by RT-PCR from C3H/He mouse embryo fibroblasts, cloned into the TA cloning vector pCR 2.1 (Invitrogen) and then subcloned into the pCRT7/CT-TOPO (Invitrogen) expression vector to generate pTIA-1b and pTIARa. The expressed protein contained a C-terminal (His)6-tag. All inserts were verified by restriction and sequence analysis. Recombinant TIA-1 and TIAR proteins were expressed in E. coli Rosetta (DE3) pLysS cells (Novagen) as follows. Cells were transformed with plasmid DNA (10 ng) and grown in LB media containing carbenicillin (50 µg/µl) and chloramphenicol (34 µg/µl) to an OD600 of 0.6 at 37° C. Protein expression was induced by the addition of 0.05 mM isopropyl-β-D-thiogalactopyranoside (IPTG) for 5 hr with continuous shaking at 37° C. To purify proteins to near homogeneity, a one or two step purification protocol was used. For the two step purification, cell pellets from a 0.5 liter culture were resuspended in Buffer A (20 mM sodium phosphate, pH 7.0) containing protease inhibitor cocktail (Complete Mini, EDTA free, Roche) and then lysed with a SLM-Aminco French pressure cell press (Heinemann) at 20,000 psi. The clarified supernatant was loaded onto an anion exchange column (Superdex 200 Q column, Amersham Pharmacia Biotech) on an AKTA FPLC system (Amersham Pharmacia Biotech). The column was first washed extensively with Buffer A and then bound proteins were eluted with a salt gradient (0.1-1M KCl) in Buffer A. The recombinant proteins eluted at 200 mM KCL. Fractions containing recombinant protein were pooled and further purified on a cobalt column (Talon metal affinity resin, Clontech). The column was washed with 1× Extraction/Wash Buffer (50 mM sodium phosphate, 300 mM NaCl2, PH 7.0) containing 15 mM imidazole. Proteins were eluted with 1× Extraction/ Wash Buffer containing 150 mM imidazole. For one step purification, cell lysates were added directly to the cobalt column. The eluted protein fractions were combined, dialyzed against Storage buffer (20 mM sodium phosphate, 30 mM KCl, 1 mM MgCl2, 0.5 mM EDTA, and 15% Ficoll 400), aliquoted, and stored at −80° C. The protein concentration was measured using a Coomassie Plus Protein Assay Reagent kit (Pierce) with a bovine serum albumin (BSA) protein standard. Proteins in eluted fractions were analyzed by 10% SDS-PAGE and detected by Coomassie blue staining. Recombinant eukaryotic elongation factor 1 alpha (eEF-1a) containing a C-terminal 6×His tag was expressed in E. coli Rosetta (DE3) pLysS cells (Novagen) and partially purified on a cobalt column (Talon metal affinity resin, Clontech).

Western Blot Analysis.

Bacterial cells were lysed in a buffer containing 1×PBS, 0.5% sodium deoxycholate, and 0.1% SDS and centrifuged to remove cell debris. Purified proteins were separated by 10% SDS-PAGE and electrophoretically transferred to nitrocellulose filter membranes (0.2 µm pore size; Micron Separations, Inc.). The membranes were blocked with 5% non-fat dry milk in Tris-buffered saline (TBS) (10 mM Tris HCl PH 8.0, 100 mM NaCl) with continuous rocking at 4° C. overnight. The membranes were incubated with polyclonal antibodies (diluted 1:200 in TBS containing 5% non-fat dry milk) directed against the unique C-terminal regions of TIA-1 or TIAR (Santa Cruz Biotechnology) for 1 hr at room temperature with constant rocking. The immunoblots were then washed three times with 1×TBS containing 0.1% Tween-20 and incubated with anti-rabbit immunoglobulin G antibody conjugated with horseradish peroxidase (1:2000) (Santa Cruz Biotechnologies). After washing, the specific proteins were detected using the Super Signal chemiluminescent detection system (Pierce) and autoradiography on X-Omat film (Kodak).

DNA Constructs Used as Templates for RNA Synthesis.

The construction of a plasmid containing the first 75 nts of the WNV5' NCR (p5'NCR) was previously described (Shi et al., 1996). This plasmid was amplified by PCR to provide the DNA templates used for in vitro transcription of WNV3' (−)SL and WNV5'(+)SL RNAs. Mutant constructs were generated using the Quick-Change Site-Directed Mutagenesis kit (Stratagene) according to the manfacturer's protocol.

DNA extracted from selected positive colonies was sequenced to confirm the presence of the introduced mutations and/or deletions. pWNV-Trun (Elghonemy et al., 2005) was used to amplify DNA templates for the in vitro synthesis of the 3' terminal 89 nts of the WNV genome. The primers used for RNA synthesis and site-directed mutagenesis are available from the authors upon request.

In Vitro Transcription of 32P-Labelled and Unlabeled RNA

WNV3'(−) SL RNA, WNV3'(+)SL RNA, WNV5'(+)SL RNA, and a number of WNV3'(−)SL mutant RNAs were in vitro transcribed using a MAXIscript in vitro transcription kit (Ambion) in 20 μl reactions that contained T7 RNA polymerase (30 U), a PCR-amplified product (1 μg) purified with a Qiaquick Gel Extraction kit (Qiagen) according to the manufacturer's instructions, 0.8 mM [α-32P] GTP (3000 Ci/mmol, 10 mCi/ml; Amersham Biosciences), 3 μM GTP and 0.5 mM CTP, UTP, and ATP. The in vitro transcription mixture was incubated at 37° C. for 2 hrs and transcription was stopped by addition of DNase I (1U) for 15 min at 37° C. After addition of an equal volume of 1× Gel Loading Buffer II (Ambion), the reaction mixture was heated at 95° C. for 5 min. RNA transcripts were purified by electrophoresis on a 6% PAG containing 7 M urea. The wet gel was autoradiographed and the 32P-labelled RNA band was excised. RNA was eluted from the gel slices by rocking overnight at 4° C. in Elution Buffer (0.5 M NH4OAC, 1 mM EDTA, and 0.1% SDS). The eluted RNA was filtered through a 0.45 μm cellulose acetate filter unit (Millipore) to remove gel pieces, precipitated with ethanol, resuspended in water, aliquoted, and stored at −80° C. The amount of radioactivity incorporated into each RNA probe was measured with a scintillation counter (Beckman LS6500) and the specific activity (calculated as described previously, Blackwell and Brinton, 1997) was routinely about 1.3×107 cpm/μg. Unlabeled viral RNA was in vitro transcribed as described above except that 1 mM of each NTP was added to the reaction mixture. After synthesis, these RNAs were purified on NucAway spin columns (Ambion) and RNA concentrations were calculated based on the UV absorbance measured at 260 nm.

Gel Mobility Shift Assays 32P-labelled WNV3'(−)SL RNA probe was diluted in Binding Buffer (20 mM sodium phosphate, 30 mM KCl, 1 mM MgCl2, 0.5 mM EDTA, 15% Ficoll 400, and 10 U RNasin), denatured at 85° C. for 10 min, and slowly renatured (0.1° C./sec) to 20° C. Reaction mixtures containing the RNA probe (2000 cpm; 0.2 nM) and different concentrations of protein, such as rTIA-1 (50-900 nM), rTIAR (5-90 nM), purified BSA (100-600 nM) (Ambion), or partially purified recombinant eEF-1α (100-600 nM), in a final volume of 10 μl of Binding Buffer plus 10 nM of the nonspecific competitor tRNA were incubated at room temperature for 30 min and the RNA-protein complexes formed were electrophoresed on a 5% non-denaturing PAG at 100 V/hr in 0.5×TBE at 4° C. Gels were dried and visualized by autoradiography. For competition gel-shift assays, purified rTIA-1 (600 nM) and purified rTIAR (60 nM) were incubated with increasing concentrations of the nonspecific competitors, poly I/C (0.1-1 ng) or tRNA (2.5-20 nM), or the specific competitor, unlabeled WNV3'(−) SL RNA (0.2-5 nM), for 10 min prior to the addition of 0.2 nM (2000 cpm) of the 32P-labelled RNA probe. The binding activity of each mutant RNA probe was compared to that of the wild type WNV3'(−)SL RNA probe. The signal intensities of the RNA protein complex and free probe gel bands were quantitated using a Bio-Imaging Analyzer PhosphorImager (Molecular Dynamics). The amount of RNA protein complex was divided by the amount of free probe to determine the percent RNA probe shifted, which was plotted against the rTIA-1 or rTIAR protein concentration used in the reaction. Data points graphed are the average of three replicate binding experiments. Standard deviation of the mean was calculated using the ESTDEV method in Microsoft Excel.

RNA Secondary Structure Prediction

The secondary structure of each RNA probe used in this study was predicted using M-Fold (version 3.1) (Zuker, 2003).

Effect of A and U nucleotides deletions in the mapped WNV3'(−)SL RNA TIA-1 and TIAR binding sites on virus production.

FIG. 8 A-I shows expression, purification, and RNA binding activities of recombinant TIA-1 and TIAR proteins. (A) Induced bacterial cell lysates overexpressing rTIAR (~45 kDa) or rTIA-1 (~47 kDa) after 5 hr of IPTG induction were separated by 10% SDS PAGE and stained with Coomassie blue. (Lane 1) rTIAR (Lane 2) rTIA-1. A putative proteolytic cleavage product (~36-38 kDa) of each recombinant protein is indicated by arrow heads. Purification of rTIA-1 and rTIAR proteins on (B) a cobalt affinity column or (C) by an anion exchange column followed by a cobalt affinity column. Purified proteins were separated by 10% SDS PAGE. Fractions of rTIAR (lanes 1 and 2) and rTIA-1 (lanes 3 and 4) eluted using 150 mM imidazole. (D) Western blot analysis of two-step purified rTIAR (lane 1) or rTIA-1 (lane 2) using anti-TIAR and anti-TIA-1 antibodies, respectively. (E) Gel mobility shift assays done with increasing concentrations of each purified protein and a $^{32}$P-WNV3'(−) SL RNA probe and analyzed on 5% non-denaturing gels. rTIA-1 gel shift assay (Left panel); rTIAR gel shift assay (Right panel). (Lane 1) Free probe (FP) (Lanes 2-8) Probe plus indicated concentration of purified protein. The positions of the RNA-protein complexes (RPC) are indicated by brackets. (F) and (G) Representative competition gel-shift analysis using 600 nM rTIA-1 protein and increasing concentrations of the non-specific competitors poly I/C or tRNA, respectively. (Lane 1) free probe (FP) (Lane 2) Probe with no competitor (Lanes 3-7) Probe plus increasing concentrations of non-specific competitor. (H) Representative competition gel shift analysis using 600 nM rTIA-1 and increasing concentrations of unlabelled WNV3'(−)SL RNA. (Lane 1) FP (Lane 2) Probe without competitor (Lanes 3-5) Probe plus increasing concentrations of unlabelled specific competitor. (I) Representative gel mobility shift assays with increasing concentrations of BSA (upper panel, Lanes 2-4) and recombinant eEF-1α (lower panel, Lanes 2-4) and the WNV 3'(−)SL RNA probe.

FIG. 9 A-G shows analysis of the WNV3'(−)SL RNA structure. Predicted alternative secondary structures, (A) 3'(−)S1 and (B) 3'(−)S2, for the WNV3'(−)SL RNA sequence. (C) The predicted secondary structure of the complementary WNV5'(+)SL RNA (5'(+)S). AG, minimum free energy values calculated for each structure. The three AU-rich loops in 3'(−)S1 (L1, L2, and L3) are indicated by arrows. AU-rich sequences within these loops are shown in bold. Predicted secondary structures of the mutated WNV3'(−)SL RNAs, (D) L2→As and (E) MS2. Mutations within these RNAs are indicated by asterisks. (F) Denaturing (upper panel) and non-denaturing (lower panel) polyacrylamide gels showing the migration of the four $^{32}$P RNA probes. (Lane 1) MS2 (Lane 2) L2→As (Lane 3) WNV5'(+)SL and (Lane 4) Wild type WNV3'(−)SL. (G) Gel mobility shift assays done with increasing concentrations of purified TIA-1 (upper panel) or TIAR (lower panel) and WNV3'(−) SL or MS2 RNA probes. (Lanes 1-5) WNV3'(−) SL probe (Lanes 6-10) MS2 probe. The positions of the RPCs are indicated by brackets.

FIG. 10 A-D shows the effect of C substitutions in L1, L2, and L3 of the WNV3'(−)SL RNA on TIA-1 and TIAR binding activity. (A) Predicted secondary structures of mutant RNAs. Substituted nts are indicated by asterisks. (B) Representative gel mobility shift assays with TIA-1 (upper panel) or TIAR (lower panel) and each mutant RNA probe. (Lanes 1-5) Wild type RNA (Lanes 6-10) L1→Cs RNA (Lanes 11-15) L2→Cs RNA (Lanes 16-20) L1+L2→Cs RNA and (Lanes 21-25) L3→Cs RNA. Gel mobility shift assays were done with increasing concentrations of each purified protein. The average percent RNA probe shifted was calculated from triplicate experiments and plotted against the concentration of recombinant (C) TIA-1 or (D) TIAR. Error bars indicate standard deviation of the mean.

FIG. 11A-D shows the effect of deletions in L1, L2, or L3 of the WNV3'(−)SL RNA on TIA-1 and TIAR binding activity. (A) Predicted secondary structures of mutant RNAs. Only U nucleotides in L1 and UAA in L3 could be deleted and still preserve the predicted RNA secondary structure. Deleted nts are indicated by wedges. (B) Representative gel mobility shift assays with TIA-1 (upper panel) or TIAR (lower panel) and each mutant RNA probe. (Lanes 1-5) Wild type RNA (Lanes 6-10) RNA with Us deleted in L1 (Lanes 11-15) RNA with L2 deleted (Lanes 16-20) RNA with Us in L1 and L2 deleted and (Lanes 21-25) RNA with UAA in L3 deleted. (C) and (D) Percent RNA probe shifted.

Figure 12:
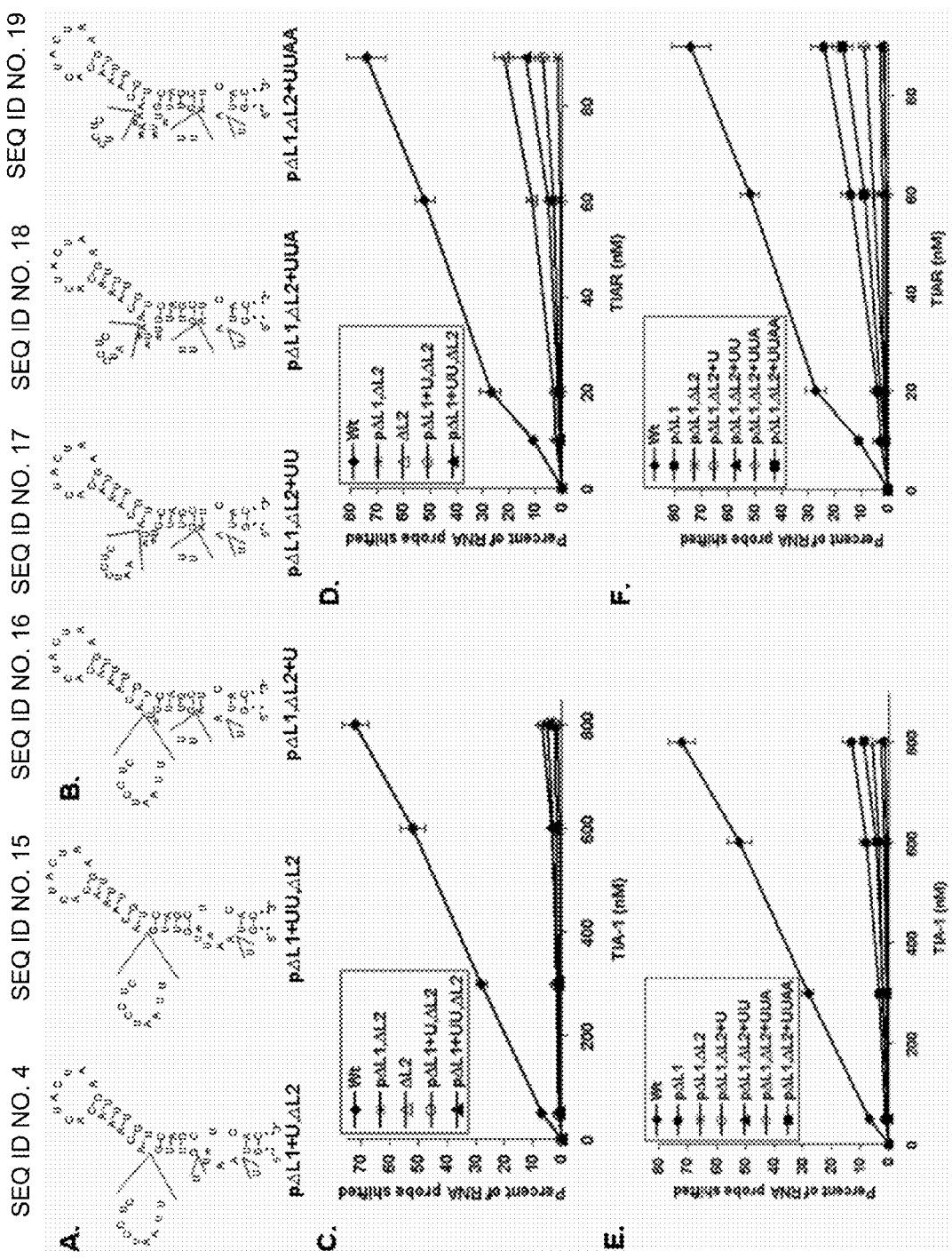
FIG. 12 A-F shows the effect of sequential restoration of deleted nucleotides in L1 and L2 on TIA-1 and TIAR binding activity.

FIG. 12 A-F shows the effect of sequential restoration of deleted nucleotides in L1 and L2 on TIA-1 and TIAR binding activity. Predicted secondary structures of (A) $U_{19}$ or $U_{19}$ plus $U_{20}$ restored (B) $U_{25}$, $U_{26}$, $A_{27}$, and $A_{28}$ sequentially restored into pΔL1, ΔL2 RNA. Restored nucleotides are indicated by asterisks. (C), (D), (E), and (F) Percent RNA probe shifted.

Figure 13:
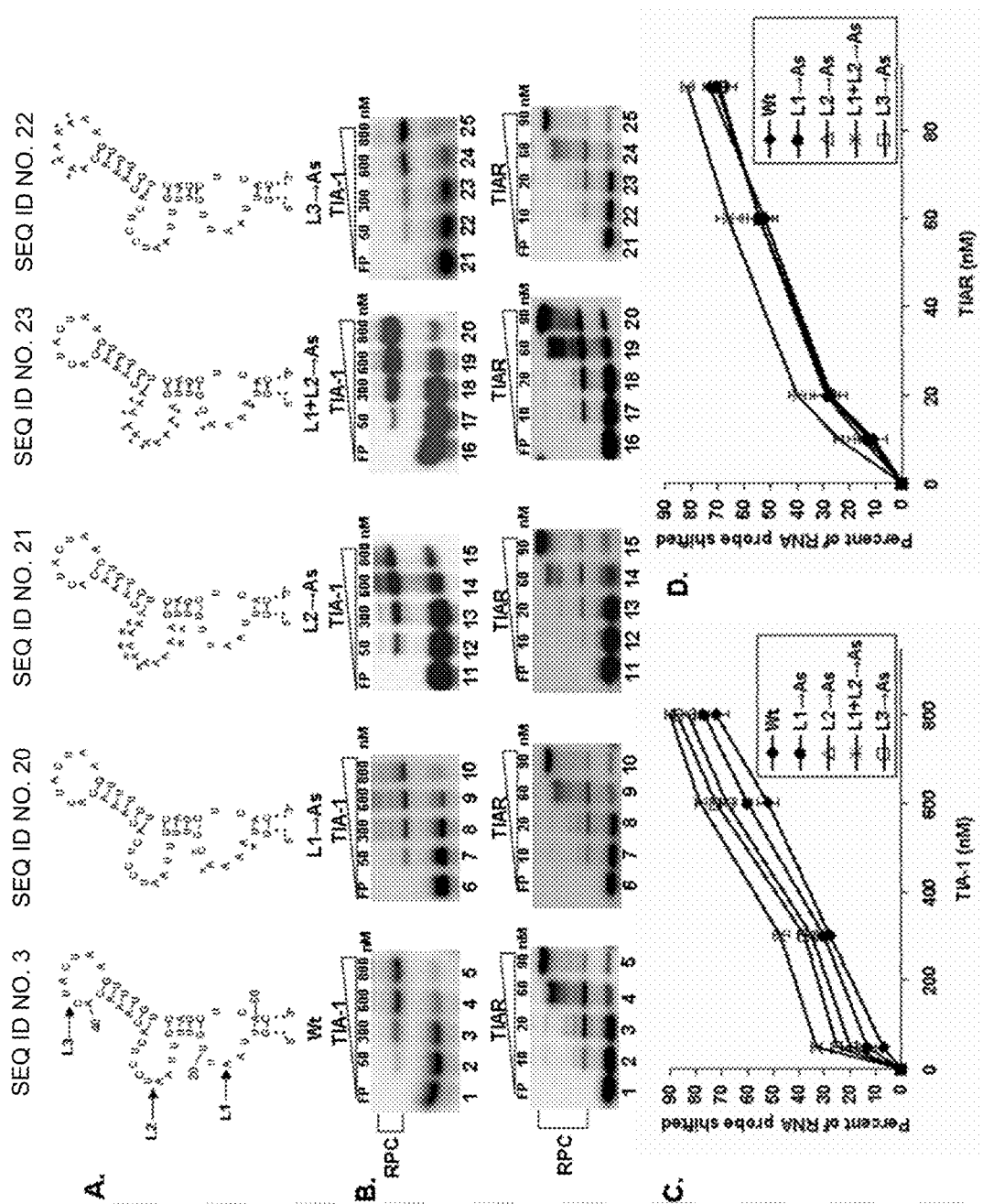
FIG. 13 A-D shows the effect of A substitutions in L1, L2, and L3 within the WNV3'(−)SL RNA on TIA-1 and TIAR binding activity.

FIG. 13 A-D shows the effect of A substitutions in L1, L2, and L3 within the WNV3'(−)SL RNA on TIA-1 and TIAR binding activity. (A) Predicted secondary structures of mutant RNAs. Mutations are indicated by asterisks. (B) Representative gel mobility shift assays with TIA-1 (upper panel) or TIAR (lower panel) and each mutant RNA probe. (Lanes 1-5) Wild type RNA (Lanes 6-10) L1→As RNA (Lanes 11-15) L2→As RNA (Lanes 16-20) L1+L2→As RNA and (Lanes 21-25) L3→As RNA. (C) and (D) Percent RNA probe shifted.

Figure 14:
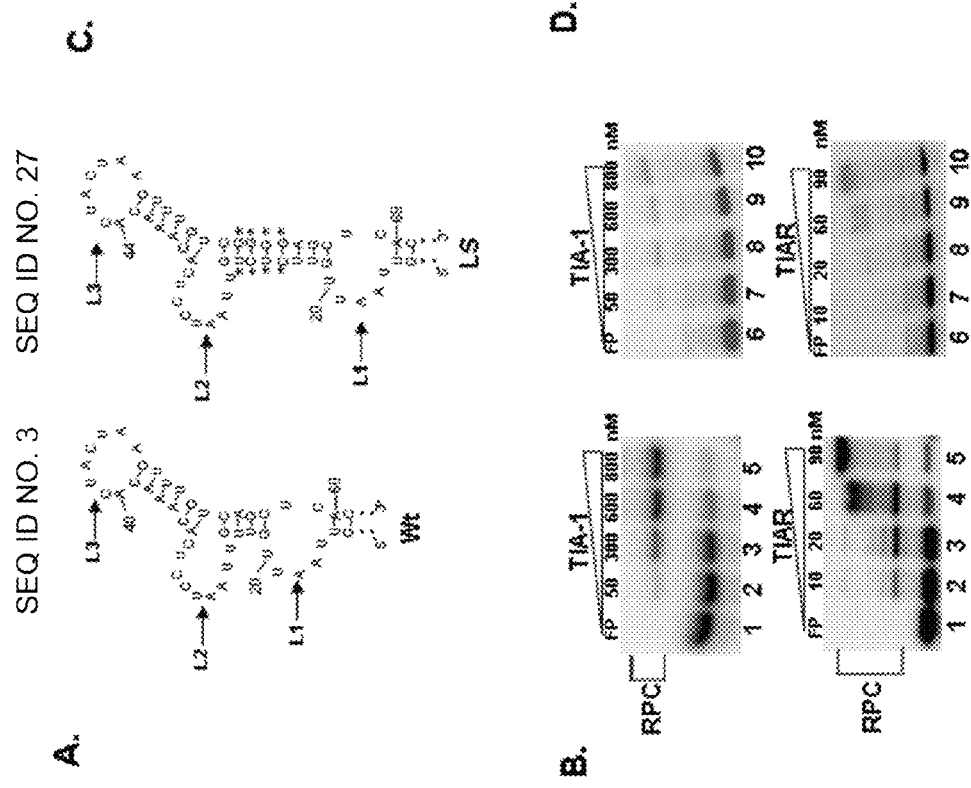
FIG. 14 A-D shows the effect of increasing the distance between L1 and L2 within the WNV3'(−)SL RNA on TIA-1 and TIAR binding activity.

FIG. 14 A-D shows the Effect of increasing the distance between L1 and L2 within the WNV3'(−)SL RNA on TIA-1 and TIAR binding activity. (A) Predicted secondary structures of the mutant RNA (LS). Mutations are indicated by asterisks. (B) Representative gel mobility shift assays with TIA-1 (upper panel) or TIAR (lower panel) and the WNV3' (−)SL or LS RNA probes. (Lanes 1-5) Wild type RNA (Lanes 6-10) LS RNA. (C) and (D) Percent RNA probe shifted.

Figure 15:
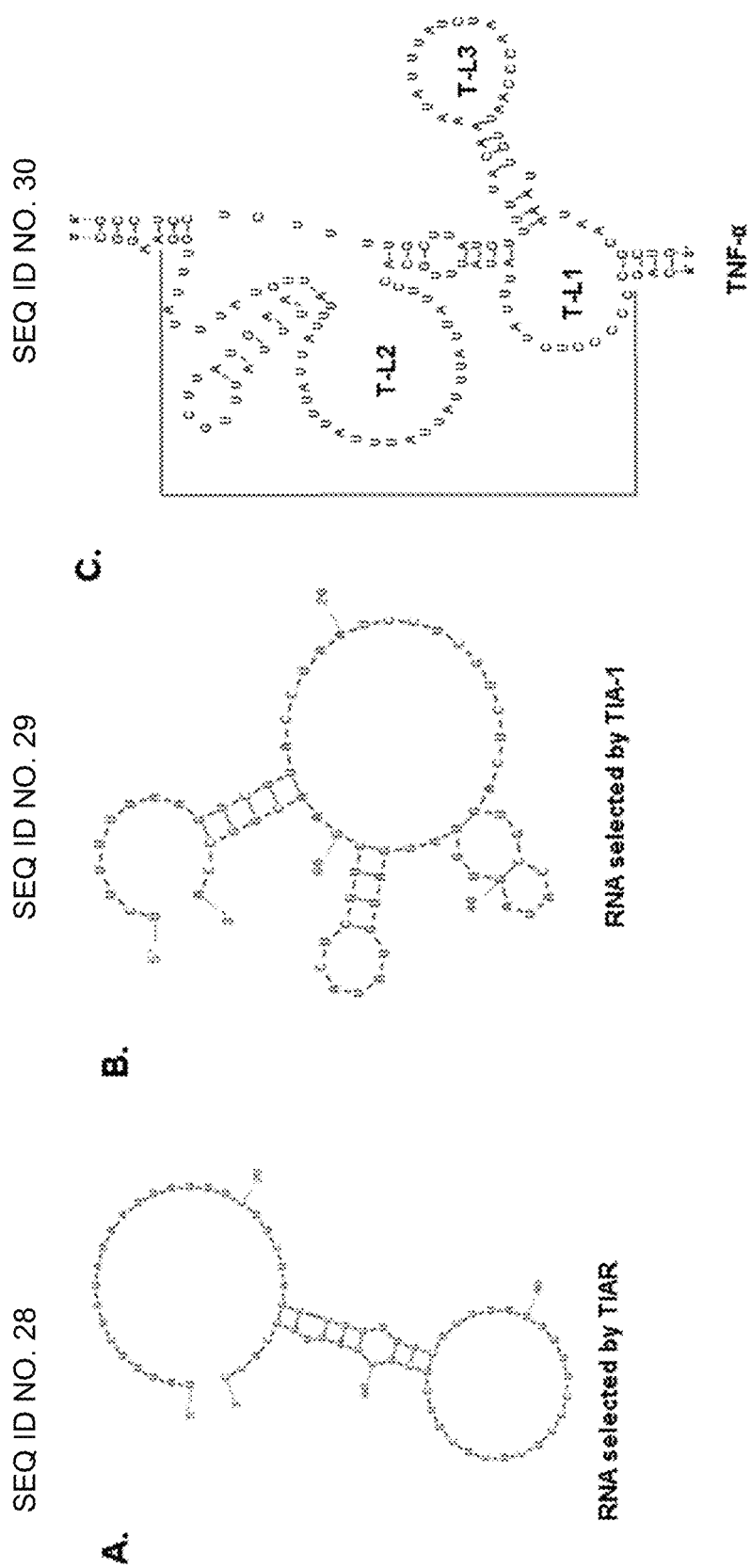
FIG. 15 A-C shows predicted secondary structures of RNAs previously reported to bind to TIA-1 and TIAR.

FIG. 15 A-C shows predicted secondary structures of RNAs previously reported to bind to TIA-1 and TIAR. Predicted secondary structures of two of the RNA sequences identified by SELEX experiments for (A) TIAR and (B) TIA-1. (C) Predicted secondary structure of TNFα mRNA. Only the part of the 3'NCR fold that contains the TIA-1 and TIAR binding region is shown. The ~80 nt mapped binding sequence is bracketed. Three AU-rich loops (T-L1, T-L2, and T-L3) are indicated.

FIG. 16A-D shows the effect of deletion of A and U nucleotides in L1, L2, or L3 (arrows) of the WNV3'(−)SL RNA on virus production. (A) and (C) Predicted secondary structure of the wild type WNV infectious clone 3'(−)SL, the mutant RNAs, and the second site revertant RNAs. Only the U nucleotides in L1 and UAA in L3 could be deleted and still preserve the predicted RNA secondary structure. Deleted nts are shown in wedges. Second site reverted nts are indicated by asterisks. (B) and (D) Plaques produced by either the wild type infectious clone RNA, the mutant RNAs, or the second site revertant RNAs by 72 hr on an RNA transfection well.

FIG. 17A-D shows the effect of C substitutions in L1, L2, or L3 of the WNV3'(−)SL RNA on virus production. (A) and (C) Predicted secondary structures of the mutant RNAs. Substituted nts are indicated by asterisks. (B) and (D) Plaques produced by either the wild type infectious clone RNA or the mutant RNAs by 72 hr on an RNA transfection well.

FIG. 18A-B shows the effect of A substitutions in L1 or L2 within the WNV3'(−) SL RNA on virus production. (A) Predicted secondary structures of mutant RNAs. Substituted nts are indicated by asterisks and the reverted nts are indicated by arrow heads. (B) Plaques produced by either the wild type infectious clone RNA, the mutant RNAs, or the partially reverted RNA by 72 hr on an RNA transfection well.

FIG. 19A-C shows the effect of the introduced mutations on the predicted secondary structure of the complementary 5'(+)SL RNA. (A) The predicted secondary structures of the 3' terminal 75 nts of the WNV minus strand RNA and the complementary 5' terminal nts of WNV genomic RNA. (B) The predicted secondary structures of the 3'(−)SL of L1 ΔU20 RNA and the complementary 5 (+)SL RNA. (C) The predicted secondary structures of the 3'(−)SL of U19→C RNA and the complementary 5'(+)SL RNA. Plaques shown were produced by 72 hr on an RNA transfection well.

Sequences

Sequences taught herein, and in the drawings, comprise the following:

SEQ ID 3
5' cagcucgcac cguguuaauu guuguuaauc cucacaaaca cuacuaaguu ugucagcuca cacaggcgaa cuacu 3'

SEQ ID 4
5' cagcucgcac cguguuaauu guugaaaaaa aaaacaaaca cuacuaaguu ugucagcuca cacaggcgaa cuacu 3'

SEQ ID 5
5' cagcucgcac cgugucaacu guuguugauc cucacaaaca cuacuaaguu ugucagcuca cacaggcgaa cuacu 3'

SEQ ID 6
5' cagcucgcac cguguccccc guuguuaauc cucacaaaca cuacuaaguu ugucagcuca cacaggcgaa cuacu 3'

SEQ ID 7
5' cagcucgcac cguguuaauu guugucccc cucacaaaca cuacuaaguu ugucagcuca cacaggcgaa cuacu 3'

SEQ ID 8
5' cagcucgcac cguguuaauu guuguuaauc cucacaaacc cccccccguu ugucagcuca cacaggcgaa cuacu 3'

SEQ ID 9
5' cagcucgcac cguguccccc guugucccc cucacaaaca cuacuaaguu ugucagcuca cacaggcgaa cuacu 3'

SEQ ID 10
5' cagcucgcac cguguaaguu guuaauccuc acaaacacua
cuaaguuugu cagcucacac aggcgaacua cu 3'

SEQ ID 11
5' cagcucgcac cguguuaauu guuguuaauc cucacaaaca
cuacguuugu cagcucacac aggcgaacua cu 3'

SEQ ID 12
5' cagcucgcac cguguaauu guugacaaac acuacuaagu
uugucagcuc acacaggcga acuacu 3'

SEQ ID 13
5' cagcucgcac cguguaaguu gacaaacacu acuaaguuug
ucagcucaca caggcgaacu ac u 3'

SEQ ID 14
5' cagcucgcac cguguaaugu ugacaaacac uacuaaguuu
gucagcucac acaggcgaac uacu 3'

SEQ ID 15
5' cagcucgcac cguguaauug uugacaaaca cuacuaaguu
ugucagcuca cacaggcgaa cuacu 3'

SEQ ID 16
5' cagcucgcac cguguaaguu guacaaacac uacuaaguuu
gucagcucac acaggcgaac uacu 3'

SEQ ID 17
5' cagcucgcac cguguaaguu guuacaaaca cuacuaaguu
ugucagcuca cacaggcgaa cuacu 3'

SEQ ID 18
5' cagcucgcac cguguaaguu guuaacaaac acuacuaagu
uugucagcuc acacaggcga acuacu 3'

SEQ ID 19
5' cagcucgcac cguguaaguu guuaaacaaa cacuacuaag
uuugucagcu cacacaggcg aacuacu 3'

SEQ ID 20
5' cagcucgcac cguguaaaac guuguuaauc cucacaaaca
cuacuaaguu ugucagcuca cacaggcgaa cuacu 3'

SEQ ID 21
5' cagcucgcac cguguuaauu guugaaaaaa aaaacaaaca
cuacuaaguu ugucagcuca cacaggcgaa cuacu 3'

SEQ ID 22
5' cagcucgcac cguguuaauu guuguuaauc cucacaaaca
aaaaaaaguu ugucagcuca cacaggcgaa cuacu 3'

SEQ ID 23
5' cagcucgcac cguguaaaac guugaaaaaa aaaacaaaca
cuacuaaguu ugucagcuca cacaggcgaa cuacu 3'

SEQ ID 24
5' cagcucgcac cguguuuuuu guuguuaauc cucacaaaca
cuacuaaguu ugucagcuca cacaggcgaa cuacu 3'

SEQ ID 25
5' cagcucgcac cguguuaauu guuguuuuuu uuuacaaaca
cuacuaaguu ugucagcuca cacaggcgaa cuacu 3'

SEQ ID 26
5' cagcucgcac cguguuaauu guuguuaauc cucacaaacu
uuuuuugu ugucagcuca cacaggcgaa cuacu 3'

SEQ ID 27
5' cagcucgcac cguguuaauu guucucuguuaauc cucacaaaca
cuacuaaguu ugucggggagcuca cacaggcgaa cuacu 3'

SEQ ID 28
5' uauuucgua uaauuauuuc uucuagccug uugcucuuau
uguuccucu cucgucgcgc cagugccacc 3'

SEQ ID 29
5' ucuuuuaag ucguaccuaa uccucgucu cagugccaua
guguaggaug uauacucguc gaacggcca 3'

SEQ ID 30
5' cagccccccu cuauuuauau uugcaccuua uuauuuauua
uuuauuuauu auuuauuuau uugcuuauga auuguauuua
uuuggaaggc gccuccucuu ugcuuauguu uuuacaaaau
auuuaucuaa cccaauuguu aaauaacgcu g 3'

SEQ ID 31
5' aguaguucgc cugugugagc ugacaaacuu aguaguguuu
gugaggauua acaacaauua acacggugcg agcug 3'

SEQ ID 32
5' cagcucgcac cguguuaagu uguuaauccu cacaaacacu
acuaaguuug ucagcucaca caggcgaacu acu 3'

SEQ ID 33
5' cagcucgcac cguguuaauu guugccucac aaacacuacu
aaguuuguca gcucacacag gcgaacuacu 3'

SEQ ID 34
5' cagcucgcac cguguuaaa uuguuaaucc ucacaaacac
uacuaaguuu gucagcucac acaggcgaac uacu 3'

SEQ ID 35
5' cagcucgcac cguguuaauu guuccucac aaacacuacu
aaguuuguca gcucacacag gcgaacuacu 3'

SEQ ID 36
5' cagcucgcac cguguaaug uuguuaaucc ucacaaacac
uacuaaguuu gucagcucac acaggcgaac uacu 3'

SEQ ID 37
5' cagcucgcac cguguaauu guuguaaucc ucacaaacac
uacuaaguuu gucagcucac acaggcgaac uacu 3'

SEQ ID 38
5' cagcucgcac cguguuaauu guugaauccu cacaaacacu
acuaaguuug ucagcucaca caggcgaacu acu 3'

SEQ ID 39
5' cagcucgcac cguguuaauu guuguuaauc cucacaaaca
cuacguuugu cagcucacac aggcgaacua cu 3'

SEQ ID 40
5' cagcucgcac cgugucaauu guuguuaauc cucacaaaca
cuacuaaguu ugucagcuca cacaggcgaa cuacu 3'

```
                                                            SEQ ID 41
5' cagcucgcac cguguuacuu guuguuaauc cucacaaaca cuacuaaguu ugucagcuca cacaggcgaa cuacu 3'

SEQ ID 42
5' cagcucgcac cguguuaauc guuguuaauc cucacaaaca cuacuaaguu ugucagcuca cacaggcgaa cuacu 3'

SEQ ID 43
5' cagcucgcac cguguuaauu guugcuaauc cucacaaaca cuacuaaguu ugucagcuca cacaggcgaa cuacu 3'

SEQ ID 44
5' cagcucgcac cguguuaauu guugucaauc cucacaaaca cuacuaaguu ugucagcuca cacaggcgaa cuacu 3'

SEQ ID 45
5' cagcucgcac cguguuaauu guuguucauc cucacaaaca cuacuaaguu ugucagcuca cacaggcgaa cuacu 3'

SEQ ID 46
5' cagcucgcac cguguuaauu guuguuaacc cucacaaaca cuacuaaguu ugucagcuca cacaggcgaa cuacu 3'

SEQ ID 47
5' cagcucgcac cguguuaacu guuguuaauc cucacaaaca cuacuaaguu ugucagcuca cacaggcgaa cuacu 3'

SEQ ID 48
5' cagcucgcac cgugucacuu guuguuaauc cucacaaaca cuacuaaguu ugucagcuca cacaggcgaa cuacu 3'

SEQ ID 49
5' cagcucgcac cguguuaauu guuguucacc cucacaaaca cuacuaaguu ugucagcuca cacaggcgaa cuacu 3'

SEQ ID 50
5' cagcucgcac cguguaaaac guuguuaauc cucacaaaca cuacuaaguu ugucagcuca cacaggcgaa cuacu 3'

SEQ ID 51
5' cagcucgcac cguguuaauu guugaaaaac cucacaaaca cuacuaaguu ugucagcuca cacaggcgaa cuacu 3'

SEQ ID 52
5' cagcucgcac cguguuaauc guuguuaauc cucacaaaca cuacuaaguu ugucagcuca cacaggcgaa cuacu 3'

SEQ ID 53
5' cagcucgcac cguguuaauu guugaaaauc cucacaaaca cuacuaaguu ugucagcuca cacaggcgaa cuacu 3'

SEQ ID 54
5' ugugagcuga caaacuuagu aguguuugug aggauuaaca acaauuaaca 3'

SEQ ID 55
5' ugugagcuga caaacuuagu aguguuugug aggauuaaca acaguuaaca 3'

SEQ ID 56
5' cagcucgcac cguguuaauu guugcccccc cucacaaaca cuacuaaguu ugucagcuca cacaggcgaa cuacu 3'

SEQ ID 57
5' cagcucgcac cguguuaauu guuguuaauc cucacaaacc ccccccguu ugucagcuca cacaggcgaa cuacu 3'
```

All references and patents cited herein are hereby incorporated in their entireties.

REFERENCES

Anderson P. 1995. TIA-1: structural and functional studies on a new class of cytolytic effector molecule. Curr Top Microbiol Immunol 198:131-143.

Anderson P, Nagler-Anderson C, O'Brien C, Levine H, Watkins S, Slayter H S, Blue M L, Schlossman S F. 1990. A monoclonal antibody reactive with a 15-kDa cytoplasmic granule-associated protein defines a subpopulation of CD8+T lymphocytes. J Immunol 144:574-582.

Beck A R, Medley Q G, O'Brien S, Anderson P, Streuli M. 1996. Structure, tissue distribution and genomic organization of the murine RRM-type RNA binding proteins TIA-1 and TIAR. Nucleic Acids Res 24:3829-3835.

Beck A R, Miller I J, Anderson P, Streuli M. 1998. RNA-binding protein TIAR is essential for primordial germ cell development. Proc Natl Acad Sci USA 95:2331-2336.

Blackwell J L, Brinton M A. 1997. Translation elongation factor-1 alpha interacts with the 3' stem-loop region of West Nile virus genomic RNA. J Virol 71:6433-6444.

Blackwell, J. L., and M. A. Brinton 1995. BHK cell proteins that bind to the 3' stem-loop structure of the West Nile virus genome RNA J Virol. 69:5650-8.

Blyn, L. B., K. M. Swiderek, O. Richards, D. C. Stahl, B. L. Semler, and E. Ehrenfeld 1996. Poly(rC) binding protein 2 binds to stem-loop IV of the poliovirus RNA 5' noncoding region: identification by automated liquid chromatography-tandem mass spectrometry Proc Natl Acad Sci USA. 93:11115-20.

Blyn, L. B., J. S. Towner, B. L. Semler, and E. Ehrenfeld 1997. Requirement of poly(rC) binding protein 2 for translation of poliovirus RNA J Virol. 71:6243-6.

Brand, S., and H. M. Bourbon 1993. The developmentally-regulated Drosophila gene rox8 encodes an RRM-type RNA binding protein structurally related to human TIA-1-type nucleolysins Nucleic Acids Res. 21:3699-704.

Brinton, M. A. 1997. Host susceptibility to viral disease, p. 303-328. In N. N. e. al (ed.), Viral Pathogenesis. Lippincott-Raven Publishers, Philadelphia.

Brinton M A. 2002. The molecular biology of West Nile Virus: a new invader of the western hemisphere. Annu Rev Microbiol 56:371-402.

Brinton M A, Dispoto J H. 1988. Sequence and secondary structure analysis of the 5'-terminal region of flavivirus genome RNA. Virology 162:290-299.

Brinton M A, Fernandez A V, Dispoto J H. 1986. The 3'-nts of flavivirus genomic RNA form a conserved secondary structure. Virology 153:113-121.

Burke, D. S., and T. P. Monath 2001. Flaviviruses, p. 1043-1125. In D. M. Knipe, and P. M. Howley (eds), Fields Virology. Lippencott Williams and Wilkins, Philadelphia.

Cahr A, Pletnev A, Vazielle-Falcoz M, Rosen L, Lai C J. 1995. Growth-restricted dengue virus mutants containing deletions in the 5' noncoding region of the RNA genome. Virology 207:68-76.

Chambers T J, Hahn C S, Galler R, Rice C M. 1990. Flavivirus genome organization, expression, and replication. Annu Rev Microbiol 44:649-688.

Cok S J, Acton S J, Sexton A E, Morrison A R. 2004. Identification of RNA-binding proteins in RAW 264.7 cells that recognize a lipopolysaccharide-responsive element in the 3-untranslated region of the murine cyclooxygenase-2 mRNA. J Biol Chem 279:8196-8205.

Davanloo, P., A. H. Rosenberg, J. J. Dunn, and F. W. Studier 1984. Cloning and expression of the gene for bacteriophage T7 RNA polymerase Proc Natl Acad Sci USA. 81:2035-9.

Davis, M. T., and T. D. Lee 1998. Rapid protein identification using a microscale electrospray LC/MS system on an ion trap mass spectrometer J Am Soc Mass Spectrom. 9:194-201.

Davis, M. T., and T. D. Lee 1997. Variable flow liquid chromatography-tandem mass spectrometry and the comprehensive analysis of complex protein digest mixtures J Am Soc Mass Spectrom. 8:1059-1069.

Del Gatto-Konczak, F., C. F. Bourgeois, C. Le Guiner, L. Kister, M. C. Gesnel, J. Stevenin, and R. Breathnach 2000. The RNA-binding protein TIA-1 is a novel mammalian splicing regulator acting through intron sequences adjacent to a 5' splice site Mol Cell Biol. 20:6287-99.

Dember L M, Kim N D, Liu K Q, Anderson P. 1996. Individual RNA recognition motifs of TIA-1 and TIAR have different RNA binding specificities. J Biol Chem 271:2783-2788.

Dirksen W P, Mohamed S A, Fisher S A. 2003. Splicing of a myosin phosphatase targeting subunit 1 alternative exon is regulated by intronic cis-elements and a novel bipartite exonic enhancer/silencer element. J Biol Chem 278:9722-9732.

Dixon D A, Balch G C, Kedersha N, Anderson P, Zimmerman G A, Beauchamp R D, Prescott S M. 2003. Regulation of cyclooxygenase-2 expression by the translational silencer TIA-1. J Exp Med 198:475-481.

Elghonemy S, Davis W G, Brinton M A. 2005. The majority of the nts in the top loop of the genomic 3' terminal stem loop structure are cis-acting in a West Nile virus infectious clone. Virology 331:238-246.

Esclatine A, Taddeo B, Roizman B. 2004. Herpes simplex virus 1 induces cytoplasmic accumulation of TIA-1/TIAR and both synthesis and cytoplasmic accumulation of tristetraprolin, two cellular proteins that bind and destabilize AU-rich RNAs. J Virol 78:8582-8592.

Forch, P., and J. Valcarcel 2001. Molecular mechanisms of gene expression regulation by the apoptosis-promoting protein TIA-1 Apoptosis. 6:463-8.

Fukui, Y., S. Yumura, and T. K. Yumura 1987. Agar-overlay immunofluorescence: high-resolution studies of cytoskeletal components and their changes during chemotaxis Methods Cell Biol. 28:347-56.

Gueydan C, Droogmans L, Chalon P, Huez G, Caput D, Kruys V. 1999. Identification of TIAR as a protein binding to the translational regulatory AU-rich element of tumor necrosis factor alpha mRNA. J Biol Chem 274:2322-2326.

Iseni F, Garcin D, Nishio M, Kedersha N, Anderson P, Kolakofsky D. 2002. Sendai virus trailer RNA binds TIAR, a cellular protein involved in virus-induced apoptosis. Embo J 21:5141-5150.

Jessen, T. H., C. Oubridge, C. H. Teo, C. Pritchard, and K. Nagai 1991. Identification of molecular contacts between the U1 A small nuclear ribonucleoprotein and U1 RNA Embo J. 10:3447-56.

Jin K, Li W, Nagayama T, He X, Sinor A D, Chang J, Mao X, Graham S H, Simon R P, Greenberg D A. 2000. Expression of the RNA-binding protein TIAR is increased in neurons after ischemic cerebral injury. J Neurosci Res 59:767-774.

Kandasamy K, Joseph K, Subramaniam K, Raymond J R, Tholanikunnel B G. 2005. Translational control of beta2-adrenergic receptor mRNA by T-cell-restricted intracellular antigen-related protein. J Biol Chem 280:1931-1943.

Kawakami A, Tian Q, Duan X, Streuli M, Schlossman S F, Anderson P. 1992. Identification and functional characterization of a TIA-1-related nucleolysin. Proc Natl Acad Sci USA 89:8681-8685.

Kedersha, N., S. Chen, N. Gilks, W. Li, I. J. Miller, J. Stahl, and P. Anderson 2002. Evidence That Ternary Complex (eIF2-GTP-tRNA(i)(Met))-Deficient Preinitiation Complexes Are Core Constituents of Mammalian Stress Granules Mol Biol Cell. 13:195-210.

Kedersha N, Cho M R, Li W, Yacono P W, Chen S, Gilks N, Golan D E, Anderson P. 2000. Dynamic shuttling of TIA-1 accompanies the recruitment of mRNA to mammalian stress granules. J Cell Biol 151:1257-1268.

Kedersha N L, Gupta M, Li W, Miller I, Anderson P. 1999. RNA-binding proteins TIA-1 and TIAR link the phosphorylation of eIF-2 alpha to the assembly of mammalian stress granules. J Cell Biol 147:1431-1442.

Kim, Y. J., and B. S. Baker 1993. Isolation of RRM-type RNA-binding protein genes and the analysis of their relatedness by using a numerical approach Mol Cell Biol. 13:174-83.

Lai M M. 1998. Cellular factors in the transcription and replication of viral RNA genomes: a parallel to DNA-dependent RNA transcription. Virology 244:1-12.

Lanciotti, R. S., J. T. Roehrig, V. Deubel, J. Smith, M. Parker, K. Steele, B. Crise, K. E. Volpe, M. B. Crabtree, J. H. Scherret, R. A. Hall, J. S. MacKenzie, C. B. Cropp, B. Panigrahy, E. Ostlund, B. Schmitt, M. Malkinson, C. Banet, J. Weissman, N. Komar, H. M. Savage, W. Stone, T. McNamara, and D. J. Gubler 1999. Origin of the West Nile virus responsible for an outbreak of encephalitis in the northeastern United States Science. 286:2333-7.

Le Guiner, C., F. Lejeune, D. Galiana, L. Kister, R. Breathnach, J. Stevenin, and F. Del Gatto-Konczak 2001. TIA-1 and TIAR Activate Splicing of Alternative Exons with Weak 5' Splice Sites followed by a U-rich Stretch on Their Own Pre-mRNAs J Biol Chem. 276:40638-46.

Le Guiner C, Gesnel M C, Breathnach R. 2003. TIA-1 or TIAR is required for DT40 cell viability. J Biol Chem 278:10465-10476.

Lewis T, Gueydan C, Huez G, Toulme J J, Kruys V. 1998. Mapping of a minimal AU-rich sequence required for lipopolysaccharide-induced binding of a 55-kDa protein on tumor necrosis factor-alpha mRNA. J Biol Chem 273:13781-13786.

Li W, Li Y, Kedersha N, Anderson P, Emara M, Swiderek K M, Moreno G T, Brinton M A. 2002. Cell proteins TIA-1 and TIAR interact with the 3' stem-loop of the West Nile virus complementary minus-strand RNA and facilitate virus replication. J Virol 76:11989-12000.

Li W, Simarro M, Kedersha N, Anderson P. 2004. FAST is a survival protein that senses mitochondrial stress and modulates TIA-1-regulated changes in protein expression. Mol Cell Biol 24:10718-10732.

Lindenbach B D, Rice C M. 2001. Flaviviridae: The viruses and their replication. Philadelphia, Pa.: Lippincott-Raven Publishers.

Lu, C. D., J. E. Houghton, and A. T. Abdelal 1992. Characterization of the arginine repressor from *Salmonella typhimurium* and its interactions with the carAB operator J Mol Biol. 225:11-24.

Mackenzie, J. M., M. K. Jones, and E. G. Westaway 1999. Markers for trans-Golgi membranes and the intermediate compartment localize to induced membranes with distinct replication functions in flavivirus-infected cells J Virol. 73:9555-67.

Mackenzie, J. M., A. A. Khromykh, M. K. Jones, and E. G. Westaway 1998. Subcellular localization and some biochemical properties of the flavivirus Kunjin nonstructural proteins NS2A and NS4A Virology. 245:203-15.

McInerney G M, Kedersha N L, Kaufman R J, Anderson P, Liljestrom P. 2005. Importance of eIF2alpha phosphorylation and stress granule assembly in alphavirus translation regulation. Mol Biol Cell 16:3753-3763.

Men R, Bray M, Clark D, Chanock R M, Lai C J. 1996. Dengue type 4 virus mutants containing deletions in the 3' noncoding region of the RNA genome: analysis of growth restriction in cell culture and altered viremia pattern and immunogenicity in rhesus monkeys. J Virol 70:3930-3937.

Parquet, M. C., A. Kumatori, F. Hasebe, K. Morita, and A. Igarashi 2001. West Nile virus-induced bax-dependent apoptosis FEBS Lett. 500:17-24.

Piecyk M, Wax S, Beck A R, Kedersha N, Gupta M, Maritim B, Chen S, Gueydan C, Kruys V, Streuli M, Anderson P. 2000. TIA-1 is a translational silencer that selectively regulates the expression of TNF-alpha. Embo J 19:4154-4163.

Rice C M, Lenches E M, Eddy S R, Shin S J, Sheets R L, Strauss J H. 1985. Nucleotide sequence of yellow fever virus: implications for flavivirus gene expression and evolution. Science 229:726-733.

Rice, C. M. 1996. Fields Virology, 3rd Edition ed. ed. Lippincott-Raven Publishers, Philadelphia.

Sambrook, J., E. F. Fritsch, and T. Maniatis 1989. Molecular cloning: a laboratory manual, 2nd ed. ed. Cold Spring Harbor Laboratory Press, Cold Spring Harbor, N.Y.

Shi, P. Y., M. A. Brinton, J. M. Veal, Y. Y. Zhong, and W. D. Wilson 1996. Evidence for the existence of a pseudoknot structure at the 3' terminus of the flavivirus genomic RNA Biochemistry. 35:4222-30.

Shi P Y, Li W, Brinton M A. 1996. Cell proteins bind specifically to West Nile virus minus-strand 3' stem-loop RNA. J Virol 70:6278-6287.

Shukla S, Del Gatto-Konczak F, Breathnach R, Fisher S A. 2005. Competition of PTB with TIA proteins for binding to a U-rich cis-element determines tissue-specific splicing of the myosin phosphatase targeting subunit 1. Rna 11:1725-1736.

Shukla S, Dirksen W P, Joyce K M, Le Guiner-Blanvillain C, Breathnach R, Fisher S A. 2004. TIA proteins are necessary but not sufficient for the tissue-specific splicing of the myosin phosphatase targeting subunit 1. J Biol Chem 279:13668-13676.

Suswam E A, Li Y Y, Mahtani H, King P H. 2005. Novel DNA-binding properties of the RNA-binding protein TIAR. Nucleic Acids Res 33:4507-4518.

Swiderek, K. M., M. T. Davis, and T. D. Lee 1998. The identification of peptide modifications derived from gel-separated proteins using electrospray triple quadrupole and ion trap analyses Electrophoresis. 19:989-97.

Taupin J L, Tian Q, Kedersha N, Robertson M, Anderson P. 1995. The RNA-binding protein TIAR is translocated from the nucleus to the cytoplasm during Fas-mediated apoptotic cell death. Proc Natl Acad Sci USA 92:1629-1633.

Tian Q, Streuli M, Saito H, Schlossman S F, Anderson P. 1991. A polyadenylate binding protein localized to the granules of cytolytic lymphocytes induces DNA fragmentation in target cells. Cell 67:629-639.

Tian Q, Taupin J, Elledge S, Robertson M, Anderson P. 1995. Fas-activated serine/threonine kinase (FAST) phosphorylates TIA-1 during Fas-mediated apoptosis. J Exp Med 182:865-874.

Vaheri, A., W. D. Sedwick, S. A. Plotkin, and R. Maes 1965. Cytopathic effect of rubella virus in RHK21 cells and growth to high titers in suspension culture Virology. 27:239-41.

Weeks, K. M., and D. M. Crothers 1992. RNA binding assays for Tat-derived peptides: implications for specificity Biochemistry. 31:10281-7.

Wiegand M, Bossow S, Neubert W J. 2005. Sendai virus trailer RNA simultaneously blocks two apoptosis-inducing mechanisms in a cell type-dependent manner. J Gen Virol 86:2305-2314.

Wilson, R., R. Ainscough, K. Anderson, C. Baynes, M. Berks, J. Bonfield, J. Burton, M. Connell, T. Copsey, J. Cooper, and et al. 1994. 2.2 Mb of contiguous nucleotide sequence from chromosome III of *C. elegans* [see comments] Nature. 368:32-8.

Yu Q, Cok S J, Zeng C, Morrison A R. 2003. Translational repression of human matrix metalloproteinases-13 by an alternatively spliced form of T-cell-restricted intracellular antigen-related protein (TIAR). J Biol Chem 278:1579-1584.

Zeng, L., B. Falgout, and L. Markoff 1998. Identification of specific nucleotide sequences within the conserved 3'-SL in the dengue type 2 virus genome required for replication J Virol. 72:7510-22.

Zhang T, Delestienne N, Huez G, Kruys V, Gueydan C. 2005. Identification of the sequence determinants mediating the nucleo-cytoplasmic shuttling of TIAR and TIA-1 RNA-binding proteins. J Cell Sci 118:5453-5463.

Zhu H, Hasman R A, Young K M, Kedersha N L, Lou H. 2003. U1 snRNP-dependent function of TIAR in the regulation of alternative RNA processing of the human calcitonin/CGRP pre-mRNA. Mol Cell Biol 23:5959-5971.

Zuker M. 2003 M fold web server for nucleic acid folding and hybridization prediction Nucleic Acids Res 31:3406-3415.

What is claimed is:

1. A composition comprising a RNA sequence selected from the group comprising a nucleic acid sequence having the nucleotide sequence of SEQ ID NO: 20, 21, 22, 23, 24, or 25.

2. The composition of claim 1, wherein the RNA sequence comprises the nucleic acid sequence having the nucleotide sequence of SEQ ID NO: 20.

3. The composition of claim 1, wherein the RNA sequence comprises the nucleic acid sequence having the nucleotide sequence of SEQ ID NO: 21.

4. The composition of claim 1, wherein the RNA sequence comprises the nucleic acid sequence having the nucleotide sequence of SEQ ID NO: 22.

5. The composition of claim 1, wherein the RNA sequence comprises the nucleic acid sequence having the nucleotide sequence of SEQ ID NO: 24.

6. The composition of claim 1, wherein the RNA sequence comprises the nucleic acid sequence having the nucleotide sequence of SEQ ID NO: 25.

7. A composition comprising a RNA sequence which comprises the nucleic acid sequence having the nucleotide sequence of SEQ ID NO: 23.

* * * * *

SEQUENCE LISTING

```
<160> NUMBER OF SEQ ID NOS: 60

<210> SEQ ID NO 1
<211> LENGTH: 21
<212> TYPE: DNA
<213> ORGANISM: Inovirus C2
```

```
<400> SEQUENCE: 1
caggaaacag ctatgaccat g                                        21

<210> SEQ ID NO 2
<211> LENGTH: 20
<212> TYPE: DNA
<213> ORGANISM: Inovirus C2

<400> SEQUENCE: 2
agtagttcgc ctgtgtgagc                                          20

<210> SEQ ID NO 3
<211> LENGTH: 75
<212> TYPE: RNA
<213> ORGANISM: West Nile virus

<400> SEQUENCE: 3
cagcucgcac gguguuaauu guuguuaauc cucacaaaca cuacuaaguu ugucagcuca    60
cacaggcgaa cuacu                                               75

<210> SEQ ID NO 4
<211> LENGTH: 75
<212> TYPE: RNA
<213> ORGANISM: West Nile virus

<400> SEQUENCE: 4
cagcucgcac cguguuaauu guugaaaaaa aaacaaaaca cuacuaaguu ugucagcuca    60
cacaggcgaa cuacu                                               75

<210> SEQ ID NO 5
<211> LENGTH: 75
<212> TYPE: RNA
<213> ORGANISM: West Nile virus

<400> SEQUENCE: 5
cagcucgcac cgugucaacu guuguugauc cucacaaaca cuacuaaguu ugucagcuca    60
cacaggcgaa cuacu                                               75

<210> SEQ ID NO 6
<211> LENGTH: 75
<212> TYPE: RNA
<213> ORGANISM: West Nile virus

<400> SEQUENCE: 6
cagcucgcac cguguccccc guuguuaauc cucacaaaca cuacuaaguu ugucagcuca    60
cacaggcgaa cuacu                                               75

<210> SEQ ID NO 7
<211> LENGTH: 75
<212> TYPE: RNA
<213> ORGANISM: West Nile virus

<400> SEQUENCE: 7
cagcucgcac cguguuaauu guugucccccc cucacaaaca cuacuaaguu ugucagcuca    60
cacaggcgaa cuacu                                               75

<210> SEQ ID NO 8
<211> LENGTH: 75
<212> TYPE: RNA
```

<213> ORGANISM: West Nile virus

<400> SEQUENCE: 8
cagcucgcac cguguuaauu guuguuaauc cucacaaacc cccccccguu ugucagcuca    60
cacaggcgaa cuacu    75

<210> SEQ ID NO 9
<211> LENGTH: 75
<212> TYPE: RNA
<213> ORGANISM: West Nile virus

<400> SEQUENCE: 9
cagcucgcac cguguccccc guugucccccc cucacaaaca cuacuaaguu ugucagcuca    60
cacaggcgaa cuacu    75

<210> SEQ ID NO 10
<211> LENGTH: 72
<212> TYPE: RNA
<213> ORGANISM: West Nile virus

<400> SEQUENCE: 10
cagcucgcac cguguaaguu guuaauccuc acaaacacua cuaaguuugu cagcucacac    60
aggcgaacua cu    72

<210> SEQ ID NO 11
<211> LENGTH: 72
<212> TYPE: RNA
<213> ORGANISM: West Nile virus

<400> SEQUENCE: 11
cagcucgcac cguguuaauu guuguuaauc cucacaaaca cuacguuugu cagcucacac    60
aggcgaacua cu    72

<210> SEQ ID NO 12
<211> LENGTH: 66
<212> TYPE: RNA
<213> ORGANISM: West Nile virus

<400> SEQUENCE: 12
cagcucgcac cguguuaauu guugacaaac acuacuaagu uugucagcuc acacaggcga    60
acuacu    66

<210> SEQ ID NO 13
<211> LENGTH: 63
<212> TYPE: RNA
<213> ORGANISM: West Nile virus

<400> SEQUENCE: 13
cagcucgcac cguguaaguu gacaaacacu acuaaguuug ucagcucaca caggcgaacu    60
acu    63

<210> SEQ ID NO 14
<211> LENGTH: 64
<212> TYPE: RNA
<213> ORGANISM: West Nile virus

<400> SEQUENCE: 14
cagcucgcac cguguaaugu ugacaaacac uacuaaguuu gucagcucac acaggcgaac    60
uacu    64

-continued

```
<210> SEQ ID NO 15
<211> LENGTH: 65
<212> TYPE: RNA
<213> ORGANISM: West Nile virus

<400> SEQUENCE: 15
cagcucgcac cguguaauug uugacaaaca cuacuaaguu ugucagcuca cacaggcgaa    60
cuacu                                                               65

<210> SEQ ID NO 16
<211> LENGTH: 64
<212> TYPE: RNA
<213> ORGANISM: West Nile virus

<400> SEQUENCE: 16
cagcucgcac cguguaaguu guacaaacac uacuaaguuu gucagcucac acaggcgaac    60
uacu                                                                64

<210> SEQ ID NO 17
<211> LENGTH: 65
<212> TYPE: RNA
<213> ORGANISM: West Nile virus

<400> SEQUENCE: 17
cagcucgcac cguguaaguu guuacaaaca cuacuaaguu ugucagcuca cacaggcgaa    60
cuacu                                                               65

<210> SEQ ID NO 18
<211> LENGTH: 66
<212> TYPE: RNA
<213> ORGANISM: West Nile virus

<400> SEQUENCE: 18
cagcucgcac cguguaaguu guuaacaaac acuacuaagu uugucagcuc acacaggcga    60
acuacu                                                              66

<210> SEQ ID NO 19
<211> LENGTH: 67
<212> TYPE: RNA
<213> ORGANISM: West Nile virus

<400> SEQUENCE: 19
cagcucgcac cguguaaguu guuaaacaaa cacuacuaag uuugucagcu cacacaggcg    60
aacuacu                                                             67

<210> SEQ ID NO 20
<211> LENGTH: 75
<212> TYPE: RNA
<213> ORGANISM: West Nile virus

<400> SEQUENCE: 20
cagcucgcac cguguaaaac guuguuaauc cucacaaaca cuacuaaguu ugucagcuca    60
cacaggcgaa cuacu                                                    75

<210> SEQ ID NO 21
<211> LENGTH: 75
<212> TYPE: RNA
<213> ORGANISM: West Nile virus
```

```
<400> SEQUENCE: 21
cagcucgcac cguguuaauu guugaaaaaa aaaacaaaca cuacuaaguu ugucagcuca      60
cacaggcgaa cuacu                                                      75

<210> SEQ ID NO 22
<211> LENGTH: 75
<212> TYPE: RNA
<213> ORGANISM: West Nile virus

<400> SEQUENCE: 22
cagcucgcac cguguuaauu guuguuaauc cucacaaaca aaaaaaaguu ugucagcuca      60
cacaggcgaa cuacu                                                      75

<210> SEQ ID NO 23
<211> LENGTH: 75
<212> TYPE: RNA
<213> ORGANISM: West Nile virus

<400> SEQUENCE: 23
cagcucgcac cguguaaaac guugaaaaaa aaaacaaaca cuacuaaguu ugucagcuca      60
cacaggcgaa cuacu                                                      75

<210> SEQ ID NO 24
<211> LENGTH: 75
<212> TYPE: RNA
<213> ORGANISM: West Nile virus

<400> SEQUENCE: 24
cagcucgcac cguguuuuuu guuguuaauc cucacaaaca cuacuaaguu ugucagcuca      60
cacaggcgaa cuacu                                                      75

<210> SEQ ID NO 25
<211> LENGTH: 75
<212> TYPE: RNA
<213> ORGANISM: West Nile virus

<400> SEQUENCE: 25
cagcucgcac cguguuaauu guuguuuuuu uuuacaaaca cuacuaaguu ugucagcuca      60
cacaggcgaa cuacu                                                      75

<210> SEQ ID NO 26
<211> LENGTH: 75
<212> TYPE: RNA
<213> ORGANISM: West Nile virus

<400> SEQUENCE: 26
cagcucgcac cguguuaauu guuguuaauc cucacaaacu uuuuuuuguu ugucagcuca      60
cacaggcgaa cuacu                                                      75

<210> SEQ ID NO 27
<211> LENGTH: 83
<212> TYPE: RNA
<213> ORGANISM: West Nile virus

<400> SEQUENCE: 27
cagcucgcac cguguuaauu guucucuguu aauccucaca aacacuacua aguuugucgg      60
ggagcucaca caggcgaacu acu                                             83
```

```
<210> SEQ ID NO 28
<211> LENGTH: 70
<212> TYPE: RNA
<213> ORGANISM: Artificial Sequence
<220> FEATURE:
<223> OTHER INFORMATION: Chemically Synthesized

<400> SEQUENCE: 28
uauuucugua uaauuauuuc uucuagccug uugcucuuau uguucccucu cucgucgcgc    60
cagugccacc                                                          70

<210> SEQ ID NO 29
<211> LENGTH: 68
<212> TYPE: RNA
<213> ORGANISM: Artificial Sequence
<220> FEATURE:
<223> OTHER INFORMATION: Chemically Synthesized

<400> SEQUENCE: 29 ucuuuuaag ucguaccuaa uccucgucuc agugccauag guaggaugu auacucgucg      60 aacggcca                                                            68

<210> SEQ ID NO 30
<211> LENGTH: 151
<212> TYPE: RNA
<213> ORGANISM: Artificial Sequence
<220> FEATURE:
<223> OTHER INFORMATION: Chemically Synthesized

<400> SEQUENCE: 30
cagccccccu cuauuuauau uugcaccuua uuauuuauua uuuauuuauu auuuauuuau    60
uugcuuauga auuguauuua uuuggaaggc gccuccucuu ugcuuauguu uuuacaaaau   120
auuuaucuaa cccaauuguu aaauaacgcu g                                  151

<210> SEQ ID NO 31
<211> LENGTH: 75
<212> TYPE: RNA
<213> ORGANISM: West Nile virus

<400> SEQUENCE: 31
aguaguucgc cugugugagc ugacaaacuu aguaguguuu gugaggauua acaacaauua    60
acacggugcg agcug                                                    75

<210> SEQ ID NO 32
<211> LENGTH: 73
<212> TYPE: RNA
<213> ORGANISM: West Nile virus

<400> SEQUENCE: 32
cagcucgcac cguguuaagu uguuaauccu cacaaacacu acuaaguuug ucagcucaca    60
caggcgaacu acu                                                      73

<210> SEQ ID NO 33
<211> LENGTH: 70
<212> TYPE: RNA
<213> ORGANISM: West Nile virus

<400> SEQUENCE: 33
cagcucgcac cguguuaauu guugccucac aaacacuacu aaguuuguca gcucacacag    60
gcgaacuacu                                                          70
```

```
<210> SEQ ID NO 34
<211> LENGTH: 73
<212> TYPE: RNA
<213> ORGANISM: West Nile virus

<400> SEQUENCE: 34
cagcucgcac cguguuaaau uguuaauccu cacaaacacu acuaaguuug ucagcucaca      60
caggcgaacu acu                                                         73

<210> SEQ ID NO 35
<211> LENGTH: 70
<212> TYPE: RNA
<213> ORGANISM: West Nile virus

<400> SEQUENCE: 35
cagcucgcac cguguuaauu guuccucac aaacacuacu aaguuuguca gcucacacag       60
gcgaacuacu                                                             70

<210> SEQ ID NO 36
<211> LENGTH: 74
<212> TYPE: RNA
<213> ORGANISM: West Nile virus

<400> SEQUENCE: 36
cagcucgcac cguguuaaug uuguuaaucc ucacaaacac uacuaaguuu gucagcucac      60
acaggcgaac uacu                                                        74

<210> SEQ ID NO 37
<211> LENGTH: 74
<212> TYPE: RNA
<213> ORGANISM: West Nile virus

<400> SEQUENCE: 37
cagcucgcac cguguuaauu guuguaaucc ucacaaacac uacuaaguuu gucagcucac      60
acaggcgaac uacu                                                        74

<210> SEQ ID NO 38
<211> LENGTH: 73
<212> TYPE: RNA
<213> ORGANISM: West Nile virus

<400> SEQUENCE: 38
cagcucgcac cguguuaauu guugaauccu cacaaacacu acuaaguuug ucagcucaca      60
caggcgaacu acu                                                         73

<210> SEQ ID NO 39
<211> LENGTH: 72
<212> TYPE: RNA
<213> ORGANISM: West Nile virus

<400> SEQUENCE: 39
cagcucgcac cguguuaauu guguuaauc cucacaaaca cuacguuugu cagcucacac       60
aggcgaacua cu                                                          72

<210> SEQ ID NO 40
<211> LENGTH: 75
<212> TYPE: RNA
<213> ORGANISM: West Nile virus

<400> SEQUENCE: 40
```
cagcucgcac cgugucaauu guuguuaauc cucacaaaca cuacuaaguu ugucagcuca    60
cacaggcgaa cuacu    75

<210> SEQ ID NO 41
<211> LENGTH: 75
<212> TYPE: RNA
<213> ORGANISM: West Nile virus

<400> SEQUENCE: 41
cagcucgcac cguguuacuu guuguuaauc cucacaaaca cuacuaaguu ugucagcuca    60
cacaggcgaa cuacu    75

<210> SEQ ID NO 42
<211> LENGTH: 75
<212> TYPE: RNA
<213> ORGANISM: West Nile virus

<400> SEQUENCE: 42
cagcucgcac cguguuaauc guuguuaauc cucacaaaca cuacuaaguu ugucagcuca    60
cacaggcgaa cuacu    75

<210> SEQ ID NO 43
<211> LENGTH: 75
<212> TYPE: RNA
<213> ORGANISM: West Nile virus

<400> SEQUENCE: 43
cagcucgcac cguguuaauu guugcuaauc cucacaaaca cuacuaaguu ugucagcuca    60
cacaggcgaa cuacu    75

<210> SEQ ID NO 44
<211> LENGTH: 75
<212> TYPE: RNA
<213> ORGANISM: West Nile virus

<400> SEQUENCE: 44
cagcucgcac cguguuaauu guugucaauc cucacaaaca cuacuaaguu ugucagcuca    60
cacaggcgaa cuacu    75

<210> SEQ ID NO 45
<211> LENGTH: 75
<212> TYPE: RNA
<213> ORGANISM: West Nile virus

<400> SEQUENCE: 45
cagcucgcac cguguuaauu guuguucauc cucacaaaca cuacuaaguu ugucagcuca    60
cacaggcgaa cuacu    75

<210> SEQ ID NO 46
<211> LENGTH: 75
<212> TYPE: RNA
<213> ORGANISM: West Nile virus

<400> SEQUENCE: 46
cagcucgcac cguguuaauu guuguuaacc cucacaaaca cuacuaaguu ugucagcuca    60
cacaggcgaa cuacu    75

<210> SEQ ID NO 47

```
<211> LENGTH: 75
<212> TYPE: RNA
<213> ORGANISM: West Nile virus

<400> SEQUENCE: 47
cagcucgcac cguguuaacu guuguuaauc cucacaaaca cuacuaaguu ugucagcuca      60
cacaggcgaa cuacu                                                      75

<210> SEQ ID NO 48
<211> LENGTH: 75
<212> TYPE: RNA
<213> ORGANISM: West Nile virus

<400> SEQUENCE: 48
cagcucgcac cgugucacuu guuguuaauc cucacaaaca cuacuaaguu ugucagcuca      60
cacaggcgaa cuacu                                                      75

<210> SEQ ID NO 49
<211> LENGTH: 75
<212> TYPE: RNA
<213> ORGANISM: West Nile virus

<400> SEQUENCE: 49
cagcucgcac cguguuaauu guuguucacc cucacaaaca cuacuaaguu ugucagcuca      60
cacaggcgaa cuacu                                                      75

<210> SEQ ID NO 50
<211> LENGTH: 75
<212> TYPE: RNA
<213> ORGANISM: West Nile virus

<400> SEQUENCE: 50
cagcucgcac cguguaaaac guuguuaauc cucacaaaca cuacuaaguu ugucagcuca      60
cacaggcgaa cuacu                                                      75

<210> SEQ ID NO 51
<211> LENGTH: 75
<212> TYPE: RNA
<213> ORGANISM: West Nile virus

<400> SEQUENCE: 51
cagcucgcac cguguuaauu guugaaaaac cucacaaaca cuacuaaguu ugucagcuca      60
cacaggcgaa cuacu                                                      75

<210> SEQ ID NO 52
<211> LENGTH: 75
<212> TYPE: RNA
<213> ORGANISM: West Nile virus

<400> SEQUENCE: 52
cagcucgcac cguguuaauc guuguuaauc cucacaaaca cuacuaaguu ugucagcuca      60
cacaggcgaa cuacu                                                      75

<210> SEQ ID NO 53
<211> LENGTH: 75
<212> TYPE: RNA
<213> ORGANISM: West Nile virus

<400> SEQUENCE: 53
cagcucgcac cguguuaauu guugaaaauc cucacaaaca cuacuaaguu ugucagcuca      60
```

-continued

```
cacaggcgaa cuacu                                                             75

<210> SEQ ID NO 54
<211> LENGTH: 50
<212> TYPE: RNA
<213> ORGANISM: West Nile virus

<400> SEQUENCE: 54
ugugagcuga caaacuuagu aguguuugug aggauuaaca acaauuaaca                       50

<210> SEQ ID NO 55
<211> LENGTH: 50
<212> TYPE: RNA
<213> ORGANISM: West Nile virus

<400> SEQUENCE: 55
ugugagcuga caaacuuagu aguguuugug aggauuaaca acaguuaaca                       50

<210> SEQ ID NO 56
<211> LENGTH: 75
<212> TYPE: RNA
<213> ORGANISM: West Nile virus

<400> SEQUENCE: 56
cagcucgcac cguguuaauu guugcccccc cucacaaaca cuacuaaguu ugucagcuca            60
cacaggcgaa cuacu                                                             75

<210> SEQ ID NO 57
<211> LENGTH: 75
<212> TYPE: RNA
<213> ORGANISM: West Nile virus

<400> SEQUENCE: 57
cagcucgcac cguguuaauu guuguuaauc cucacaaacc ccccccguu ugucagcuca             60 cacaggcgaa cuacu                                                             75

<210> SEQ ID NO 58
<211> LENGTH: 10
<212> TYPE: RNA
<213> ORGANISM: West Nile virus

<400> SEQUENCE: 58
uuaauccuca                                                                   10

<210> SEQ ID NO 59
<211> LENGTH: 10
<212> TYPE: RNA
<213> ORGANISM: West Nile virus

<400> SEQUENCE: 59
aaaaaaaaaa                                                                   10

<210> SEQ ID NO 60
<211> LENGTH: 10
<212> TYPE: RNA
<213> ORGANISM: West Nile virus

<400> SEQUENCE: 60
uuuuuuuuua                                                                   10
```